United States Patent [19]

Yellin et al.

[11] Patent Number: 4,604,465
[45] Date of Patent: Aug. 5, 1986

[54] HALOGUANIDINE INTERMEDIATES

[75] Inventors: Tobias O. Yellin, Wallingford, Pa.; Philip N. Edwards, Bramhall; Michael S. Large, Congleton, both of England

[73] Assignees: ICI Americas, Inc., Wilmington, Del.; Imperial Chemical Industries, Limited, Welwyn Garden City, England

[21] Appl. No.: 420,863

[22] Filed: Sep. 21, 1982

Related U.S. Application Data

[62] Division of Ser. No. 206,005, Nov. 12, 1980, Pat. No. 4,362,728.

[30] Foreign Application Priority Data

Nov. 13, 1979 [GB] United Kingdom ............... 7939232
Apr. 18, 1980 [GB] United Kingdom ............... 8012789
Aug. 13, 1980 [GB] United Kingdom ............... 8026420

[51] Int. Cl.[4] ............... C07D 239/42; A61K 31/505
[52] U.S. Cl. ............... 544/326; 544/194; 544/211; 544/213; 544/224; 544/239; 544/240; 544/241; 544/317; 544/320; 544/321; 544/322; 544/327; 544/330; 544/331; 544/332; 544/408; 544/409; 546/297; 546/306
[58] Field of Search ............... 544/320, 317, 321–323, 544/326–327, 330, 331

[56] References Cited

U.S. PATENT DOCUMENTS 4,336,255  6/1982  Ladd ............... 544/326
4,464,378  8/1984  Yellin et al. ............... 544/326

Primary Examiner—Glennon H. Hollrah
Assistant Examiner—James H. Turnipseed
Attorney, Agent, or Firm—Cushman, Darby & Cushman

[57] ABSTRACT

Compounds useful for inhibiting gastric acid secretion and for the treatment of peptic ulcers caused or exacerbated by gastric acidity having the following formula (I):

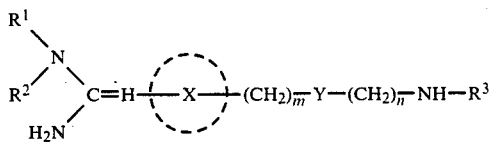

in which $R^1$ and $R^2$, are H, $C_{1-10}$ alkyl, $C_{3-8}$ cycloalkyl or cycloalkylalkyl in which the alkyl part is $C_{1-6}$ and the cycloalkyl part is $C_{3-8}$, each of the alkyl, cycloalkyl and cycloalkylalkyls being optionally substituted by one or more halogens selected from F, Cl and Br, provided that at least one of $R^1$ and $R^2$ is a halogen substituted alkyl, cycloalkyl or cycloalkylalkyl and provided that there is no halogen substituent on the carbon directly attached to the nitrogen; and X, m, Y, n and $R^3$ are as described in the specification; and the pharmaceutically-acceptable acid-addition salts thereof. Processes for producing compounds of formula (I), pharmaceutical compositions containing them, methods of utilizing such compositions and intermediates useful for synthesizing compounds of formula (I) are also described.

5 Claims, No Drawings

HALOGUANIDINE INTERMEDIATES

This is a division of application Ser. No. 206,005, filed Nov. 12, 1980, now U.S. Pat. No. 4,362,728.

This invention relates to guanidine derivatives which are histamine H-2 antagonists and which-inhibit gastric acid secretion.

It is postulated that the physiologically-active compound histamine, which occurs naturally within the animal body, is able to combine, in the course of exerting its activity, with certain specific receptors of which there are at least two distinct and separate types. The first has been named the H-1 receptor (Ash and Schild, Brit.J.Pharmac. 1966, 27, 427) and the action of histamine at this receptor is blocked (antagonised) by classical "antihistamine" drugs such as mepyramine. The second histamine receptor has been named the H-2 receptor (Black et al., Nature, 1972, 236, 385) and the action of histamine at this receptor is blocked by drugs such as cimetidine. It is known that one of the results of the blockade of the action of histamine at the H-2 receptor is the inhibition of the secretion of gastric acid and a compound which possesses this ability is therefore useful in the treatment of peptic ulcers and other conditions caused or exacerbated by gastric acidity.

In Belgian Patent No. 866,155, U.S. Pat. Nos. 4,165,377 and 4,165,378 and European Patent Specifications Publication Nos. 0006286, 0006679, 0010418 and 0010894 there are described histamine H-2 receptor antagonists which are guanidino heterocycles carrying a side chain to the end of which is attached a variously-modified guanidine residue. It has now been discovered that if the guanidine radical attached to the heterocyclic ring is substituted by a haloalkyl radical there are produced compounds which are potent histamine H-2 receptor antagonists.

According to the invention there is provided a guanidine derivative of the formula:

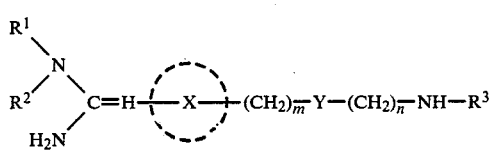

in which $R^1$ and $R^2$, which may be the same or different, are hydrogen atoms or branched or unbranched alkyl radicals of 1 to 10 carbon atoms, cycloalkyl radicals of 3 to 8 carbon atoms or cycloalkylalkyl radicals in which the alkyl part is of 1 to 6 carbon atoms and the cycloalkyl part is of 3 to 8 carbon atoms, each of the alkyl, cycloalkyl and cycloalkylalkyl radicals being optionally substituted by one or more halogen atoms selected from fluorine, chlorine and bromine atoms, provided that at least one of $R^1$ and $R^2$ is a halogen substituted alkyl, cycloalkyl or cycloalkylalkyl radical and provided that there is no halogen substituent on the carbon atom of the alkyl, cycloalkyl or cycloalkylalkyl radical which is directly attached to the nitrogen atom;

ring X is a phenyl ring carrying 1 or 2 optional substituents or a 5- or 6-membered heterocyclic aromatic ring containing 1, 2 or 3 hetero atoms selected from oxygen, nitrogen and sulphur atoms, which heterocyclic ring may, where possible, carry a single optional substituent, the optional substituents on ring X being selected from fluorine, chlorine, bromine and iodine atoms and alkyl, alkoxy and alkylthio radicals of 1 to 6 carbon atoms, trifluoromethyl, hydroxy and amino radicals;

Y is an oxygen or sulphur atom, a direct bond, a methylene, cis or trans vinylene or sulphinyl radical or a radical of the formula $NR^4$ in which $R^4$ is a hydrogen atom or an alkyl radical of 1 to 6 carbon atoms;

m is 0 to 4 and n is 1 to 5, provided that when Y is an oxygen atom, a sulphinyl radical or a radical of the formula $NR^4$, n is 2 to 5;

—$R^3$ is a radical of the formula —A—B in which A is a 3,4-dioxocyclobuten-1,2-diyl radical or a radical of the formula C=Z in which Z is an oxygen or sulphur atom or a radical of the formula NCN, $NNO_2$, $CHNO_2$, $NCONH_2$, $C(CN)_2$, $NCOR^5$, $NCO_2R^5$, $NSO_2R^5$ or $NR^6$ in which $R^5$ is an alkyl or haloalkyl radical of 1 to 6 carbon atoms, an aryl or alkylaryl radical of 6 to 10 carbon atoms or a 5- or 6-membered heterocyclic aromatic radical containing 1, 2 or 3 hetero atoms selected from oxygen, nitrogen and sulphur atoms and $R^6$ is a hydrogen atom, an alkyl or haloalkyl radical of 1 to 6 carbon atoms or an aryl or alkylaryl radical of 6 to 10 carbon atoms;

B is an alkyl, alkoxy or alkylthio radical of 1 to 6 carbon atoms or a radical of the formula $NR^7R^8$ in which $R^7$ and $R^8$, which may be the same or different, are hydrogen atoms, alkyl, haloalkyl or alkoxycarbonyl radicals of 1 to 6 carbon atoms, alkenyl or alkynyl radicals of 3 to 6 carbon atoms in which the double or triple bond respectively is separated from the nitrogen atom of $NR^7R^8$ by at least one carbon atom, (primary hydroxy)alkyl or (primary amino)alkyl radicals of 2 to 6 carbon atoms, alkylaminoalkyl or dialkylaminoalkyl radicals of up to 8 carbon atoms in which the nitrogen atom is separated from the nitrogen atom of $NR^7R^8$ by at least two carbon atoms or cycloalkyl radicals of 3 to 8 carbon atoms, or $R^7$ and $R^8$ are alkyl and are joined to form, together with the nitrogen atom to which they are attached, a 5- or 6-membered saturated ring which optionally contains an oxygen atom or an $NR^9$ radical in which $R^9$ is a hydrogen atom or an alkyl radical of 1 to 6 carbon atoms;

or —$R^3$ is a radical of the formula:

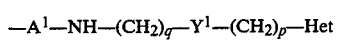

in which $Y^1$ has any one of the values given above for Y, p is 0 to 4 and q is 1 to 5, provided that when $Y^1$ is an oxygen atom, a sulphinyl radical or a radical of the formula $NR^4$ q is 2 to 5, and $A^1$ has one of the values given above for A, or —$A^1$— is a radical of the formula:

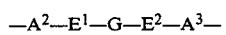

in which $A^2$ and $A^3$, which may be the same or different, have one of the values given above for A, $E^1$ and $E^2$, which may be the same or different, are oxygen or sulphur atoms or NH radicals, G is an alkylene, alkenylene, alkynylene or hydroxyalkylene radical of 2 to 12 carbon atoms and Het— is a radical of the formula:

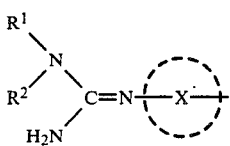

in which $R^1$, $R^2$ and X independently have the meanings stated above;

or Het— is an oxazol-4-yl, thiazol-4-yl or imidazol-4-yl radical substituted in the 2-position by a radical of the formula:

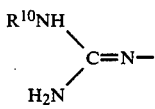

in which $R^{10}$ is a hydrogen atom, an alkyl or alkanoyl radical of 1 to 6 carbon atoms or an aroyl radical of up to 11 carbon atoms;

or Het— is a 1,2,4-thiadiazol-3-yl or 1,2,4-oxadiazol-3-yl radical substituted in the 5-position by a radical of the formula V in which $R^{10}$ has the meaning given above;

or Het is an unfused nitrogen-containing 5- or 6-membered monocyclic heterocyclic ring which is optionally substitued by an alkyl or alkoxy radical of 1 to 6 carbon atoms, a hydroxy, trifluoromethyl, hydroxymethyl or amino radical or by a halogen atom;

of Het— is a radical of the formula:

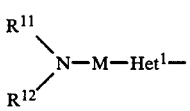

in which $R^{11}$ and $R^{12}$, which may be the same or different are hydrogen atoms or alkyl, alkenyl, alkynyl, cycloalkyl, trifluoroalkyl or alkyl substituted by a hydroxy, alkoxy, amino, alkylamino or dialkylamino radical each being a total of up to 8 carbon atoms, or aralkyl radicals of up to 12 carbon atoms or when $R^{11}$ and $R^{12}$ are alkyl, they are joined to form, together with the nitrogen atom to which they are attached, a 5- to 10-membered alicyclic heterocyclic ring; M is a straight or branched chain alkylene radical of 1 to 6 carbon atoms; and —Het¹— is a furan or thiophene ring linked through the 2 and 5 positions, a pyridine ring linked through the 2 and 6 positions or a phenyl ring linked through the 1 and 3 or 1 and 4 positions;

or —$R^3$ is a radical of the formula:

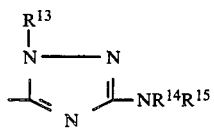

in which $R^{13}$ is a hydrogen atom, an alkyl, alkenyl, hydroxyalkyl or alkoxyalkyl radical of up to 6 carbon atoms, an aryl radical of 6 to 10 carbon atoms or an arylalkyl radical in which the aryl part is of 6 to 10 carbon atoms and the alkyl part is 1 to 6 carbon atoms and $R^{14}$ and $R^{15}$, which may be the same or different, are hydrogen atoms, alkyl, alkenyl, hydroxyalkyl or alkoxyalkyl radicals of up to 6 carbon atoms or phenyl-alkyl or pyridylalkyl radicals in which the alkyl part is of 1 to 6 carbon atoms, or $R^{14}$ and $R^{15}$ are alkyl and joined to form, together with the nitrogen atom to which they are attached, a 5- or 7-membered saturated heterocyclic ring which may optionally contain an oxygen atom or an NH radical, or $R^{14}$ and $R^{15}$ taken together represent the group $=CR^{16}R^{17}$ in which $R^{16}$ is a phenyl or pyridyl radical and $R^{17}$ is a hydrogen atom or an alkyl radical of 1 to 6 carbon atoms;

or —$R^3$ is a radical of the formula:

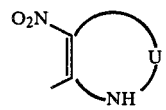

in which U is an alkylene radical of 2 to 4 carbon atoms which is optionally substituted by one or two radicals selected from alkyl radicals of 1 to 6 carbon atoms and phenylalkyl, furylalkyl, thienylalkyl and pyridylalkyl radicals in which the alkyl part is of 1 to 6 carbon atoms and the phenyl or heterocyclic ring is optionally substituted by 1 or 2 halogen atoms or methyl or methoxy radicals;

or —U— is a radical of the formula:

$$-CH_2-NR^{18}-CH_2- \qquad IX$$

in which $R^{18}$ is one of the optional substituents, given above, on U when it is an alkylene radical;

or —$R^3$ is a radical of the formula:

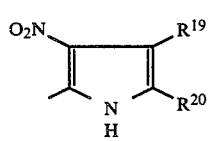

in which $R^{19}$ is a hydrogen atom or one of the optional substituents on U, given above, when it is an alkylene radical and $R^{20}$ is a hydrogen atom or an alkyl radical of 1 to 6 carbon atoms;

or —$R^3$ is a radical of the formula XI, XII, XIII or XIV:

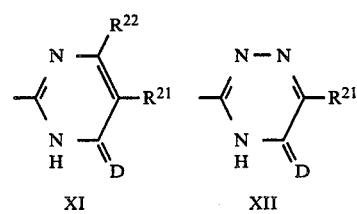

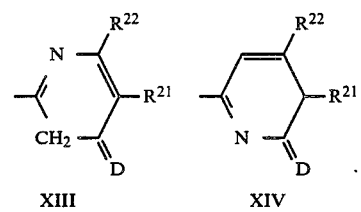

in which D is an oxygen or sulphur atom, $R^{22}$ is a hydrogen atom or an alkyl radical of 1 to 6 carbon atoms and $R^{21}$ is a hydrogen atom, an alkyl radical of 1 to 6 carbon atoms or a radical of the formula:

$$(CH_2)_r\text{—}W\text{—}(CH_2)_s\text{—}R^{23} \qquad XV$$

in which W is an oxygen or sulphur atom or a methylene radical;

r and s together are 1 to 4 when W is an oxygen or sulphur atom and r and s together are 0 to 4 when W is a methylene radical;

$R^{23}$ is a cycloalkyl radical of 3 to 6 carbon atoms or a naphthyl radical or a phenyl radical optionally substituted by a methylenedioxy or ethylenedioxy radical or, in the 2, 3, 4 or 5 positions, by one or more (same or different) halogen atoms or alkyl, alkoxy or haloalkyl radicals of 1 to 6 carbon atoms, arylalkoxy radicals in which the aryl part is of 6 to 10 carbon atoms and the alkoxy part is of 1 to 6 carbon atoms, alkoxyalkoxy radicals of 3 to 8 carbon atoms, dialkylamino radicals of 2 to 8 carbon atoms, alkoxyphenyl or alkoxyphenoxy radicals in which the alkoxy part is of 1 to 6 carbon atoms, hydroxy, phenyl, halophenyl or phenoxy radicals or $R^{23}$ is a pyridine-N-oxide, furan, thiophene, thiazole, oxazole, isothiazole, imidazole, pyrimidine, pyrazine, pyridazine, thiadiazole, quinoline, isoquinoline, benzimidazole, benzthiazole or indole ring each optionally substituted by a halogen atom, an alkyl or alkoxy radical of 1 to 6 carbon atoms or a hydroxy or amino radical;

or —$R^3$ is a pyrimid-2-yl or imidazol-2-yl radical to which is optionally fused a benzene ring, the pyrimidine and imidazole rings, or alternatively the optionally fused benzene ring, carrying 1 or 2 optional substituents selected from the group which is optionally substituted on ring X; and the pharmaceutically-acceptable acid-addition salts thereof.

It is to be understood that, in the above formulae I, IV, V, VII, VIII, X, XI, XII, XIII and XIV and throughout this specification, although the double bonds in both side chains attached to ring X have been inserted in particular positions, various other tautomeric forms are possible, and this invention includes such tautomeric forms within its scope, both in terms of the compound of the invention and in terms of the manufacturing processes. It is further to be understood that the letters C, H, N, O and S are the universally accepted contractions for the elements carbon, hydrogen, nitrogen, oxygen and sulphur respectively.

A particular value for $R^1$ or $R^2$ when it is a substituted alkyl radical is a 2,2,2-trifluoroethyl, 2,2,2-trichloroethyl, 2-chloro-2,2-difluoroethyl, 2,2-dichloro-2-fluoroethyl, 2-bromo-2,2-difluoroethyl, 2,2-dibromo-2-fluoroethyl, 2-fluoroethyl, 2-chloroethyl, 2,2-difluoroethyl, 2,2-dichloroethyl, 2-chloro-2-fluoroethyl, 2-bromo-2-fluoroethyl, 2,2,3,3,3-pentafluoropropyl, 1,1,1,3,3,3-hexafluoroisopropyl, 1,3-dichloro-1,1,3,3-tetrafluoroisopropyl, 1-chloro-1,1,3,3,3-pentafluoroisopropyl, 1,3-difluoroisopropyl or 2,2,3,3,4,4,4-heptafluorobutyl radical.

A particular value for $R^1$ or $R^2$ when it is a substituted cycloalkyl radical is a 2,2,3,3-tetrafluorocyclopropyl, 2-chloro-2,3,3-trifluorocyclopropyl, 2,2-difluorocyclopropyl, 2-chloro-3,3-difluorocyclopropyl, 2,2,3,3,4,4-hexafluorocyclobutyl or 2-chloro-2,3,3,4,4-pentafluorocyclobutyl radical.

A particular value for $R^1$ or $R^2$ when it is a substituted cycloalkylalkyl radical is a (1,2,2,3,3-pentafluorocyclopropyl)methyl, (2-chloro-1,2,3,3-tetrafluorocyclopropyl)methyl, (1,2,2,3,3,4,4-heptafluorocyclobutyl)methyl or (2-chloro-1,2,3,3,4,4-hexafluorocyclobutyl)methyl radical.

A particular value for $R^1$ and $R^2$ when it is an alkyl radical is a methyl, ethyl, propyl, isopropyl or butyl radical.

A particular value for $R^1$ or $R^2$ when it is a cycloalkyl radical is a cyclopropyl or cyclobutyl radical.

A particular value for $R^1$ or $R^2$ when it is a cycloalkylalkyl radical is a cyclopropylmethyl or cyclobutylmethyl radical.

A particular value for ring X is a phenyl, thiophene, pyridine, pyrimidine, imidazole, thiazole, oxazole, pyrazole, triazole, e.g. 1,2,4-triazole, thiadiazole, e.g. 1,2,4-thiadiazole, oxadiazole, e.g. 1,2,4-oxadiazole, pyrazine, pyridazine, isothiazole, isoxazole or triazine, e.g. 1,3,5-triazine ring.

A particular value for the optional substituent on ring X when it is an alkyl, alkoxy or alkylthio radical is a methyl, methoxy or methylthio radical.

A particular value for $R^4$ when it is an alkyl radical is a methyl radical.

A particular value for $R^5$ is a methyl, ethyl, n-propyl, i-propyl, n-butyl, trifluoromethyl, 2,2,2-trifluoroethyl, phenyl, p-tolyl or pyridyl radical, the halogen of the haloalkyl being fluoro, chloro or bromo.

A particular value for $R^6$ is a hydrogen atom or a methyl, 2,2,2-trifluoroethyl, phenyl or p-tolyl radical, the halogen of the haloalkyl being fluoro, chloro or bromo.

A particular value for B when it is an alkyl, alkoxy or alkylthio radical is a methyl, ethyl, methoxy, ethoxy or methylthio radical.

A particular value for $R^7$ or $R^8$ is a hydrogen atom or a methyl, ethyl, i-propyl, 2,2,2-trifluoroethyl, methoxycarbonyl, ethoxycarbonyl, allyl, propargyl, 2-hydroxyethyl, 2-aminoethyl, 2-methylaminoethyl, 2-dimethylaminoethyl, 2-diethylaminoethyl, cyclohexyl or phenyl radical, the halogen of the haloalkyl being fluoro, chloro or bromo.

A particular value for $R^7$ and $R^8$ when they are joined to form a ring is a pyrrolidine, piperidine, morpholine or piperazine ring.

A particular value for $R^9$ is a hydrogen atom or a methyl radical.

A particular value for G is an ethylene, trimethylene, tetramethylene, but-2-enylene, but-2-ynylene or 2-hydroxytrimethylene radical.

A particular value for $R^{10}$ is a hydrogen atom or a methyl, n-butyl, acetyl, propionyl or benzoyl radical.

A particular value for Het when it is an unfused nitrogen-containing 5- or 6-membered monocyclic heterocyclic ring is one of the particular values given above for ring X. A particular value for the optional substituent on such a ring when it is an alkyl or alkoxy radical is a methyl or methoxy radical, the optional halogen being fluoro, chloro or bromo.

A particular value for $R^{11}$ or $R^{12}$ is a hydrogen atom or a methyl, allyl, propargyl, cyclohexyl, trifluoromethyl, 2-hydroxyethyl, 2-methoxyethyl, 2-aminoethyl, 2-methylaminoethyl, 2-dimethylaminoethyl, cyclopropylmethyl or benzyl radical.

A particular value for $R^{11}$ and $R^{12}$ when they are joined to form a ring is a pyrrolidine, piperidine, piperazine or morpholine ring.

A particular value for M is a methylene, ethylene or trimethylene radical.

A particular value for $R^{13}$ is a hydrogen atom or a methyl, allyl, 2-hydroxyethyl, 2-methoxyethyl, phenyl or benzyl radical.

A particular value for $R^{14}$ or $R^{15}$ is a hydrogen atom or a methyl, allyl, 2-hydroxyethyl, 2-methoxyethyl, benzyl or pyridylmethyl radical.

A particular value for $R^{14}$ and $R^{15}$ when they are joined to form a ring is a pyrrolidine, piperidine, piperazine or morpholine ring.

A particular value for $R^{17}$ when it is an alkyl radical is a methyl radical.

A particular value for the optional substituent on U when U is an alkylene radical is a methyl, benzyl, 2-furylmethyl, 2-thienylmethyl or 2-pyridylmethyl radical.

A particular value for $R^{18}$ is one of the particular values given above for the optional substituent on U when it is an alkylene radical.

A particular value for $R^{19}$ is a hydrogen atom or one of the particular values given above for the optional substituent on U when U is an alkylene radical.

A particular value for $R^{20}$ is a hydrogen atom or a methyl radical.

A particular value for $R^{21}$ or $R^{22}$ when it is an alkyl radical is a methyl radical.

A particular value for $R^{23}$ when it is a cycloalkyl radical is a cyclohexyl radical.

A particular value for the optional substituent on $R^{23}$ when $R^{23}$ is a phenyl radical is a fluorine, chlorine or bromine atom or a methylenedioxy, ethylenedioxy, methyl, methoxy, trifluoromethyl, benzyloxy, 2-methoxyethoxy, dimethylamino, 4-methoxyphenyl, 4-methoxyphenoxy, hydroxy, phenyl, 4-chlorophenyl, 4-bromophenyl or phenoxy radical, the halogen of the haloalkyl or halophenyl being fluoro, chloro or bromo.

A particular value for the optional substituent on $R^{23}$ when $R^{23}$ is a heterocyclic ring is a fluorine, chlorine or bromine atom or a methyl, methoxy, hydroxy or amino radical.

A particular value for the optional substituent on $R^3$ when $R^3$ is a pyrimid-2-yl or imidazol-2-yl radical to which is optionally fused a benzene ring is one of the particular values for the optional substituent on ring X given above.

The following are twelve preferred features of the guanidine derivative of the formula I. When any one of these features is taken, either singly or in combination, with the other general or particular features of the guanidine derivative of the formula I listed above, there are obtained preferred sub-groups of compounds within the above general definition.

1. $R^1$ and/or $R^2$ carries at least one fluorine atom on the carbon atom which is one carbon atom removed from the nitrogen atom to which the radical is attached.
2. $R^2$ is a hydrogen atom.
3. Ring X is a phenyl, pyridine, pyrimidine, thiazole, pyrazole, thiadiazole, pyrazine or triazine ring.
4. $R^3$ is a radical of the formula —A—B in which A is a radical of the formula C=Z in which Z is an oxygen atom and B is an alkyl radical.
5. $R^3$ is a radical of the formula —A—B in which A is a radical of the formula C=Z in which Z is a radical of the formula NCN, $CHNO_2$ or $NSO_2R^5$ and B is a radical of the formula $NHR^7$.
6. $R^3$ is a radical of the formula XI or XII.
7. m is 0.
8. $R^1$ is a 2,2,2-trifluoroethyl, 2,2,2-trichloroethyl, 2-chloro-2,2-difluoroethyl, 2,2-difluoroethyl, 2,2,3,3-tetrafluoropropyl, 2,2,3,3,3-pentafluoropropyl, 1,1,1,3,3,3-hexafluoroisopropyl or 1,1,1-trifluoroisopropyl radical, and $R^2$ is a hydrogen atom.
9. Ring X is a 1,3-disubstituted phenyl ring, a pyrimidine ring in which the guanidine radical is substituted at the 4-position and $(CH_2)_m$ at the 2-position, a 2,6-disubstituted pyrazine ring or a 2,6-disubstituted pyridine ring.
10. Y is a direct bond and m+n is 4 or 5.
11. Y is a sulphur or oxygen atom or an NH radical, m is 0 and n is 2, 3 or 4.
12. $R^1$ is a 2,2,2-trifluoroethyl or 2,2,3,3,3-pentafluoropropyl radical.

Specific compound of the invention are set out in the examples. The following is a preferred group of compounds:

5-(4-chlorobenzyl)-2-(4-[2-(2,2,2-trifluoroethyl)-guanidinothiazol-4-yl]butylamino)pyrimid-4-one;

6-(3-methoxybenzyl)-3-(2-[2-(2,2,2-trifluoroethyl)-guanidinothiazol-4-yl]butylamino)-1,2,4-triazin-5-one;

3-amino-5-(2-[4-(2-[2,2,2-trifluoroethyl]guanidino)-pyrimid-2-ylmethylthio]ethylamino-1H-1,2,4-triazole;

4-[2-(2,2,2-trifluoroethyl)guanidino]-2-[3-(2-methanesulphonyl-3-[2,2,2-trifluoroethyl]guanidino)-propylthio]pyrimidine;

4-[2-(2,2,2-trifluoroethyl)guanidino]-2-[3-(2,3-bis-[2,2,2-trifluoroethyl]guanidino)propylthio]pyrimidine;

2-[2-(2,2,2-trifluoroethyl)guanidino]-4-(4-[2-(2,2,2-trifluoroethyl)guanidino]butyl)thiazole;

6-methyl-2-(5-[2-(2-[2,2,2-trifluoroethyl]guanidino)-thiazol-4-yl]pentylamino)pyrimid-4-one;

2-[2-(2,2,2-trifluoroethyl)guanidino]-4-(4-acetamidobutyl)thiazole;

2-[2-(2,2,2-trifluoroethyl)guanidino]-4-[4-(3-cyano-2-methylamidino)]butylthiazole;

5-methyl-2-(4-[2-(2-[2,2,2-trifluoroethyl]guanidino)-thiazol-4-yl]butylamino)pyrimid-4-one;

2-[2-(2,2,2-trifluoroethyl)guanidino]-4-[5-(3-cyano-2-ethylamidino)pentyl]thiazole;

2-[4-(2-[2-(2,2,2-trifluoroethyl)guanidino]thiazol-4-yl)butylamino]benzimidazole;

3-amino-1-methyl-5-[4-(2-[2-(2,2,2-trifluoroethyl)-guanidino]thiazol-4-yl)butylamino]-1H-1,2,4-triazole;

4-[2-(2,2,2-trifluoroethyl)guanidino]-2-[4-(2-cyano-3-methylguanidino)butyl]pyrimidine;

1-[4-(2-[(2,2,2-trifluoroethyl)guanidinothiazol-4-yl)butylamino]-1-methylamino-2-nitroethylene;

2-[2-(2,2,2-trifluoroethyl)guanidino]-4-[4-(2-methylsulphonyl-3-methylguanidino)butyl]thiazole;

2-[2-(2,2,2-trifluoroethyl)guanidino]-4-[4-(2-cyanoguanidino)butyl]thiazole;

4-[2-(2,2,2-trifluoroethyl)guanidino]-2-[3-(2-cyano-3-methylguanidino)propylthio]pyrimidine;

1-[3-(4-[2-(2,2,2-trifluoroethyl)guanidino]pyrimid-2-ylthio)propylamino]-1-methylamino-2-nitroethylene;

4-[2-(2,2,2-trifluoroethyl)guanidino]-2-[3-(2-cyano-3-methylguanidino)propyloxy]pyrimidine;

4-[2-(2,2,2-trifluoroethyl)guanidino]-2-[3-(2-methanesulphonyl-3-[2,2,2-trifluoroethyl]guanidino)-propylthio]pyrimidine;

and the pharmaceutically acceptable acid-addition salts thereof.

A suitable pharmaceutically-acceptable acid-addition salt of the guanidine derivative of the invention is, for example, a salt formed with hydrochloric, hydrobromic, phosphoric, sulphuric, acetic, citric or maleic acid.

The guanidine derivative of the invention may be manufactured by methods known in themselves for the manufacture of chemically-analogous compounds. The following processes, (X, Y, m, n, A, B, $A^1$, $A^2$, $A^3$, $E^1$, $E^2$, G, W, q, p, r, s, Het, $Het^1$, U, D and $R^1$ to $R^{23}$ inclusive having the meanings stated above), are therefore provided as further features of the invention.

The process of the invention is characterised by:

(a) reaction of a compound of the formula:

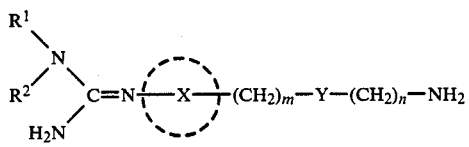  XVI with a compound of the formula $R^{24}$—$R^3$ in which $R^{24}$ is a displaceable radical. When $R^3$ is a radical of the formula A—B or of the formula II $R^{24}$ is preferably a methoxy, ethoxy or methylthio radical. When $R^3$ is a radical of the formula VII, VIII, X, XI, XII, XIII or XIV or a pyrimid-2-yl or imidazol-2-yl radical, $R^{24}$ is preferably a halogen atom, a methylthio or benzylthio radical. The reaction may be carried out in the absence of a diluent or solvent, or in the presence of a diluent or solvent such as methanol, ethanol, acetonitrile or pyridine. The reaction may be accelerated or completed by the application of heat, for example by heating to the boiling point of the diluent or solvent.

(b) for those compounds in which $R^3$ is a radical of the formula A—B in which B is an alkoxy or alkylthio radical or a radical of the formula $NR^7R^8$ or $R^3$ is a radical of the formula II, reaction of a compound of the formula:

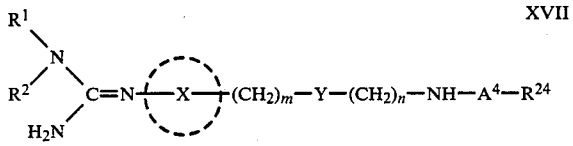  XVII in which $R^{24}$ is a displaceable radical and $A^4$ has one of the values given for A or $A^1$ with a compound of the formula $R^{25}$—H in which $R^{25}$ is an alkoxy or alkylthio radical of 1 to 6 carbon atoms, a radical of the formula $NR^7R^8$ or a radical of the formula:

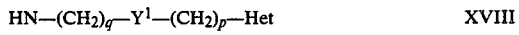
HN—$(CH_2)_q$—$Y^1$—$(CH_2)_p$—Het    XVIII

The process may be carried out using an excess of $R^{25}$—H. $R^{24}$ is preferably a methoxy, ethoxy or methylthio radical. The process may be carried out in a diluent or solvent such as water, methanol, ethanol or pyridine. The process may be accelerated by the application of heat, for example by heating to the boiling point of the diluent or solvent.

(c) for those compounds in which $R^3$ is a radical of the formula A—B in which A is a radical of the formula C=Z in which Z is a sulphur or oxygen atom and B is a radical of the formula $NR^7R^8$ in which $R^8$ is a hydrogen atom and $R^7$ has the value stated above other than a hydroxyalkyl, aminoalkyl, or alkylaminoalkyl radical, or $R^3$ is a radical of the formula II in which $A^1$ is a radical of the formula C=Z in which Z is a sulphur or oxygen atom, reaction of a compound of the formula XVI with a compound of the formula $R^{26}$—N=C=D or alternatively reaction of a compound of the formula:

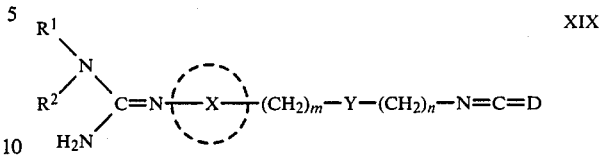  XIX with a compound of the formula $R^{26}$—$NH_2$ in which D is a sulphur or oxygen atom and $R^{26}$ is a hydrogen atom or an alkyl, haloalkyl, alkenyl, alkynyl, dialkylaminoalkyl, cycloalkyl or phenyl radical, or a radical of the formula:

$(CH_2)_q$—$Y^1$—$(CH_2)_p$—Het    XX

When D is a sulphur atom the reaction is preferably carried out in a diluent or solvent such as methanol or ethanol. When D is an oxygen atom a non-alcoholic diluent or solvent must be used.

(d) for those compounds in which $R^2$ is a hydrogen atom, reaction of a compound of the formula:

$R^1N=C=N$—X—$(CH_2)_m$—Y—$(CH_2)_n$—NH—$R^3$    XXI with ammonia. The process may be carried out in ethanol or methanol which is saturated with ammonia.

(e) for those compounds in which $R^3$ is a radical of the formula A—B in which A is a radical of the formula C=Z in which Z is a radical of the formula NCN and B is a radical of the formula $NR^7R^8$ in which $R^7$ and $R^8$ are hydrogen atoms, reaction of a compound of the formula XVI with dicyanimide or a salt thereof. The process is preferably carried out using the sodium salt of dicyanimide, in a diluent or solvent such as n-butanol. The reaction may be accelerated or completed by the application of heat, for example by heating to the boiling point of the diluent or solvent.

(f) for those compounds in which $R^3$ is a radical of the formula VII in which $R^{13}$ is other than a hydroxyalkyl radical and $R^{14}$ and $R^{15}$ are hydrogen atoms, reaction of a compound of the formula I in which $R^3$ is a radical of the formula A—B in which A is a radical of the formula C=Z in which Z is a radical of the formula NCN and B is an alkoxy or alkylthio radical, with a compound of the formula:

$H_2NNHR^{27}$    XXII in which $R^{27}$ is a hydrogen atom or an alkyl, alkenyl, alkoxyalkyl, aryl or arylalkyl radical. The process may be carried out in a diluent or solvent such as ethanol or dimethylformamide, and may be accelerated or completed by heating, for example by heating to the boiling point of the diluent or solvent.

(g) for those compounds in which $R^3$ is a radical of the formula A—B in which B is a radical of the formula C=Z, reaction of a compound of the formula XVI with a compound of the formula:

Z=C=$NR^7$    XXIII

The process may be carried out in a diluent or solvent such as ethanol or dimethylformamide.

(h) for those compounds in which the optional halogen substituent on ring X is a chlorine or bromine atom, chlorination or bromination of the corresponding unsubstituted compound. The reaction may be carried out in a diluent or solvent such as chloroform or methylene chloride.

(i) for those compounds in which $R^3$ is a radical of the formula A—B in which A is a radical of the formula C=Z in which Z is a radical of the formula $NR^6$ and B is a radical of the formula $NHR^7$, reaction of a compound of the formula:

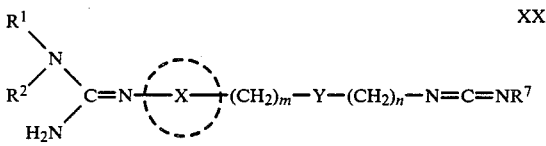
XXIV with a compound of the formula $R^6NH_2$. The reaction may be carried out in a diluent or solvent such as dimethylformamide.

(j) for those compounds in which $R^3$ is a radical of the formula A—B in which A is a radical of the formula C=Z in which Z is an oxygen or sulphur atom and B is an alkyl radical, reaction of a compound of the formula XVI with an acid, or an acylating agent derived from an acid, of the formula $R^{30}CD_2H$ in which $R^{30}$ is a hydrogen atom or an alkyl radical of 1 to 6 carbon atoms and D is an oxygen or sulphur atom. The process may be carried out in an inert diluent or solvent, and in the presence of a base, at or below room temperature. The diluent or solvent preferably is, or contains, pyridine which also acts as the base. When D is an oxygen atom, the reaction is preferably carried out using the acid chloride or acid anhydride as the acylating agent.

(k) for those compounds in which $R^3$ is an imidazol-2-yl radical to which is fused an optionally-substituted benzene ring, cyclisation of a compound of the formula:

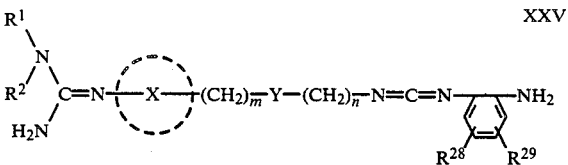
XXV in which $R^{28}$ and $R^{29}$ are the optional substituents on the benzene ring. The process may be conducted in a diluent or solvent such as dimethylformamide.

(l) for those compounds in which Y is a sulphinyl radical, oxidation of the corresponding compound in which Y is a sulphur atom. The process may be carried out using a mild oxidising agent such as sodium metaperiodate, in a diluent or solvent such as aqueous methanol or aqueous ethanol.

(m) for those compounds in which $R^3$ is a radical of the formula A—B or II in which, A, $A^1$, $A^2$ or $A^3$ is a radical of the formula C=Z in which Z is a radical of the formula $NCONH_2$, hydrolysis of the corresponding compound in which Z is a radical of the formula NCN. The process may be carried out using a dilute mineral acid, for example dilute hydrochloric acid, in a diluent or solvent such as water. The reaction may be accelerated or completed by the application of heat, for example by heating to the boiling point of the diluent or solvent.

(n) for those compounds in which Y is an oxygen or sulphur atom or a radical of the formula $NR^4$, reaction of a compound of the formula:

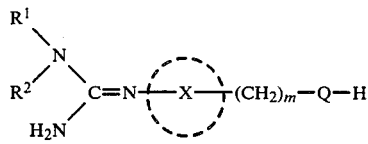
XXVI in which Q is an oxygen or sulphur atom or a radical of the formula $NR^4$ with a compound of the formula:

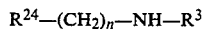

$R^{24}$—$(CH_2)_n$—NH—$R^3$   XXVII in which $R^{24}$ is a displaceable radical.

When the process of the invention manufactures the compound of the formula I in the form of the free base and an acid-addition salt is required, the compound of the formula I in the free base form is reacted with an acid which affords a pharmaceutically-acceptable anion.

A critical starting material for use in a number of the above processes is the compound of the formula XVI. This compound may also be used as an intermediate in the preparation of starting materials for a number of other processes. The compound of the formula XVI is therefore considered to be a further feature of the present invention.

The compound of the formula XVI may be prepared in a number of ways depending on the nature of the ring X and on the nature of Y. In general terms the two side chains attached to ring X may be constructed one before the other, in either order, starting either from a suitably substituted ring X or by constructing ring X itself from subfragments. When Y is a direct bond, a methylene or vinylene radical, it is generally convenient to start with a ring X carrying this side chain in which the terminal nitrogen atom is suitably protected (for example in the form of a phthalimido residue) or so to construct ring X that such a side chain inserted at the same time. On the other hand when Y is an oxygen or sulphur atom, a sulphinyl radical or a radical of the formula $NR^4$, it is generally convenient to introduce Y at a later stage of the synthesis. These general principles can be illustrated with reference to syntheses of specific ring systems.

When ring X is a pyrimidine in which the guanidine is attached to the 4-position and the other side chain to the 2-position and Y is a direct bond, a methylene or vinylene radical, the compound of the formula XVI may be obtained as follows. Reaction of a compound of the formula:

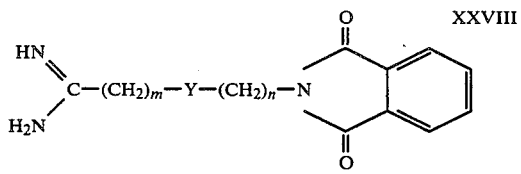
XXVIII with an optionally substituted 2-chloroacrylonitrile gives the 2-substituted-4-aminopyrimidine. When $R^2$ is a hydrogen atom, this compound is then reacted with a compound of the formula $R^1NCS$ to form the corresponding thiourea which is treated with ammonia in the presence of mercuric oxide to give the guanidine (via the carbodiimide as intermediate). Finally the amine is liberated from its protecting group. This reaction sequence is illustrated in Example 4. When $R^2$ is other than hydrogen, the aminopyrimidine is reacted with a cyanamide of the formula $R^1R^2N—C≡N$ to give the guanidine directly. Alternatively when $R^2$ is other than hydrogen, the aminopyrimidine may be treated with benzoylisothiocyanate to give the corresponding benzoylthiourea. The benzoyl group is removed and $H_2S$ is removed from the monosubstituted thiourea by reaction with mercury to give the corresponding monosubstituted cyanamide. This is then reacted with an amine of the formula $R^1R^2NH$ to give the guanidine. Finally the amine is liberated from its protecting group as before. An example of this reaction sequence as applied to a 1,3-disubstituted pyrazole ring is illustrated in Example 43 in which the amine is protected in the form of a cyano radical.

When ring X is a pyrimidine in which the guanidine is attached to the 4-position and the other side chain to the 2-position and Y is a sulphur or oxygen atom or a radical of the formula $NR^4$, the compound of the formula XVI may be obtained as follows. A compound of the formula:

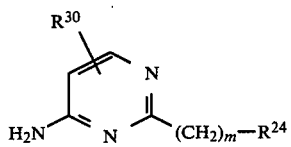    XXVIIIA in which $R^{24}$ is a displaceable radical and $R^{30}$ is the optional substituent on ring X is reacted with a compound of the formula:

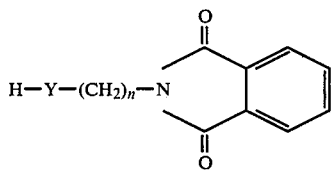    XXIX to give the compound of the formula:

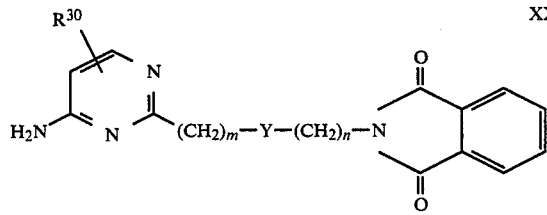    XXX

The free amino radical is then elaborated to form the substituted guanidine, as described above, and the amine is finally liberated from the protecting group. This reaction sequence is illustrated in Example 21. An alternative sequence in which the positions of $R^{24}$ and Y—H are interchanged is illustrated in Examples 16, 27 and 42. A further alternative sequence in which the substituted guanidine radical is formed before elaboration of the side chain is illustrated in Example 34. Examples of this further alternative sequence as applied to ring X when it is a 1,3-disubstituted benzene ring, a 2,6-disubstituted pyrazine ring and 2,6-disubstituted pyridine ring are illustrated in Examples 88, 86 and 32 respectively.

When ring X is a thiazole ring in which the guanidine is attached to the 2-position and the other side chain to the 4-position and Y is a sulphur or oxygen atom or a radical of the formula $NR^4$, the compound of the formula XVI may be obtained as follows. An amine of the formula $R^1R^2NH$ is reacted with sodium dicyanamide to give the compound of the formula:

    XXXI which is in turn reacted with thioacetamide and an acid (a source of $H_2S$) to give the amidinothiourea of the formula:

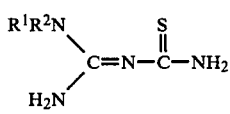    XXXII

This amidinothiourea is then reacted with a compound of the formula:

    XXXIII $ClCHR^{31}CO(CH_2)_mCl$ in which $R^{31}$ is a hydrogen atom or the optional substituent on ring X to give the compound of the formula:

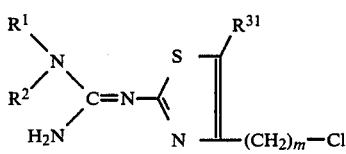    XXXIV

This compound is then reacted with a compound of the formula:

    XXXV $H—Y—(CH_2)_n—NH_2$ to give the compound of the formula XVI. This reaction sequence is illustrated in Examples 2 and 69 to 74 inclusive.

When ring X is a thiazole ring in which the guanidine is attached to the 2-position and the other side chain to the 4-position and Y is a direct bond, a methylene or vinylene radical, the compound of the formula XVI may be obtained as follows. The compound of the formula XXXII is reacted with a compound of the formula:

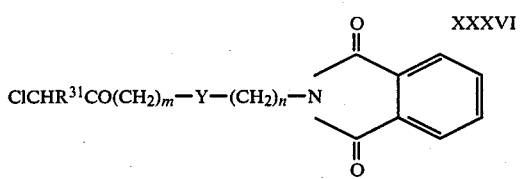    XXXVI in which $R^{31}$ is a hydrogen atom or the optional ring substituent to give the compound of the formula:

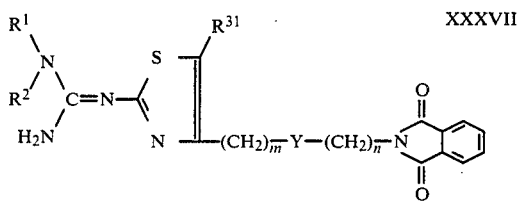

XXXVII

The protecting group is then removed to give the required product. This reaction sequence is illustrated in Examples 6, 14, 45 and 51.

When ring X is a 1,2,4-thiadiazole ring in which the guanidine is attached at the 5-position, the other side chain is attached at the 3-position, m is 1 to 4 and Y is a sulphur or oxygen atom or a radical of the formula $NR^4$, the compound of the formula XVI may be obtained as follows. A compound of the formula XXXII is reacted with bromine to give the compound of the formula:

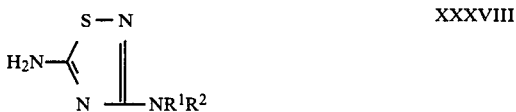

XXXVIII

This compound is then reacted with a compound of the formula:

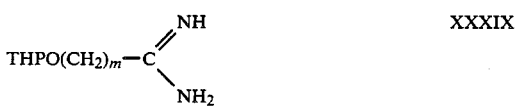

XXXIX in which THPO stands for a tetrahydropyranyl ether protecting group to give the compound of the formula:

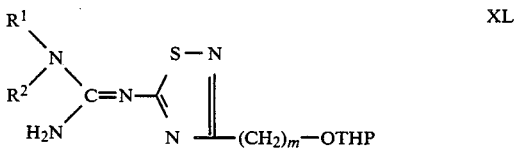

XL

The protecting group is removed and the side chain is elaborated by standard chemical methods. This reaction sequence is illustrated in Example 89.

The above general methods can be applied to other substitution patterns within the same ring X systems, and can also be applied to other ring X systems not discussed above. Alternatively, Smith, Kline and French patents such as British Pat. No. 1,338,169 describe a number of different compounds of the general formula:

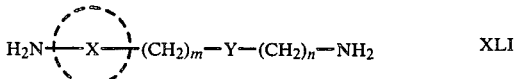

XLI

In this type of compound, the amino group attached to $(CH_2)_n$ is much more basic than that attached to ring X, and the former may thus be selectively reacted with a protecting group. The guanidine residue may then be formed by one of the methods described above and finally the protecting group removed to give the compound of the formula XVI.

When Y is a sulphinyl radical, the compound of the formula XVI may be prepared by mild oxidation of the corresponding compound in which Y is a sulphur atom.

The compound of the formula XVII for use in process (b) may be prepared by reaction of the compound of the formula XVI with a compound of the formula $R^{24}$—$A^4$—$R^{24}$, for example as described in Examples, 3, 4, 6, 8, 10, 16, 19, 20, 23, 24, 25, 27, 30, 32, 35, 36, 41, 42, 43, 45, 51, 54, 57, 67, 69, 70, 71, 72, 73, 74, 75, 76, 77, 82, 84, 85, 88 and 89.

The compound of the formula XIX for use in process (c) may be prepared by reaction of the compound of the formula XVI with thiocarbonyldiimidazole or carbonyldiimidazole, for example as described in Example 61.

The compound of the formula XXI for use in process (d) may be prepared by reaction of a compound of the formula:

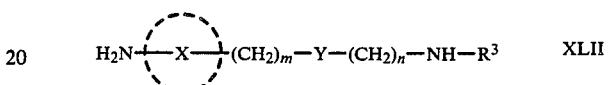

XLII (many of which are known compounds, others of which may be prepared by modifications of the processes described above) with a compound of the formula $R^1NCS$ to give the corresponding thiourea. This thiourea is treated with yellow mercuric oxide to give the carbodiimide of the formula XXI which is preferably then reacted as described in process (d) in situ without isolation, for example as described in Example 1, 25 and 31.

The compound of the formula XXIII for use in process (g) may be prepared by reaction of a compound of the formula:

XLIII with yellow mercuric oxide or silver nitrite to give the carbodiimide which is preferably reacted as described in process (g) in situ without isolation, for example as described in Examples 26, 37, 44 and 48.

The compound of the formula XXIV for use in process (i) may be prepared from the compound of the formula I in which $R^3$ is a radical of the formula A—B in which A is a radical of the formula C=Z in which Z is a sulphur atom and B is a radical of the formula $NR^7R^8$ in which $R^8$ is a hydrogen atom by reaction with yellow mercuric oxide to give the carbodiimide which is preferably reacted as described in process (i) in situ without isolation, for example as described in Example 47.

The compound of the formula XXV for use in process (k) may be prepared by reaction of a compound of the formula XIX in which D is a sulphur atom with a compound of the formula:

XLIV

The resulting thiourea is treated with silver nitrate and the carbodiimide of the formula XXV thus formed is preferably reacted as described in process (k) in situ without isolation, for example as described in Example 65.

As noted above, the guanidine derivative of the invention is a histamine H-2 antagonist, inhibits the secretion of gastric acid in warm-blooded animals and is therefore useful in the treatment of peptic ulcers and other conditions caused or exacerbated by gastric acidity, including stress ulcers and gastrointestinal bleeding due to trauma.

The histamine H-2 antagonist activity may be demonstrated on standard tests, for example by the ability of the compound of the formula I to inhibit the histamine-induced positive chronotropic response in the spontaneously beating right atrium of the guinea pig or by its ability to inhibit the histamine-induced increase in the level of cyclic AMP (in the presence of a phosphodiesterase inhibitor) in a free cell suspension obtained from canine gastric mucosa.

The guinea pig atrium test is carried out as follows:

A guinea pig right atrium is suspended at 1 g. tension (isometric) in a thermostatically-controlled (30° C.) tissue bath (25 ml.) containing oxygenated (95% $O_2$ 5% $CO_2$) Krebs-Hanseleit buffer (pH 7.4). The tissue is allowed to stabilise over 1 hour during which time it is washed 2–4 times. Individual contractions are recorded with a force-displacement transducer through a strain gauge coupler, and instantaneous rates are monitored with a cardiotachometer. A control response to 1 $\mu$M histamine is obtained after which the tissue is washed 3 times and allowed to re-equilibrate to basal rate. After re-equilibration for 15 minutes, the test compound is added to the desired final concentration. Ten minutes after addition of the compound histamine (1 $\mu$M) is again added and the response to histamine in the presence of antagonist is compared to the histamine control response. The result is expressed as a percentage of the histamine control response. Thereafter the apparent dissociation constant of the H-2 antagonist is determined by standard procedures.

All the compounds exemplified in this specification are active on the guinea pig atrium test at or below a bath concentration of 10 $\mu$M., and the more active compounds show complete inhibition of response at this concentration.

The histamine-stimulated cyclic AMP test is carried out as described by Scholes et al, *Agents and Actions*, 1976, 6, 677–682.

The inhibition of the secretion of gastric acid may be demonstrated in standard tests, for example by the ability of the compound of the formula I, when dosed intravenously, intragastrically or orally, to inhibit the secretion of acidic gastric juice in, for example, rats, cats or dogs provided with gastric fistulae and whose gastric secretion is stimulated by the administration of a secretagogue, for example pentagastrin or histamine.

The test in dogs is carried out as follows:

A female pure bred beagle (9–12 kg.) having a chronic gastric fistula is fasted overnight with water ad lib. During the experiment the dog is lightly restrained in a standing position. When studying the test compound by the intravenous route, the fistula is opened and, after ascertaining the absence of basal secretion over a period of 30 minutes, a continuous intravenous infusion of secretagogue (0.5 $\mu$mole/kg/hour of histamine or 2 $\mu$g./kg./hour pentagastrin) in saline (15 ml./hour) is begun. Gastric acid samples are collected every 15 minutes. The volume of each sample is measured and a 1 ml. aliquot is titrated to neutrality with 0.1 N NaOH to determine acid concentration. When a plateau of secretion is reached (1–2 hours), the test compound is administered intravenously in saline and gastric acid samples are collected for a further 2–3 hours during which time the infusion of the secretagogue continues uninterrupted.

When studying the test compound by the intragastric route, the absence of basal secretion over a period of 30 minutes is ascertained and the test compound, contained in 25 ml. of 0.5% w/v hydroxypropyl methylcellulose and 0.1% w/v 'Tween' 80 in water ('Tween' is a Trade Mark); is instilled into the stomach through a fistula dosing plug. One hour later, the fistula is reopened and intravenous infusion of a secretagogue, as described above, is immediately begun. Gastric acid samples are measured as described above and the approach of acid secretion to a plateau is compared to that of a control animal which is dosed intragastrically only with the dosing vehicle.

When studying the test compound by the oral route, it is administered in a gelatin capsule washed down with 15 ml. of water. One hour later, the fistula is opened and intravenous infusion of the secretagogue is immediately begun. Gastric acid samples are measured as above and the approach of acid secretion to a plateau is compared to that of an undosed control animal.

The results obtained in the atrium test are predictive of activity in the dog test.

No overt toxicity or side effects were noted during the dog tests. The compounds 1-[4-(2-[(2,2,2-trifluoroethyl)guanidinothiazol]-4-yl)butylamino]-1-methylamino-2-nitroethylene and 2-[2-(2,2,2-trifluoroethyl)guanidino]-4-[4-(2-methylsulphonyl-3-methylguanidino)butyl]thiazole in 10% w/v dimethylsulphoxide in saline (0.3 ml.) were dosed via intraperitoneal injection to two groups of five male Swiss-Webster mice (25–30 g.) at a dose of 50 mg./kg. and the animals were observed for a period of four hours, and again checked 24 hours after dosing. No toxic symptoms were noted in any of the dosed animals.

According to a further feature of the invention there is provided a pharmaceutical composition which comprises a guanidine derivative of the invention in association with a non-toxic pharmaceutically-acceptable diluent or carrier.

The pharmaceutical composition may, for example, be in a form suitable for oral, rectal, parenteral or topical administration, for which purposes it may be formulated by means known to the art into the form of, for example, tablets, capsules, aqueous or oil solutions or suspensions, emulsions, dispersible powders, suppositories, sterile injectable aqueous or oily solutions or suspensions, gels, creams, ointments or lotions.

In addition to the guanidine derivative of the formula I, the pharmaceutical composition of the invention for oral, rectal or parenteral administration may also contain, or be co-administered with, one or more known drugs selected from antacids, for example aluminium hydroxide-magnesium hydroxide mixtures; antipepsin compounds, for example pepstatin; other histamine H-2 antagonists, for example cimetidine; ulcer healing agents, for example carbenoxolone or bismuth salts; anti-inflammatory agents, for example ibuprofen, indomethacin, naproxen or aspirin; prostaglandins, for example 16,16-dimethylprostaglandin $E_2$; classical antihistamines (histamine H-1 antagonists), for example mepyramine or diphenhydramine; anticholinergic agents, for example atropine or propantheline bromide; anxiolytic agents, for example diazepam, chlordiazepoxide or phenobarbital.

The pharmaceutical composition of the invention for topical administration may also contain, in addition to the guanidine derivative, one or more classical anti-histamines (histamine H-1 antagonists), for example mepyramine or diphenhydramine and/or one or more steroidal anti-inflammatory agents, for example fluocinolone or triamcinolone.

A topical formulation may contain 1–10% w/w of the guanidine derivative of the invention. A preferred pharmaceutical composition of the invention is one suitable for oral administration in unit dosage form, for example a tablet or capsule which contains between 10 mg. and 500 mg. of the guanidine derivative, or one suitable for intravenous, subcutaneous or intramulscular injection, for example a sterile injectable containing between 0.1% and 10% w/w of the guanidine derivative.

The pharmaceutical composition of the invention will normally be administered to man to inhibit gastric acid secretion and for the treatment of peptic ulcers and other conditions caused or exacerbated by gastric acidity in the same general manner as that employed for cimetidine, due allowance being made in terms of dose levels for the potency of the guanidine derivative of the present invention relative to cimetidine. Thus each patient will receive an oral dose of between 15 mg and 1500 mg. and preferably between 20 mg. and 200 mg. of guanidine derivative or an intravenous, subcutaneous or intramuscular dose of between 1.5 mg. and 150 mg., and preferably between 5 mg. and 20 mg. of the guanidine derivative, the composition being administered 1 to 4 times per day. The rectal dose will be approximately the same as the oral dose. The composition may be administered less frequently when it contains an amount of guanidine derivative which is a multiple of the amount which is effective when given 1–4 times per day.

The invention is illustrated, but not limited by the following examples in which the temperatures are in degrees Centigrade. The preparative thin layer chromatography has been carried out on Merck 60 $F_{254}$ plates. Unless otherwise stated the ammonia was concentrated aqueous ammonia of specific gravity 0.880.

EXAMPLE 1

A mixture of 2-[3-(2,2,2-trifluoroethyl)thioureido]-4-[2-(2-cyano-3-methylguanidino)ethylthiomethyl]thiazole (0.48 g.), saturated ethanolic ammonia (20 ml.) and yellow mercuric oxide (0.5 g.) was stirred at room temperature for 3 hours and then filtered. The filtrate was evaporated to dryness, and the gummy residue (0.45 g.) converted to the hydrogen maleate salt which was recrystallised from ethanol to give 2-[2-(2,2,2-trifluoroethyl)guanidino]-4-[2-(2-cyano-3-methylguanidino)ethylthiomethyl]thiazole hydrogen maleate, m.p. 159°–160° (decomp).

The 2-[3-(2,2,2-trifluoroethyl)thioureido]-4-[2-(2-cyano-3-methylguanidino)ethylthiomethyl]thiazole used as starting material may be obtained as follows:

A mixture of 2,2,2-trifluoroethyl isothiocyanate (0.68 g.) and 2-amino-4-[2-(2-cyano-3-methylguanidino)ethylthiomethyl]thiazole (1.08 g.) in dimethylformamide (5 ml.) was maintained at 60° for 4 hours and then evaporated to dryness. The residue was recrystallised from acetonitrile to give 2-[3-(2,2,2-trifluoroethyl)thioureido]-4-[2-(2-cyano-3-methylguanidino)ethylthiomethyl]thiazole, m.p. 157°–158°.

EXAMPLE 2

Methyl isothiocyanate (80 mg.) was added to 2-[2-(2,2,2-trifluoroethyl)guanidino]-4-[(2-aminoethyl)thiomethyl]thiazole (320 mg.) dissolved in methanol (5 ml.) and the solution kept at room temperature for 18 hours and then evaporated to dryness. The residual gum was purified by preparative thin layer chromatography using ethyl acetate/methanol/ammonia 6:1:0.5 v/v/v as developing solvent to give 2-[2-(2,2,2-trifluoroethyl)guanidino]-4-[2-(3-methylthioureido)ethylthiomethyl]thiazole (90 mg.), characterised as the hydrogen maleate, m.p. 137°–139° (decomp.) (after crystallisation from acetonitrile.).

The 2-[2-(2,2,2-trifluoroethyl)guanidino]-4-[(2-aminoethyl)thiomethyl]thiazole used as starting material may be obtained as follows:

A mixture of 2,2,2-trifluoroethylamine hydrochloride (4.07 g.), butan-1-ol (20 ml.) and sodium dicyanamide (2.7 g.) was heated under reflux with stirring for 6 hours. The hot solution was filtered and the filtrate evaporated to dryness. The residual gum in a mixture of water (10 ml.) and concentrated hydrochloric acid (3.5 ml.) was stirred vigorously while adding thioacetamide (2.25 g.) in portions over 10 minutes. The mixture was stirred at room temperature for 30 minutes, heated on the steam bath for 1 hour and then kept at room temperature for 16 hours. The mixture was washed with ethyl acetate and the aqueous phase basified with saturated aqueous potassium carbonate and then extracted with ethyl acetate. The ethyl acetate extracts were dried and evaporated to dryness to give 2,2,2-trifluoroethylamidinothiourea characterised as the hydrogen maleate, m.p. 164°–166°.

A mixture of 1,3-dichloroacetone (0.254 g.) and 2,2,2-trifluoroethylamidinothiourea (0.4 g.) in acetone (10 ml.) was stirred at room temperature for 16 hours and then evaporated to dryness. A solution of the residue in ethanol (5 ml.) was cooled to 0° and stirred while adding a mixture of 2-aminoethanethiol hydrochloride (0.227 g.) and sodium ethoxide (0.41 g.) in ethanol (10 ml.) over 5 minutes. The mixture was allowed to warm to room temperature and stirred for 1 hour, and then filtered. The filtrate was evaporated to dryness and the residue was treated with water (5 ml.) and the mixture extracted with ethyl acetate (3×20 ml.). The combined ethyl acetate extracts were dried and evaporated to dryness to give 2-[2-(2,2,2-trifluoroethyl)guanidino]-4-[(2-aminoethyl)thiomethyl]thiazole as a gum (0.55 g.) which was used without further purification.

EXAMPLE 3

Dimethyl (cyanoimido)dithiocarbonate (0.22 g.) was added to 2-[2-(2,2,2-trifluoroethyl)guanidino]-4-[(2-aminoethyl)thiomethyl]thiazole (0.47 g.) in ethanol (5 ml.) and the solution kept at room temperature for 18 hours. A 33% w/v solution of methylamine in ethanol (10 ml.) was added and the mixture stirred at room temperature for two hours and then evaporated to dryness. The residual gum was purified by preparative thin layer chromatography using ethyl acetate/methanol/ammonia 6:1:0.5 v/v/v as developing solvent to give 2-[2-(2,2,2-trifluoroethyl)guanidino]-4-[2-(2-cyano-3-methylguanidino)ethylthiomethyl]thiazole (0.2 g.) which was converted to the hydrogen maleate salt identical to that described in Example 1.

EXAMPLE 4

The process described in Example 3 was repeated using 4-[2-(2,2,2-trifluoroethyl)guanidino]-2-(4-aminobutyl)pyrimidine in place of 2-[2-(2,2,2-trifluoroethyl)guanidino]-4-[(2-aminoethyl)thiomethyl]thiazole and there was thus obtained 4-[2-(2,2,2-trifluoroethyl)- guanidino]-2-[4-(2-cyano-3-methylguanidino)butyl]-
pyrimidine hydrogen maleate, m.p. 129°–132°.

The 4-[2-(2,2,2-trifluoroethyl)guanidino]-2-(4-aminobutyl)pyrimidine used as starting material may be obtained as follows:

A solution of 5-phthalimidopentanenitrile (45.6 g.) and ethanol (9.2 g.) in dioxan (150 ml.) was cooled to 0° and saturated with HCl gas. The mixture was kept at 0° for 18 hours and then evaporated to dryness. A stirred solution of the residue in methanol (200 ml.) was treated successively with sodium methoxide (10.8 g.) and ammonium chloride (10.7 g.) and the mixture stirred at room temperature for 18 hours and then filtered. The filtrate was evaporated to dryness and the residue triturated with acetonitrile and filtered to give 1-amidino-4-phthalimidobutane hydrochloride (47.5 g.), m.p. 175°–180°, which was used without further purification.

A solution of 2-chloroacrylonitrile (1.75 g.) in acetonitrile (10 ml.) was added over 15 minutes to an ice-cooled mixture of 1-amidino-4-phthalimidobutane hydrochloride (5.64 g.), acetonitrile (50 ml.) and 1,5-diazabicyclo[5,4,0]undec-5-ene (6.08 g.). The mixture was stirred for a further two hours and then evaporated to dryness. The residue was treated with water (50 ml.) and the mixture extracted with ethyl acetate (2×50 ml.). The combined ethyl acetate extracts were extracted with N hydrochloric acid (3×30 ml.) and the combined aqueous extracts neutralised with sodium bicarbonate and extracted with ethyl acetate. The ethyl acetate extracts were evaporated to dryness and the residue recrystallised from acetonitrile to give 4-amino-2-(4-phthalimidobutyl)pyrimidine (2.5 g.), m.p. 139°–140°.

A mixture of 4-amino-2-(4-phthalimidobutyl)pyrimidine (1 g.), 2,2,2-trifluoroethylisothiocyanate (1 g.) and acetonitrile was stirred at 70° for 18 hours. The mixture was diluted with acetonitrile (10 ml.), cooled in ice and then filtered to give 4-[3-(2,2,2-trifluoroethyl)thioureido]-2-(4-phthalimidobutyl)pyrimidine (1.03 g.), m.p. 204°–205°.

A mixture of 4-[3-(2,2,2-trifluoroethyl)thioureido]-2-(4-phthalimidobutyl)pyrimidine (1.02 g.), dimethyl formamide (5 ml.), ethanol (5 ml.), ammonium chloride (0.134 g.), triethylamine (0.253 g.) and yellow mercuric oxide (0.8 g.) was stirred at room temperature for 18 hours and then filtered and the filtrate evaporated to dryness. Water was added to the residue and the mixture extracted with ethyl acetate, and the ethyl acetate extract evaporated to dryness.

A solution of the residue in ethanol (20 ml.) was treated with hydrazine hydrate (0.25 g.) and the mixture heated under reflux for 0.5 hours and then evaporated to dryness. The residue was stirred with N hydrochloric acid and then filtered and the filtrate basified with 17N NaOH. The mixture was extracted with ethyl acetate, and the ethyl acetate extracts dried and evaporated to dryness to give 4-[2-(2,2,2-trifluoroethyl)guanidino]-2-(4-aminobutyl)pyrimidine as a gum (0.62 g.) which was used without further purification.

EXAMPLE 5

The process described in Example 2 was repeated using 4-[2-(2,2,2-trifluoroethyl)guanidino]-2-(4-aminobutyl)pyrimidine in place of 2-[2-(2,2,2-trifluoroethyl)guanidino]-4-[(2-aminoethyl)thiomethyl]thiazole and there was thus obtained 4-[2-(2,2,2-trifluoroethyl)-guanidino]-2-[2-(3-methylthioureido)butyl]pyrimidine hydrogen maleate, m.p. 145°–146°.

EXAMPLE 6

To a solution of 2-[2-(2,2,2 trifluoroethyl)guanidino]-4-(4-aminobutyl)thiazole (0.5 g.) in methanol (15 ml.) was added dimethyl (cyanoimido)dithiocarbonate (0.29 g.) and the solution was allowed to stand at room temperature for 3 hours. The residue obtained on evaporation of the solvent was subjected to preparative thin layer chromatography using chloroform/methanol/ammonia 90:10:0.5 v/v/v for development. The appropriate zone of the chromatogram was isolated and extracted with hot ethanol/chloroform 50:50 v/v (200 ml.). The residue (0.35 g.) obtained on evaporation of the solvent was dissolved in ethanol (2 ml.) and to this solution was added 33% w/v ethanolic methylamine (20 ml.). After standing overnight the reaction mixture was evaporated to give 2-[2-(2,2,2-trifluoroethyl)-guanidino]-4-[4-(3-cyano-2-methylguanidino)butyl]-thiazole a straw coloured glass-like material. The n.m.r. spectrum in $d_6$ dimethyl sulphoxide using tetramethylsilane as internal standard included the following resonances ($\delta$): 2.7(3H, doublet), 4.1 (2H, multiplet) 6.4 (1H, singlet) on addition of $D_2O$ the multiplet at $\delta$ 4.1 collapsed to a quartet.

The 2-[2-(2,2,2-trifluoroethyl)guanidino]-4-(4-aminobutyl)thiazole used as starting material may be prepared as follows:

To a solution of N-(6-chloro-5-oxohexyl)phthalimide (3.4 g.) in ethanol was added N-(2,2,2-trifluoroethylamidino)thiourea (2.75 g.) in ethanol (30 ml.). The mixture was heated under reflux for 2 hours and the reaction mixture concentrated to small volume by evaporation. Following treatment of the resulting solution with ether until the solution was just turbid, crystalline 2-[2-(2,2,2-trifluoroethyl)guanidino]-4-(4-phthalimidobutyl)thiazole hydrochloride (3.6 g.) was precipitated. This material (2.1 g.) in ethanol (20 ml.) and water (5 ml.) was heated to boiling and the solution pH was adjusted to 12 by addition of 2N sodium hydroxide. After heating on a steam bath for 10 minutes, the solution pH was adjusted to 3 with conc. hydrochloric acid and heating continued for a further 0.5 hour. The solution was cooled, adjusted to pH 12 with 2N sodium hydroxide and extracted with ethyl acetate (2×30 ml.). Evaporation of the washed ($H_2O$), dried (magnesium sulphate) extract gave 2-[2-(2,2,2-trifluoroethyl)guanidino]-4-(4-aminobutyl)-thiazole as a pale yellow gum which was used without further purification.

EXAMPLE 7

A mixture of 2-[2-(2,2,2-trifluoroethyl)guanidino]-4-(4-aminobutyl)thiazole (0.3 g.) and methyl isothiocyanate (0.18 g.) in methanol (6 ml.) was allowed to stand at room temperature for 3 hours. The residue obtained on evaporation of the solvent was subjected to preparative thin layer chromatography using chloroform/methanol/ammonia 90:10:0.5 v/v/v for development. The appropriate zone of the chromatogram was isolated and extracted with hot ethanol/chloroform 50:50 v/v (100 ml.). Evaporation of the solvent gave B 2-[2-(2,2,2-trifluoroethyl)guanidino]-4-[4-(3-methylthioureido)-butyl]thiazole as a straw-coloured gum. The n.m.r. spectrum $d_6$ dimethylsulphoxide using tetramethylsilane as internal standard included the following resonances ($\epsilon$): 2.75 (3H, doublet), 4.04 (2H, multiplet) and 6.34 (1H, singlet). On addition of $D_2O$ the multiplet at $\epsilon$ 4.04 collapsed to a quartet.

EXAMPLE 8

To a solution of 2-[2-(2,2,2-trifluoroethyl)guanidino]-4-(4-aminobutyl)thiazole (0.75 g.) in acetonitrile (12 ml.) was added 1,1-di(methylthio)-2-nitroethylene (0.43 g.) in warm acetonitrile (8 ml.) and the mixture was allowed to stand at room temperature overnight. The residue obtained on evaporation of the solvent was subjected to preparative thin layer chromatography using chloroform/methanol 88:12 v/v for development. The appropriate zone of the chromatogram was isolated and extracted with hot ethanol/chloroform 50:50 v/v (200 ml.) and the residue crystallised from ethanol to give 1-[4-(2-[(2,2,2,-trifluoroethyl)guanidino]thiazol-4-yl)butylamino]-1-methylthio-2-nitroethylene, m.p. 140°–141°.

EXAMPLE 9

To a solution of 1-[4-(2-[(2,2,2-trifluoroethyl)-guanidino]thiazol-4-yl)butylaminio]-1-methylthio-2-nitroethylene (10.3 g.) in warm methanol was added an excess of ethanolic methylamine (33% w/v) (20 ml.) and the mixture allowed to stand at room temperature overnight. Evaporation of the solvent and crystallisation of the residue from methanol gave 1-[4-(2-[(2,2,2-trifluoroethyl)guanidinothiazol]-4-yl)butylamino]-1-methylamino-2-nitroethylene (0.22 g.), m.p. 83°–86° (with effervescence).

EXAMPLE 10

To a solution of 2-[2-(2,2,2-trifluoroethyl)guanidino]-4-(4-aminobutyl)thiazole (0.5 g.) in ethanol (10 ml.) was added dimethyl (methylsulphonylimido)dithiocarbonate (0.35 g.) in ethanol (10 ml.) and the mixture was allowed to stand at room temperature overnight. The residue obtained on evaporation of the solvent was subjected to preparative thin layer chromatography using chloroform/methanol 90:10 v/v for development. The appropriate zone as the chromatogram was isolated and extracted with hot ethanol/chloroform 50:50 v/v (200 ml.). Evaporation of the solvent gave a gum (0.5 g.) This gum (0.17 g.) was dissolved in acetone/methanol 1:10 v/v (0.5 ml.). To this solution was added an excess of maleic acid in acetone/ether 50:50 v/v to precipitate 2-(2,2,2-trifluoroethyl)guanidino-4-[4-(3-methylsulphonyl-2-methylisothioureido)butyl]thiazole hydrogen maleate, m.p. 164°–166° (decomp.).

EXAMPLE 11

To a solution of 2-[2-(2,2,2-trifluoroethyl)guanidino]-4-[4-(3-methylsulphonyl-2-methylisothioureido)butyl]thiazole (0.33 g.) in ethanol (10 ml.) was added ethanolic methylamine (33% w/v) (25 ml.) and the mixture allowed to stand at room temperature for 48 hours. The residue obtained on evaporation of the solvent was dissolved in methanol (0.5 ml.) and to this solution was added an excess of maleic acid in ether to precipitate 2-[2-(2,2,2-trifluoroethyl)guanidino]-4-[4-(2-methylsulphonyl-3-methylguanidino)butyl]thiazole as a white powder, m.p. 93°–95°, which contained 1.5 moles of maleic acid.

EXAMPLE 12

2-[2-(2,2,2-Trifluoroethyl)guanidino]-4-(4-aminobutyl)thiazole was converted to the dihydrochloride by treatment with methanolic hydrogen chloride. This hydrochloride (0.4 g.) in n-butanol (50 ml.) was treated with sodium dicyanimide (0.11 g.) and the mixture heated under reflux for 14 hours during which time further additions (totalling 0.1 g.) of sodium dicyanimide were made. The residue obtained on evaporation of the solvent was partitioned between 0.1N sodium hydroxide (20 ml.) and ethyl acetate (60 ml.). Evaporation of the water-washed and dried (magnesium sulphate)ethyl acetate extract gave a gum which was subjected to preparative thin layer chromatography using ethyl acetate/methanol/water 6:1:1 v/v/v for development. The appropriate zone of the chromatogram was isolated and extracted with hot ethanol/chloroform 50:50 v/v (200 ml.). The residue obtained on evaporation of the solvent was dissolved in acetone (2 ml.) and to this solution was added an excess of maleic acid in acetone/ether 50:50 v/v followed by ether until precipitation began, to give 2-[2-(2,2,2-trifluoroethyl)guanidino]-4-[4-(2-cyanoguanidino)butyl]thiazole as a pale brown powder, m.p. 149°–156° (decomp.), which contained maleic acid 1.75 moles and water of crystallisation 0.5 mole.

EXAMPLE 13

To a solution of 2-[2-(2,2,2-trifluoroethyl)guanidino]-4-(3-aminopropyl)thiazole (0.2 g.) in ethanol (10 ml.) was added methyl isothiocyanate (0.2 g.) and the mixture heated under reflux for 2 hours. The residue obtained on evaporation of the solvent was subjected to preparative thin layer chromatography using chloroform/methanol/ammonia 90:10:0.5 v/v/v/ for development. The appropriate zone of the chromatogram was isolated and extracted with hot ethanol/chloroform 50:50 v/v (200 ml.). The residue obtained by evaporation of the solvent was dissolved in methanol (0.5 ml.) and to this solution was added an excess of maleic acid in acetone/ether 50:50 v/v followed by ether until precipitation began. There was thus isolated 2-[2-(2,2,2-trifluoroethyl)guanidino]-4-[3-(3-methylthioureido)propyl]thiazole hydrogen maleate, m.p. 150°–156° (decomp.).

The 2-[2-(2,2,2-trifluoroethyl)guanidino]-4-(3-aminopropyl)thiazole used as starting material may be prepared by a procedure exactly analogous to that described in Example 6 for 2-[2-(2,2,2-trifluoroethyl)-guanidino]-4-(4-aminobutyl)thiazole except that N-(5-chloro-4-oxopentyl)phthalimide is used in place of N-(6-chloro-5-oxohexyl)phthalimide.

EXAMPLE 14

An intimate mixture of 2-[2-(2,2,2-trifluoroethyl)-guanidino]-4-(4-aminobutyl)thiazole (0.39 g.) and 5-(4-chlorobenzyl)-2-methylthiopyrimid-4-one (0.39 g.) was heated at 150°–160° for 20 min. during which time effervescence occurred. The residue obtained on cooling was subjected to preparative thin layer chromatography using chloroform/methanol/ammonia 90:10:0.5 v/v/v for development. The appropriate zone of the chromatogram was isolated and extracted with hot ethanol/chloroform (50:50 v/v; 200 ml.). Evaporation of the eluate gave a glass which was dissolved in acetone (0.3 ml.) and treated with an excess of a saturated solution of maleic acid in acetone to give a maleate salt of 5-(4-chlorobenzyl)-2-{4-[2-(2,2,2-trifluoroethyl)-guanidinothiazol-4-yl]butylamino}-pyrimid-4-one a white powder (0.1 g.) which contained 1.5 moles of maleic acid and 1.5 moles of water of crystallisation. The n.m.r. spectrum in $d_6$ dimethylsulphoxide using tetramethylsilane ($\delta=0$) as internal standard included the following resonances ($\delta$): 3.45 (2H, singlet); 4.1 (2H, multiplet); 7.1 (3H, singlet-maleic acid); 7.45 (1H, singlet) and 8.2 (4H, singlet).

The 2-[2-(2,2,2-trifluoroethyl)guanidino]-4-(4-aminobutyl)thiazole used as starting material may be prepared as follows:

To a solution of N-(6-chloro-5-oxyhexyl)phthalimide (3.4 g.) in ethanol was added N-(2,2,2-trifluoroethylamidino)thiourea (2.75 g.) in ethanol (30 ml.). The mixture was heated under reflux for 2 hours and the reaction mixture concentrated to small volume by evaporation. Following treatment of the resulting solution with ether until the solution was just turbid, crystalline 2-[2-(2,2,2-trifluoroethyl)guanidino]-4-(4-phthalimidobutyl)thiazole hydrochloride (3.6 g.) was precipitated. This material (2.1 g.) in ethanol (20 ml.) and water (5 ml.) was heated to boiling and the solution pH was adjusted to 12 by addition of 2N sodium hydroxide. After heating on a steam bath for 10 minutes, the solution pH was adjusted to 3 with conc. hydrochloric acid and heating continued for a further 0.5 hour. The solution was cooled, adjusted to pH 12 with 2N sodium hydroxide and extracted with ethyl acetate (2×30 ml.). Evaporation of the washed (H₂O), dried (magnesium sulphate) extract gave 2-[2-(2,2,2-trifluoroethyl)guanidino]-4-(4-aminobutyl)thiazole as a pale yellow gum which was used without further purification.

EXAMPLE 15

An intimate mixture of 2-[2-(2,2,2-trifluoroethyl)guanidino]-4-(4-aminobutyl)thiazole (0.6 g.) and 3-methylthio-6-(3-methoxybenzyl)-1,2,4-triazine-5-one (0.6 g.) was heated at 160° for 20 min. during which time effervescence occurred. The residue obtained on cooling was triturated with hot methanol (20 ml.) and the precipitate formed on cooling was collected and suspended in hot methanol (15 ml.). To this suspension was added an excess of a solution of maleic acid in acetone whereupon a clear solution was obtained. The cooled solution was treated with ether until turbid. On standing a solid precipitated. This solid was collected and dissolved in hot methanol and decolourised with charcoal. Addition of ether to the clarified methanolic solution precipitated a maleate salt of 6-(3-methoxybenzyl)-3-{2-[2-(2,2,2-trifluoroethyl)guanidinothiazol-4-yl]butylamino}-1,2,4-triazin-5-one, which was obtained as a fawn powder (0.1 g.) which contained one mole of maleic acid and 3 moles of water of crystallisation. The n.m.r. spectrum in d₆ dimethylsulphoxide using tetramethylsilane as internal standard (δ=0) included the following resonances (δ): 3.7 (2H, singlet+3H, singlet); 4.1 (2H, multiplet); 7.1 (2H, singlet-maleic acid); 7.45 (1H, singlet); and 7.75 (3H, multiplet).

EXAMPLE 16

A solution of 4-[2-(2,2,2-trifluoroethyl)guanidino]-2-[(3-amino)propylthio]pyrimidine (180 mg.) in acetonitrile (2 ml.) was treated with dimethyl (cyanoimido)dithiocarbonate (85 mg.) and the solution stood at room temperature for 18 hours. The crystalline solid which precipitated was collected to give 4-[2-(2,2,2-trifluoroethyl)guanidino]-2-[3-(3-cyano-2-methylisothioureido)-propylthio]pyrimidine (175 mg.), m.p. 189°-190°.

The 4-[2-(2,2,2-trifluoroethyl)guanidino]-2-[(3-amino)propylthio]pyrimidine used as starting material may be prepared as follows:

A mixture of thiocytosine (248 mg.), 1,5-diazabicyclo[5,4,0]undec-5-ene (300 mg.), ethanol (10 ml.) and N-3-bromopropylphthalimide (536 mg.) was stirred at room temperature for 2 hours and then evaporated to dryness. The residue was partitioned between water and ethyl acetate, and the ethyl acetate extract dried and evaporated to dryness. A mixture of the residue (700 mg.), acetonitrile (3 ml.) and 2,2,2-trifluoroethylisothiocyanate (420 mg.) was stirred at 70° for 18 hours then cooled and filtered to give 4-[3-(2,2,2-trifluoroethylthioureido]-2-[(3-phthalimido)propylthio]-pyrimidine (480 mg.), m.p. 214°-215° after recrystallisation from a mixture of ethanol and N,N-dimethylformamide.

A mixture of 4-[3-(2,2,2-trifluoroethyl)thioureido]-[(3-phthalimido)propylthio]pyrimidine (0.4 g.), N,N-dimethylformamide (5 ml.), saturated ethanolic ammonia (10 ml.) and yellow mercuric oxide (280 mg.) was stirred at room temperature for 3 hours and then filtered and the filtrate evaporated to dryness. A solution of the residue in ethanol (10 ml.) was treated with hydrazine hydrate (1 ml.), the mixture heated under reflux for 1 hour and then evaporated to dryness. The residue was stirred with 1N hydrochloric acid and then filtered and the filtrate basified with 17N NaOH. The mixture was extracted with ether and the combined ether extracts dried and evaporated to dryness to give 4-[2-(2,2,2-trifluoroethyl)guanidino]-2-[(3-amino)propylthio]pyrimidine which was used without further purification.

EXAMPLE 17

A solution of 4-[2-(2,2,2-trifluoroethyl)guanidino]-2-[3-(2-cyano-2-methylsiothioureido)propylthio]pyrimidine (140 mg.) in 33% w/v ethanolic methylamine (5 ml.) was allowed to stand at room temperature for 4 hours. The solution was evaporated to dryness and the residue recrystallised from ethyl acetate to give 4-[2-(2,2,2-trifluoroethyl)guanidino]-2-[3-(2-cyano-3-methylguanidino)propylthio]pyrimidine (105 mg.), m.p. 159°-160°.

EXAMPLE 18

2,2,2-Trifluoroethylisothiocyanate (0.31 g.) was added to a solution of 4-[2-(2,2,2-trifluoroethyl)guanidino]-2-(4-aminobutyl)pyrimidine (0.58 g.) in acetonitrile (5 ml.), and the solution kept at room temperature for 18 hours and then evaporated to dryness. The residual gum was purified by preparative thin layer chromatography using ethyl acetate/methanol/ammonia 6:1:0.5 v/v/v as developing solvent to give 4-[2-(2,2,2-trifluoroethyl)guanidino]-2-[4-(2,2,2-trifluoroethyl)thioureido)butyl]pyrimidine (0.22 g.) characterised as the hydrogen maleate, m.p. 142°-145° (after recrystallisation from acetonitrile).

By a similar process, using the appropriate isothiocyanate in place of 2,2,2-trifluoroethylisothiocyanate there were obtained 4-[2-(2,2,2-trifluoroethyl)guanidino]-2-[4-(3-methoxycarbonylthioureido)butyl]-pyrimidine hydrogen maleate, m.p. 168°-169° (decomp.), and 4-[2-(2,2,2-trifluoroethyl)guanidino]-2-[4-(3-phenylthioureido)butyl]pyrimidine, m.p. 124°-127°.

EXAMPLE 19

Dimethyl(cyanoimido)dithiocarbonate (0.33 g.) was added to a solution of 4-[2-(2,2,2-trifluoroethyl)guanidino]-2-(4-aminobutyl)pyrimidine (0.66 g.) in acetonitrile (5 ml.) and the solution kept at room temperature for 18 hours and then evaporated to dryness. The residue was triturated with a small volume of acetonitrile and then filtered to give 4-[2-(2,2,2-trifluoroethyl)- guanidino]-2-[4-(3-cyano-2-methylisothioureido)butyl]-pyrimidine, m.p. 164°–166°.

EXAMPLE 20

A solution of dimethyl(methanesulphonylimido)dithiocarbonate (0.2 g.) in acetonitrile (5 ml.) was added to a solution of 4-[2-(2,2,2-trifluoroethyl)guanidino]-2-(4-aminobutyl)pyrimidine (0.29 g.) in a acetonitrile (2 ml.) and the solution left at room temperature for 18 hours and then evaporated to dryness. The residue was dissolved in a 33% w/v solution of methylamine in ethanol (5 ml.), and the solution kept at room temperature for 18 hours and then evaporated to dryness. A solution of the residue in ethyl acetate was added to a solution of maleic acid in acetone and the precipitate collected and recrystallised from acetonitrile to give 4-[2-(2,2,2-trifluoroethyl)guanidino]-2-[4-(3-methylsulphonyl-2-methylguanidino)butyl]pyrimidine hydrogen maleate (0.25 g.), m.p. 162°–165°.

By a similar process, using 1,1-bis(methylthio)-2-nitroethylene in place of dimethyl(methanesulphonylimido)dithiocarbonate, there was obtained 1-[4-(2-[(2,2,2-trifluoroethyl)guanidino]pyrimid-2-yl)butylamino]-1-methylamino-2-nitroethylene hydrogen maleate, m.p. 167°–169°.

EXAMPLE 21

1-Nitro-2-methylisothiourea (0.135 g.) was added to a stirred solution of 4-[2-(2,2,2-trifluoroethyl)guanidino]-2-[(2-aminoethyl)thiomethyl]pyrimidine (0.31 g.) in acetonitrile (5 ml.) and the suspension stirred at room temperature for 2 hours. The insoluble material was collected to give 4-[2-(2,2,2-trifluoroethyl)guanidino]-2-[2-(2-nitro-3-methylguanidino)ethylthiomethyl]pyrimidine (0.35 g.) m.p. 199°–200° (decomp.)

The 4-[2-(2,2,2-trifluoroethyl)guanidino]-2-[(2-aminoethyl)thiomethyl]pyrimidine used as starting material may be obtained as follows:

Solutions of 2-chloroacrylonitrile (15.7 g.) in acetonitrile (20 ml.) and 1,5-diazabicyclo[5,4,0]undec-5-ene (27 g.) in acetonitrile (20 ml.) were added simultaneously over 30 minutes to a stirred, ice-cooled solution of 2-chloroacetamidine hydrochloride (19.2 g.) and 1,5-diazabicyclo[5,4,0]undec-5-ene (22.5 g.) in acetonitrile (200 ml.), keeping the temperature below 30° and the mixture stirred a further 4 hours at room temperature after the addition was complete. The resulting mixture was stirred with a mixture of water (100 ml.) and ethyl acetate (200 ml.) and then filtered through a pad of diatomaceous earth and the ethyl acetate phase separated. The aqueous phase was further extracted with ethyl acetate (2×100 ml.) and the combined ethyl acetate extracts dried and evaporated to dryness to give 4-amino-2-chloromethylpyrimidine (14.5 g.) which was used without further purification.

A solution of 4-amino-2-chloromethylpyrimidine (11.6 g.) in methanol (20 ml.) was added over 15 minutes to a stirred mixture of sodium methoxide (4.32 g.), N-(2-mercaptoethyl)phthalimide (16.6 g.) and methanol (100 ml.), and the mixture stirred for 1 hour after the addition was complete and then evaporated to dryness. The residue was partitioned between 1N hydrochloric acid and ethyl acetate, and the aqueous phase separated and neutralised by the addition of sodium bicarbonate. The mixture was extracted with ethyl acetate and the extracts dried and evaporated to dryness, and the residue was recrystallised from acetonitrile to give 4-amino-2-[(2-phthalimidoethyl)thiomethyl]pyrimidine, m.p. 131°–133°.

A mixture of 4-amino-2-[(2-phthalimidoethyl)thiomethyl]pyrimidine (5.9 g.), 2,2,2-trifluoroethylisothiocyanate (3.9 g.) and acetonitrile (20 ml.) was stirred at 70° for 72 hours. The reaction mixture was cooled and the crystalline precipitate collected to give 4-[3-(2,2,2-trifluoroethyl)thioureido]-2-[(2-phthalimidoethyl)thiomethyl]pyrimidine (5.35 g.), m.p. 178°–179°.

A mixture of 4-[3-(2,2,2-trifluoroethyl)thioureido]-2-[(2-phthalimidoethyl)thiomethyl]pyrimidine (6.8 g.), dimethylformamide (30 ml.), saturated ethanolic ammonia (5 ml.) and yellow mercuric oxide (6.5 g.) was stirred at room temperature for 2 hours and then filtered. The filtrate was evaporated to dryness and the residue triturated with ether and filtered to give 4-[2-(2,2,2-trifluoroethyl)guanidino]-2-[(2-phthalimidoethyl)thiomethyl]pyrimidine (5.6 g.), m.p. 167°–168° after crystallisation from ethanol.

A mixture of 4-[2-(2,2,2-trifluoroethyl)guanidino]-2-[(2-phthalimidoethyl)thiomethyl]pyrimidine (5.4 g.), ethanol (30 ml.) and 99% hydrazine hydrate (3 ml.) was heated under reflux for 1 hour and then evaporated to dryness. The residue was stirred with N hydrochloric acid and then filtered and the filtrate basified with 17N NaOH. The mixture was extracted with ether, and the ether extracts dried and evaporated to dryness to give 4-[2-(2,2,2-trifluoroethyl)guanidino]-2-[(2-aminoethyl)thiomethyl]pyrimidine (2.93 g.) which was used without further purification.

EXAMPLE 22

A mixture of 4-[2-(2,2,2,-trifluoroethyl)guanidino]-2-[(2-aminoethyl)thiomethyl]pyrimidine (0.31 g.) 1-methylamino-1-methylthio-2-nitroethylene (0.15 g.) and acetonitrile (5 ml.) was heated under reflux for 6 hours and then left at room temperature for 18 hours. The yellow crystalline precipitate was collected to give 1-(2-[4-(2-[2,2,2-trifluoroethyl]guanidino)pyrimid-2-ylmethylthio]ethylamino)-1-methylamino-2-nitroethylene (0.26 g.), m.p. 154°–157° after recrystallisation from ethanol.

By a similar process using 2,2-biscyano-1-methylamino-1-methylthioethylene in place of 1-methylamino-1-methylthio-2-nitroethylene there was obtained 1-(2-[4-(2-[2,2,2-trifluoroethyl]guanidino)-pyrimid-2-ylmethylthio]ethylamino)-2,2-biscyano-1-methylaminoethylene, m.p. 173°–174°.

EXAMPLE 23

A solution of 4-[2-(2,2,2-trifluoroethyl)guanidino]-2-[(2-aminoethyl)thiomethyl]pyrimidine (0.33 g.) and dimethyl(cyanoimido)dithiocarbonate (0.17 g.) in acetonitrile was left at room temperature for 18 hours and then evaporated to dryness. The residue was dissolved in ethanol (5 ml.), the solution treated with 99% hydrazine hydrate (0.2 ml.), the mixture allowed to stand at room temperature for 0.5 hours and then evaporated to dryness. The residue was triturated with water and filtered to give 3-amino-5-(2-[4-(2-[2,2,2-trifluoroethyl]guanidino)pyrimid-2-ylmethylthio]ethylamino)-1H-1,2,4-triazole (0.17 g.), m.p. 199°–201° after recrystallisation from a mixture of methanol and acetonitrile.

EXAMPLE 24

A solution of 4-[2-(2,2,2-trifluoroethyl)guanidino]-2-[(2-aminoethyl)thiomethyl]pyrimidine (0.15 g.) and dimethyl(methanesulphonylimido)dithiocarbonate (0.1 g.) in acetonitrile (2 ml.) was left at room temperature for 4 hours and then evaporated to dryness. The residue was dissolved in 33% w/v methylamine in ethanol and the solution left at room temperature for 18 hours and then evaporated to dryness. The residue was purified by preparative thin layer chromatography using chloroform/methanol/ammonia 8:2:0.2 v/v/v as developing solvent to give 4-[2-(2,2,2-trifluoroethyl)guanidino]-2-[2-(2-methanesulphonyl-3-methylguanidino)ethylthiomethyl]pyrimidine (0.09 g.) characterised as the hydrogen maleate, m.p. 148°–149° after recrystallisation from acetonitrile.

EXAMPLE 25

A mixture of 4-amino-2-[2-(2-cyano-3-methylguanidino)ethylthiomethyl]pyrimidine (0.5 g.), 2,2,2-trifluoroethylisothiocyanate (0.55 g.) and pyridine (10 ml.) was heated at 70° for 18 hours and then evaporated to dryness. The residue was dissolved in ethyl acetate and the solution washed with 2N aqueous acetic acid, dried and evaporated to dryness. The residue was dissolved in ethanolic ammonia (15 ml.), treated with yellow mercuric oxide (0.4 g.) and the mixture stirred at room temperature for 4 hours. The mixture was filtered and the filtrate evaporated to dryness. The residue was purified by preparative thin layer chromatography using ethyl acetate/methanol/ammonia 6:1:0.5 v/v/v as developing solvent to give 4-[2-(2,2,2-trifluoroethyl)guanidino]-2-[2-(3-cyano-2-methylguanidino)ethylthiomethyl]pyrimidine (0.2 g.) characterised as the hydrogen maleate, m.p. 111°–114° (decomp.) after recrystallisation from acetonitrile.

The 4-amino-2-[2-(2-cyano-3-methylguanidino)ethylthiomethyl]pyrimidine used as starting material may be obtained as follows:

2-Aminoethanethiol hydrochloride (2.02 g.) and 4-amino-2-chloromethylpyrimidine hydrogen maleate (2.3 g.) were added to a solution of sodium (1.23 g.) in methanol (25 ml.) and the mixture stirred at room temperature for 18 hours and then evaporated to dryness. The residue was dissolved in water, and the solution extracted four times with ethyl acetate and the combined ethyl acetate extracts dried and evaporated to dryness. The residue was dissolved in acetonitrile (6 ml.), the solution treated with dimethyl(cyanoimido)dithiocarbonate (1.04 g.) and the mixture left at room temperature for 18 hours. The mixture was filtered to give 4-amino-2-[2-(3-cyano-2-methylisothioureido)ethylthiomethyl]pyrimidine (0.86 g.), m.p. 112°–114°.

A solution of 4-amino-2-[2-(3-cyano-2-methylisothioureido)ethylthiomethyl]pyrimidine (0.75 g.) in 33% w/v methylamine in ethanol (15 ml.) was left at room temperature for 18 hours. The solution was concentrated to 5 ml., cooled in ice, and the crystalline precipitate collected to give 4-amino-2-[2-(2-cyano-3-methylguanidino)ethylthiomethyl]pyrimidine (0.52 g.), m.p. 189°–190°.

EXAMPLE 26

A mixture of 4-[2-(2,2,2-trifluoroethyl)guanidino]-2-(4-aminobutyl)pyrimidine (0.15 g.), 1-methyl-3-trifluoromethanesulphonylthiourea (0.11 g.), ethanol (10 ml.) and yellow mercuric oxide (0.22 g.) was stirred at room temperature for 18 hours. The mixture was filtered and the filtrate evaporated to dryness. The residue was dissolved in ethyl acetate and the solution added to a solution of maleic acid in acetone. The precipitated solid (130 mg.) was collected and recrystallised from ethyl acetate to give 4-[2-(2,2,2-trifluoroethyl)guanidino]-2-[4-(3-methyl-2-trifluoromethanesulphonylguanidino)butyl]pyrimidine hydrogen maleate, m.p. 156°–157°.

The 1-methyl-3-trifluoromethanesulphonylthiourea used as starting material may be obtained as follows:

A solution of methylisothiocyanate (0.21 g.) in acetone (10 ml.) was added to a solution of trifluoromethanesulphonamide (0.45 g.) and sodium hydroxide (0.12 g.) in water (5 ml.), the mixture stirred at 60° for 18 hours and then evaporated to dryness. The residue was dissolved in water and the solution washed with ethyl acetate and then adjusted to pH 1 with concentrated hydrochloric acid. The mixture was treated with charcoal and filtered and the filtrate extracted with ethyl acetate. The combined ethyl acetate extracts were dried and evaporated to dryness and the residue recrystallised from petroleum ether (b.p. 60°–80°) to give 1-methyl-3-trifluoromethanesulphonylthiourea (0.27 g.), m.p. 88°–90°.

EXAMPLE 27

Dimethyl(cyanoimido)dithiocarbonate (0.08 g.) was added to a solution of 4-[2-(2,2,2-trifluoroethyl)guanidino]-2-(4-aminobutylthio)pyrimidine (0.17 g.) in acetonitrile (2 ml.) and the solution left at room temperature for 18 hours and then evaporated to dryness to give 4-[2-(2,2,2-trifluoroethyl)guanidino]-2-[4-(3-cyano-2-methylisothioureido)butylthio]pyrimidine, characterised as the hydrogen maleate m.p. 181°–183°.

The 4-[2-(2,2,2-trifluoroethyl)guanidino]-2-[4-aminobutylthio]pyrimidine used as starting material may be prepared as follows:

A mixture of 2-thiocytosine (0.25 g.), 1,5-diazabicyclo[5,4,0]undec-5-ene (0.33 g.), ethanol (10 ml.) and N-(4-bromobutyl)phthalimide (0.62 g.) was stirred at room temperature for 18 hours and then evaporated to dryness. The residue was partitioned between water and ethyl acetate and the ethyl acetate phase was dried and evaporated to dryness. The residue was recrystallised from acetonitrile to give 4-amino-2-(4-phthalimidobutylthio)pyrimidine (0.56 g.), m.p. 164°–167°.

A mixture of 4-amino-2-(4-phthalimidobutylthio)pyrimidine (0.49 g.), acetonitrile (5 ml.) and 2,2,2-trifluoroethylisothiocyanate (0.28 g.) was stirred at 70° for 48 hours. A further 0.28 g. of 2,2,2-trifluoroethylisothiocyanate was added and the mixture stirred at 70° for 48 hours. The reaction mixture was cooled and filtered, the residue stirred with N aqueous acetic acid and the undissolved solid collected to give 4-[3-(2,2,2-trifluoroethyl)thioureido]-2-(4-phthalimidobutylthio)pyrimidine (0.49 g.), m.p. 201°–202° after recrystallisation from a mixture of ethanol and dimethylformamide.

A mixture of 4-[3-(2,2,2-trifluoroethyl)thioureido]-2-(4-phthalimidobutyl)pyrimidine (0.45 g.), dimethylformamide (20 ml.), saturated ethanolic ammonia (2 ml.) and yellow mercuric oxide (0.32 g.) was stirred at room temperature for 5 hours, filtered and the filtrate evaporated to dryness. A suspension of the residue (0.35 g.) in ethanol (20 ml.) was treated with 99% hydrazine hydrate (1 ml.) and the mixture heated under reflux for 1 hour and then evaporated to dryness. The residue was stirred with 2N hydrochloric acid and filtered, and the filtrate basified with 17N NaOH and then extracted four times with ether. The combined ether extracts were dried and evaporated to dryness to give 4-[2-(2,2,2-trifluoroethyl)guanidino]-2-(4-aminobutylthio)pyrimidine (0.17 g.) which was used without further purification.

EXAMPLE 28

A solution of 4-[2-(2,2,2-trifluoroethyl)guanidino]-2-[4-(3-cyano-2-methylisothioureido)butylthio]pyrimidine (0.17 g.) in 33% w/v methylamine in ethanol was left at room temperature for 18 hours and then evaporated to dryness. The residue was triturated with ether and the insoluble solid collected and recrystallised from ethyl acetate to give 4-[2-(2,2,2-trifluoroethyl)-guanidino]-2-[4-(2-cyano-3-methylguanidino)butylthio]pyrimidine, m.p. 179°–180°.

EXAMPLE 29

A solution of 4-[2-(2,2,2-trifluoroethyl)guanidino]-2-(3-aminopropylthio)pyrimidine (0.31 g.) in acetonitrile (5 ml.) was treated with 1-methylamino-1-methylthio-2-nitroethylene (0.15 g.) and the mixture heated under reflux for 18 hours. The hot solution was filtered and cooled and the solid which crystallised was collected and recrystallised from ethanol to give 1-[3-(4-[2-(2,2,2-trifluoroethyl)guanidino]pyrimid-2-ylthio)-propylamino]-1-methylamino-2-nitroethylene (0.11 g.), m.p. 189°–191°.

EXAMPLE 30

Dimethyl(methanesulphonylimido)dithiocarbonate (0.4 g.) was added to a solution of 4-[2-(2,2,2-trifluoroethyl)guanidino]-2-(3-aminopropylthio)pyrimidine (0.62 g.) in ethanol (10 ml.) and the solution left at room temperature for 18 hours and then filtered. The filtrate was evaporated to dryness, the residue dissolved in 33% w/v methylamine in ethanol (10 ml.), the solution left at room temperature for 18 hours and then evaporated to dryness. The residue was partitioned between water and ethyl acetate, and the ethyl acetate phase was separated, dried and evaporated to dryness. A solution of the residue in ethyl acetate was added to a solution of maleic acid in acetone and the crystalline precipitate collected to give 4-[2-(2,2,2-trifluoroethyl)guanidino]-2-[3-(2-methanesulphonyl-3-methylguanidino)propylthio]pyrimidine hydrogen maleate (0.8 g.), m.p. 162°–164°.

EXAMPLE 31

A mixture of 2,4-diamino-6-[5-(2-methanesulphonyl-3-methylguanidino)pentyl]-1,3,5-triazine (0.4 g.), 2,2,2-trifluoroethylisothiocyanate (0.4 g.) and dimethylformamide (0.5 ml.) was heated at 120° for 1 hour and then at 60° for 18 hours. The mixture was evaporated to dryness, the residue partitioned between water and ethyl acetate, and the ethyl phase was separated, dried, and evaporated to dryness. The residue was dissolved in saturated ethanolic ammonia (10 ml.) and the solution treated with yellow mercuric oxide (0.5 g.). The mixture was stirred at room temperature for 18 hours, filtered and the filtrate evaporated to dryness. The residue was purified by chromatography using ethyl acetate/methanol/ammonia 6:1:0.5 v/v/v as developing solvent to give 2-amino-4-[2-(2,2,2-trifluoroethyl)guanidino]-6-[5-(2-methanesulphonyl-3-methylguanidino)pentyl]-1,3,5-triazine (0.07 g.) characterised as the bishydrogen maleate, m.p. 131°–133° after recrystallisation from acetone.

The 2,4-diamino-6-[5-(2-methanesulphonyl-3-methylguanidino)pentyl]-1,3,5-triazine used as starting material in the above process may be prepared as follows:

A mixture of biguanide (1.05 g.), 4,5,6,7-tetrahydro-2-methoxy-3H-azepine (1.27 g.) and ethanol (50 ml.) was heated under reflux for 18 hours, cooled and the solid that crystallised was collected to give 2,4-diamino-6-(5-aminopentyl)-1,3,5-triazine which was used without further purification.

2,4-Diamino-6-(5-aminopentyl)-1,3,5-triazine (0.39 g.) was added to a solution of dimethyl(methanesulphonylimido)dithiocarbonate (0.4 g.) in methanol (5 ml.) and the solution left at room temperature for 2 hours. The solution was treated with 33% w/v methylamine in ethanol (5 ml.) and the solution stirred at room temperature for 24 hours. The crystalline solid which had separated was collected to give 2,4-diamino-6-[5-(2-methanesulphonyl-3-methylguanidino)pentyl]-1,3,5-triazine, m.p. 194°–195°.

EXAMPLE 32

Dimethyl(cyanoimido)dithiocarbonate (0.12 g.) was added to a solution of 2-[2-(2,2,2-trifluoroethyl)-guanidino]-6-(2-aminoethylthiomethyl)pyridine (0.23 g.) in acetonitrile (5 ml.) and the solution left at room temperature for 18 hours and then evaporated to dryness. The residue was dissolved in 33% w/v methylamine in ethanol (5 ml.) and the solution left at room temperature for 18 hours and then evaporated to dryness. The residue was purified by preparative thin layer chromatography using ethyl acetate/methanol/ammonia 6:1:0.5 v/v/v as the developing solvent to give 2-[2-(2,2,2-trifluoroethyl)guanidino]-6-[2-(2-cyano-3-methylguanidino)ethylthiomethyl]pyridine (0.12 g.) characterised as the hydrogen maleate, m.p. 137°–140° after recrystallisation from acetone.

The 2-[2-(2,2,2-trifluoroethyl)guanidino]-6-(2-aminoethylthiomethyl)pyridine used as starting material in the above process may be prepared as follows:

A mixture of 6-aminopyridine-2-carboxylic acid (5.0 g.) and a 1.35M solution of borane in tetrahydrofuran (100 ml.) was stirred under argon at reflux for 48 hours. The mixture was cooled and treated with 2N NaOH (50 ml.) and the mixture stirred at room temperature for 18 hours. The aqueous phase was saturated with sodium chloride and the organic phase separated. The aqueous phase was extracted twice with ethyl acetate and the ethyl acetate extracts combined with the tetrahydrofuran solution and the whole evaporated to dryness. The residue was dissolved in ethyl acetate (100 ml.) and the solution washed with saturated aqueous sodium chloride solution (5 ml.) and then dried and evaporated to dryness to give crude 2-amino-6-hydroxymethylpyridine (2.3 g.) which was used without further purification.

2,2,2-Trifluoroethylisothiocyanate (2.82 g.) was added to a solution of 2-amino-6-hydroxymethylpyridine (2.1 g.) in acetonitrile (20 ml.) and the solution kept at room temperature for 18 hours and then evaporated to dryness. The residue was partitioned between ethyl acetate and water and the ethyl acetate phase separated, dried and evaporated to dryness. The residue was recrystallised from ethanol to give 2-[3-(2,2,2-trifluoroethyl)thioureido]-6-[N-(2,2,2-trifluoroethyl)thiocarbamoyloxymethyl]pyridine (0.8 g.), m.p. 173°–175°.

A mixture of 2-[3-(2,2,2-trifluoroethyl)thioureido]-6-[N-(2,2,2-trifluoroethyl)thiocarbamoyloxymethyl]pyridine (0.73 g.), dimethylformamide (20 ml.), saturated ethanolic ammonia (5 ml.) and yellow mercuric oxide was stirred at room temperature for 18 hours. The mixture was filtered and the filtrate evaporated to dryness.

The residue was dissolved in concentrated aqueous ammonia (20 ml.), the solution heated at 90° for 2 hours, and then evaporated to dryness. The residue was partitioned between N aqueous acetic acid and ether, and the aqueous phase separated and basified with 17N NaOH. The mixture was extracted with ethyl acetate and the ethyl acetate extract dried and evaporated to dryness to give 2-[2-(2,2,2-trifluoroethyl)guanidino]-6-hydroxymethylpyridine which was used without further purification.

Thionyl chloride (0.2 ml.) was added to a solution of 2-[2-(2,2,2-trifluoroethyl)guanidino]-6-hydroxymethylpyridine (0.2 g.) in tetrahydrofuran (5 ml.) and the mixture was left at room temperature for 0.5 hours and then evaporated to dryness. A solution of the residue in methanol (2 ml.) was added to a mixture of 2-aminoethanethiol hydrochloride (0.14 g.), sodium methoxide (0.22 g.) and methanol (15 ml.), the mixture stirred at room temperature for 18 hours and then evaporated to dryness. The residue was partitioned between N aqueous acetic acid and ether, and the aqueous phase separated and basified with 17N NaOH. The mixture was extracted three times with ether to give 2-[2-(2,2,2-trifluoroethyl)guanidino]-6-[2-aminoethylthiomethyl]-pyridine which was used without further purification.

EXAMPLE 33

A solution of bromine (0.064 g.) in methylene chloride (2 ml.) was added dropwise over 15 minutes to a stirred solution of 4-[2-(2,2,2-trifluoroethyl)guanidino]-2-[3-(2-methylsulphonyl-3-methylguanidino)propylthio]pyrimidine (0.176 g.) and pyridine (0.2 ml.) in methylene chloride (10 ml.), and the mixture stirred at room temperature for one hour. The solution was evaporated to dryness, and the residue purified by preparation thin layer chromatography using ethyl acetate/methanol/ammonia 6:1:0.5 v/v/v as developing solvent to give 5-bromo-4-[2-(2,2,2-trifluoroethyl)guanidino]-2-[3-(2-methylsulphonyl-3-methylguanidino)propylthio]-pyrimidine (0.12 g.), m.p. 166°-167° after recrystallisation from ethanol.

EXAMPLE 34

A mixture of 4-[2-(2,2,2-trifluoroethyl)guanidino]-2-(3-aminopropylamino)pyrimidine (0.097 g.), methanol (2 ml.) and 3-nitro-2-methylisothiourea (0.045 g.) was stirred at room temperature for 3 hours and then evaporated to dryness. The residue was stirred with a mixture of ether and water, and the insoluble material collected and dissolved in ethyl acetate. The solution was added to a solution of maleic acid in acetone, and the crystalline precipitate collected to give 4-[2-(2,2,2-trifluoroethyl)guanidino]-2-[3-(2-nitroguanidino)propylamino]-pyrimidine bis hydrogen maleate (0.09 g.), m.p. 173°-174°.

The 4-[2-(2,2,2-trifluoroethyl)guanidino]-2-(3-aminopropylamino)pyrimidine used as starting material in the above process may be obtained as follows:

A mixture of 4-amino-2-methylthiopyrimidine (2.1 g.), 2,2,2-trifluoroethylisothiocyanate (2.8 g.) and acetonitrile (5 ml.) was stirred at 70° for 72 hours and then cooled, and the solid that crystallised was collected to give 4-[3-(2,2,2-trifluoroethyl)thioureido]-2-methylthiopyrimidine (2.15 g.) which was used without further purification.

A mixture of 4-[3-(2,2,2-trifluoroethyl)thioureido]-2-methylthiopyrimidine (2.15 g.), methanol (100 ml.), saturated ethanolic ammonia (10 ml.) and yellow mercuric oxide (4.3 g.) was stirred at room temperature for 2 hours and then filtered. The filtrate was evaporated to dryness and the residue recrystallised from ethanol to give 4-[2-(2,2,2-trifluoroethyl)guanidino]-2-methylthiopyrimidine (1.5 g.) m.p. 201°-202°.

3-Chloroperbenzoic acid (0.8 g.) was added to a solution of 4-[2-(2,2,2-trifluoroethyl)guanidino]-2-methylthiopyrimidine (0.5 g.) in ethanol (50 ml.) and the solution left at room temperature for 18 hours and then evaporated to dryness. The residue was dissolved in ethyl acetate, the solution washed with aqueous potassium carbonate solution and then dried and evaporated to dryness to give 4-[2-(2,2,2-trifluoroethyl)guanidino]-2-methylsulphinylpyrimidine (0.5 g.) which was used without further purification.

A mixture of 4-[2-(2,2,2-trifluoroethyl)guanidino]-2-methylsulphinylpyrimidine (0.3 g.) and 1,3-diaminopropane (1 ml.) was heated to 90° for 3 hours. The mixture was evaporated to dryness and the residue taken up in 2N aqueous acetic acid. The solution was washed with ether, basified with 17N NaOH and the mixture extracted five times with ether. The combined ether extracts were dried and evaporated to dryness to give 4-[2-(2,2,2-trifluoroethyl)guanidino]-2-(3-aminopropylamino)pyrimidine (0.27 g.) which was characterised as the tris hydrogen maleate, m.p. 159° after recrystallisation from acetone.

EXAMPLE 35

A mixture of 4-[2-(2,2,2-trifluoroethyl)guanidino]-2-(3-aminopropylamino)pyrimidine (0.15 g.), dimethyl(methanesulphonylimido)dithiocarbonate (0.1 g.) and methanol (2 ml.) was left at room temperature for 3 hours. A 33% w/v solution of methylamine in ethanol (5 ml.) was added and the mixture left at room temperature for 18 hours and then evaporated to dryness. The residue was dissolved in acetone, the solution added to a solution of maleic acid in acetone and the crystalline precipitate collected to give 4-[2-(2,2,2-trifluoroethyl)-guanidino]-2-[3-(2-methanesulphonyl-3-methylguanidino)aminopropylamino]pyrimidine bis hydrogen maleate (0.14 g.), m.p. 160°-161°.

EXAMPLE 36

A solution of 4-[2-(2,2,2-trifluoroethyl)guanidino]-2-(3-aminopropyloxy)pyrimidine (0.07 g.) and dimethyl(cyanoimido)dithiocarbonate (0.035 g.) in ethanol was left at room temperature for 2 hours. A 33% w/v solution of methylamino in ethanol (5 ml.) was added, the mixture left at room temperature for 18 hours and then evaporated to dryness. The residue was dissolved in ethyl acetate and the solution added to a solution of maleic acid in acetone, and the crystalline precipitate collected to give 4-[2-(2,2,2-trifluoroethyl)guanidino]-2-[3-(2-cyano-3-methylguanidino)propyloxy]pyrimidine hydrogen maleate (0.085 g.), m.p. 146°-148°.

The 4-[2-(2,2,2-trifluoroethyl)guanidino]-2-(3-aminopropyloxy)pyrimidine used as starting material may be obtained as follows:

4-[2-(2,2,2-Trifluoroethyl)guanidino]-2-methylsulphonylpyrimidine (0.15 g.) was added to a mixture of 3-aminopropanol (0.075 g.), t-butanol (5 ml.) and a 50% w/w dispersion of sodium hydride in mineral oil (0.05 g.) which was stirred under an argon atmosphere. The mixture was stirred at room temperature for 2 hours, heated under reflux for 4 hours and then evaporated to dryness. The residue was partitioned between 2N aqueous acetic acid and ether, and the aqueous phase basified with 17N NaOH and extracted three times with ether. The combined ether extracts were dried and evaporated to dryness to give 4-[2-(2,2,2-trifluoroethyl)guanidino]-2-(3-aminopropyloxy)pyrimidine (0.07 g.) which was used without further purification.

EXAMPLE 37

A mixture of 4-[2-(2,2,2-trifluoroethyl)guanidino]-2-(3-aminopropylthio)pyrimidine (0.15 g.), 1-methanesulphonyl-3-(2,2,2-trifluoroethyl)thiourea (0.12 g.), ethanol (5 ml.) and yellow mercuric oxide (0.22 g.) was stirred at room temperature for 18 hours. The mixture was filtered, the filtrate evaporated to dryness and the residue was dissolved in acetonitrile. This solution was added to a solution of maleic acid in acetone and the precipitate collected and recrystallised from ethanol to give 4-[2-(2,2,2-trifluoroethyl)guanidino]-2-[3-(2-methanesulphonyl-3-[2,2,2-trifluoroethyl]guanidino)propylthio]pyrimidine hydrogen maleate (0.18 g.), m.p. 167°–168°.

The 1-methanesulphonyl-3-(2,2,2-trifluoroethyl)thiourea used as starting material may be obtained as follows:

A solution of 2,2,2-trifluoroethylisothiocyanate (1.4 g.) in acetone (20 ml.) was added to a solution of methanesulphonamide (0.95 g.) and sodium hydroxide (0.44 g.) in water (10 ml.) and the mixture stirred and heated under reflux for 18 hours, and then evaporated to dryness. The residue was dissolved in water and the solution washed with ethyl acetate and then acidified with concentrated hydrochloric acid. The mixture was extracted three times with ethyl acetate and the combined extracts dried and evaporated to dryness. The residue was triturated with acetonitrile and filtered and the filtrate evaporated to dryness. The residue was dissolved in ether, and the solution extracted with aqueous sodium bicarbonate solution. The extract was neutralised with N hydrochloric acid and the mixture extracted with ethyl acetate. The ethyl acetate extract was dried and evaporated to dryness to give 1-methanesulphonyl-3-(2,2,2-trifluoroethyl)thiourea (0.45 g.) which was used without further purification.

EXAMPLE 38

A mixture of 4-[2-(2,2,2-trifluoroethyl)guanidino]-2-[3-(3-cyano-2-methylisothioureido)propylthio]pyrimidine (0.2 g.), methanol (2 ml.) and ethanolamine (0.5 ml.) was stirred at room temperature for 3 days and then evaporated to dryness. Water was added to the residue, the mixture extracted with ethyl acetate and the ethyl acetate extract dried and evaporated to dryness. The residue was recrystallised from acetonitrile to give 4-[2-(2,2,2-trifluoroethyl)guanidino]-2-[3-(2-cyano-3-[2-hydroxyethyl]guanidino)propylthio]pyrimidine (0.1 g.), m.p. 114°–116°.

EXAMPLE 39

A mixture of 4-[2-(2,2,2-trifluoroethyl)-guanidino]-2-[3-(3-cyano-2-methylisothioureido)propylthio]pyrimidine (0.2 g.), N,N-diethylethylenediamine (0.5 ml.) and methanol (2 ml.) was heated under reflux for 24 hours and then evaporated to dryness. Water was added to the residue, the mixture extracted with ethyl acetate and the ethyl acetate extract dried and evaporated to dryness. The residue was purified by preparative thin layer chromatography using ethyl acetate/methanol/ammonia 6:1:0.5 v/v/v as developing solvent to give 4-[2-(2,2,2-trifluoroethyl)guanidino]-2-[3-(2-cyano-3-[2-diethylaminoethyl]guanidino)propylthio]pyrimidine (0.08 g.), characterised as the bis hydrogen maleate, m.p. 76°–80° after recrystallisation from acetone.

EXAMPLE 40

A mixture of 4-[2-(2,2,2-trifluoroethyl)guanidino]-2-[3-(3-cyano-2-methylisothioureido)propylthio]pyrimidine (0.34 g.) and ethylenediamine (0.5 g.) was stirred at room temperature for 4 hours and then evaporated to dryness. Water was added to the residue, the mixture extracted with ethyl acetate, and the ethyl acetate extract dried and evaporated to dryness. A solution of the residue in acetone was added to a solution of maleic acid in acetone, and the crystalline precipitate collected to give 4-[2-(2,2,2-trifluoroethyl)guanidino]-2-[3-(2-cyano-3-[2-aminoethyl]-guanidino)propylthio]pyrimidine bis hydrogen maleate, m.p. 173°–176°.

EXAMPLE 41

A mixture of 4-[2-(2,2,2-trifluoroethyl)-guanidino]-2-(2-aminoethyl)thiomethylpyrimidine (0.31 g.), methanol (5 ml.) and 1,2-dimethoxycyclobutene-3,4-dione (0.14 g.) was stirred at room temperature for 18 hours. A 33% w/v solution of methylamine in ethanol (5 ml.) was added and the mixture left at room temperature for 18 hours and then evaporated to dryness. The residue was purified by preparative thin layer chromatography using ethyl acetate/methanol/ammonia 6:1:0.5 v/v/v as developing solvent to give 1-(2-[4-(2-[2,2,2-trifluoroethyl]guanidino)pyrimid-2-yl-methylthio]ethylamino)-2-methylaminocyclobutene-3,4-dione (0.16 g.) characterised as the hydrogen maleate, m.p. 178°–184° after recrystallisation from a mixture of methanol and acetonitrile.

EXAMPLE 42

A mixture of 4-[2-(2,2,2-trifluoroethyl)guanidino]-2-(2-aminoethylthio)pyrimidine (0.25 g.), acetonitrile (5 ml.) and dimethyl (cyanoimido)dithiocarbonate (0.12 g.) was left at room temperature for 24 hours and then evaporated to dryness. The residue was dissolved in a 33% w/v solution of methylamine in ethanol, and the solution left at room temperature for 24 hours and then evaporated to dryness. The residue was recrystallised from ethanol to give 4-[2-(2,2,2-trifluoroethyl)-guanidino]-2-[2-(2-cyano-3-methylguanidino)ethylthio]pyrimidine, m.p. 218°–221°.

The 4-[2-(2,2,2-trifluoroethyl)guanidino]-2-(2-aminoethylthio)pyrimidine used as starting material may be obtained as follows:

A mixture of 2-thiocytosine (0.51 g.), dimethylformamide (5 ml.), N-(2-bromoethyl)phthalimide (1.12 g.) and 1,8-diazabicyclo[5,4,0]undec-5-ene (0.67 g.) was stirred at room temperature for 6 hours and then evaporated to dryness. The residue was stirred with a mixture of water and ethyl acetate and the unsoluble material collected to give 4-amino-2-(2-phthalimidoethylthio)pyrimidine which was used without further purification.

A mixture of 4-amino-2-(2-phthalimidoethylthio)pyrimidine (0.8 g.), 2,2,2-trifluoroethylisothiocyanate (0.56 g.) and dimethyl formamide (2 ml.) was stirred at 70° for 72 hours. The mixture was cooled, diluted with acetonitrile and filtered to give 4-[3-(2,2,2-trifluoroethyl)thioureido]-2-(2-phthalimidoethylthio)pyrimidine (0.7 g.), m.p. 238°–241°.

A mixture of 4-[3-(2,2,2-trifluoroethyl)thioureido]-2-(2-phthalimidoethylthio)pyrimidine (0.65 g.), dimethylformamide (10 ml.), ethanolic ammonia solution (5 ml.) and yellow mercuric oxide was stirred at room temperature for 4 hours. The mixture was filtered and the filtrate evaporated to dryness to give 4-[2-(2,2,2-trifluoroethyl)guanidino]-2-(2-phthalimidoethylthio)-pyrimidine (0.62 g.), m.p. 192°–195°.

A mixture of 4-[2-(2,2,2-trifluoroethyl)guanidino]-2-(2-phthalimidoethylthio)pyrimidine (0.6 g.) ethanol (20 ml.) and 99% hydrazine hydrate (0.5 ml.) was heated under reflux for 1 hour and then evaporated to dryness. The residue was stirred with N hydrochloric acid and the mixture filtered. The filtrate was basified with 17N NaOH and the mixture extracted three times with ether. The combined ether extracts were dried and then evaporated to dryness to give 4-[2-(2,2,2-trifluoroethyl)-guanidino]-2-(2-aminoethylthio)pyrimidine (0.25 g.) which was used without further purification.

EXAMPLE 43

A mixture of 3-[2-(2,2,2-trifluoroethyl)guanidino]-1-(3-aminopropyl)pyrazole (0.13 g.), dimethyl (methanesulphonylimido)dithiocarbonate (0.1 g.) and methanol (2 ml.) was left at room temperature for 3 hours. A 33% w/v solution of methylamine in ethanol (5 ml.) was added and the mixture left at room temperature for 18 hours and then evaporated to dryness. A solution of the residue in ethyl acetate was added to a solution of oxalic acid in ethyl acetate, and the precipitate collected and recrystallised from ethanol to give 3-[2-(2,2,2-trifluoroethyl)guanidino]-1-[3-(2-methanesulphonyl-3-methylguanidino)propyl]pyrazole hydrogen oxalate, m.p. 162°–163°.

The 3-[2-(2,2,2-trifluoroethyl)guanidino]-1-(3-aminopropyl)pyrazole used as starting material may be obtained as follows:

2,2,2-Trifluoroethylisothiocyanate (3.4 g.) was added to a solution of 3-amino-1-(2-cyanoethyl)-pyrazole (2.72 g.) in acetonitrile (10 ml.) and the solution left at room temperature for 18 hours. The mixture was was evaporated to dryness and the residue recrystallised from ethanol to give 3-[3-(2,2,2-trifluoroethyl)thioureido]-1-(2-cyanoethyl)pyrazole, m.p. 164°–165°.

A mixture of 3-[3-(2,2,2-trifluoroethyl)thioureido]-1-(2-cyanoethyl)pyrazole (2.8 g.), yellow mercuric oxide (4.0 g.), methanol (100 ml.) and saturated ethanolic ammonia solution (10 ml.) was stirred at room temperature for 2 hours and then filtered. The filtrate was evaporated to dryness and the residue partitioned between ether and water. The ether phase was dried and evaporated to give 3-[2-(2,2,2-trifluoroethyl)guanidino]-1-(2-cyanoethyl)pyrazole characterised as the hydrogen maleate, m.p. 141°–142° after recrystallisation from acetone.

A mixture of 3-[2-(2,2,2-trifluoroethyl)guanidino]-1-(2-cyanoethyl)pyrazole (0.32 g.), saturated ethanolic ammonia (10 ml.) and Raney nickel (0.2 g.) was stirred vigorously under an atmosphere of hydrogen at room temperature and atmospheric pressure for 3 hours. The mixture was filtered and the filtrate evaporated to dryness to give 3-[2-(2,2,2-trifluoroethyl)guanidino]-1-(3-aminopropyl)pyrazole which was used without further purification.

EXAMPLE 44

A mixture of 4-[2-(2,2,2-trifluoroethyl)guanidino]-2-(3-aminopropylthio)pyrimidine (0.15 g.), 1,3-bis-(2,2,2-trifluoroethyl)thiourea (0.12 g.), yellow mercuric oxide (0.22 g.) and ethanol (20 ml.) was stirred at room temperature for 0.5 hours and then filtered and the filtrate evaporated to dryness. A solution of the residue in acetone was added to a solution of maleic acid in acetone and the crystalline precipitate collected to give 4-[2-(2,2,2-trifluoroethyl)guanidino]-2-[3-(2,3-bis[2,2,2-trifluoroethyl]guanidino)propylthio]pyrimidine bis hydrogen maleate (0.1 g.) m.p. 134°–136°.

The 1,3-di(2,2,2-trifluoroethyl)thiourea used as starting material may be obtained as follows:

2,2,2-Trifluoroethylisothiocyanate (2.12 g.) was added to a mixture of 2,2,2-trifluoroethylamine hydrochloride (1.36 g.), triethylamine (1.01 g.) and acetonitrile (10 ml.), and the mixture stirred at room temperature for 4 hours and then evaporated to dryness. The residue was partitioned between water and ethyl acetate, and the ethyl acetate phase was dried and evaporated to dryness. The residue was recrystallised from a mixture of acetone and light petroleum ether (b.p. 60°–80°) to give 1,3-di(2,2,2-trifluoroethyl)thiourea, m.p. 152°–153°.

EXAMPLE 45

To a stirred mixture of 2-[2-(2,2,2-trifluoroethyl)-guanidino]-4-(4-aminobutyl)-5-methylthiazole dihydrochloride (0.31 g.) and triethylamine (0.22 ml.) in ethanol (2 ml.) was added dimethyl (methylsulphonylimido)dithiocarbonate (0.16 g.). The resulting colourless solution was stirred at ambient temperature overnight and then evaporated to dryness to give a crude oil which was purified by chromatography using CHCl$_3$/methanol 9.75:0.25 v/v as solvent to give 2-[2-(2,2,2-trifluoroethyl)guanidino]-4-[4-(3-methylsulphonyl-2-methylisothioureido)butyl]-5-methylthiazole as an oil.

To the 2-[2-(2,2,2-trifluoroethyl)guanidino]-4-[4-(3-methylsulphonyl-2-methylisothioureido)butyl]-5-methylthiazole was added a 30% w/v ethanolic solution of methylamine (5 ml.) and the mixture allowed to stand overnight at ambient temperature. It was then evaporated to dryness and 2-[2-(2,2,2-trifluoroethyl)-guanidino]-4-[4-(2-methylsulphonyl-3-methylguanidino)butyl]-5-methylthiazole (0.17 g.) was isolated as the maleate salt from acetone, m.p. 165°–166°.

The 2-[2-(2,2,2-trifluoroethyl)guanidino]-4-(4-aminobutyl)-5-methylthiazole used as starting material may be prepared as follows:

A mixture of N-(6-chloro-5-oxoheptyl)phthalimide (0.7 g.), 2,2,2-trifluoroethylamidinothiourea (0.48 g.) and ethanol (10 ml.) was heated under reflux for 15 minutes and allowed to cool to ambient temperature. The resulting colourless solution was allowed to stand in an open vessel for 6 days, whereupon white cyrstalline rosettes of 2-[2-(2,2,2-trifluoroethyl)guanidino]-4-(4-phthalimidobutyl)-5-methylthiazole hydrochloride (0.60 g.) precipitated.

To a mixture of 2-[2-(2,2,2-trifluoroethyl)guanidino]-4-(4-phthalimidobutyl)-5-methylthiazole hydrochloride (0.60 g.) in water (2 ml.) and ethanol (2 ml.) was added sodium hydroxide pellets (0.2 g.). The resulting yellow solution was heated on a steam bath for 10 minutes and then allowed to cool to ambient temperature. The reaction mixture was adjusted to pH3 by addition of 2N hydrochloric acid and then reheated on a steam bath for 1 hour. After cooling to ambient temperature the mixture was extracted three times with equal volumes of ethyl acetate. The aqueous layer was evaporated to dryness, azeotroped twice with toluene, the residue dissolved in methanol (10 ml.) and the solution filtered. The filtrate was evaporated to dryness to give 2-[2-

(2,2,2-trifluoroethyl)guanidino]-4-(4-aminobutyl)-5-methylthiazole dihydrochloride (0.31 g.) as an oil which was used without further purification.

EXAMPLE 46

Trifluoroethylisothiocyanate (0.2 g.) in acetonitrile (6 ml.) was added to a solution of 2-[2-(2,2,2-trifluoroethyl)guanidino]-4-(4-aminobutyl)thiazole (0.5 g.) in acetonitrile (10 ml.), and the mixture was allowed to stand at room temperature for 2 hours. The residue obtained on evaporation of the solvent was subjected to preparative thin layer chromatography using chloroform/methanol/ammonia 85:15:0.5 v/v/v for development. The appropriate zone of the chromatogram was isolated and extracted with hot ethanol/chloroform 50:50 v/v (200 ml.). The residue was crystallised from ethyl acetate/light petroleum ether (b.p. 60°–80°) to give 2-[2-(2,2,2-trifluoroethyl)-guanidino]-4-(4-[3-(2,2,2-trifluoroethyl)-thioureido]butyl)-thiazole. The n.m.r. spectrum in $d_6$ dimethylsulphoxide using tetramethylsilane as internal standard ($\delta=0$) included the following resonances ($\delta$):4.05 (2H, multiplet); 4.35 (2H, multiplet); 6.36 (1H, singlet).

EXAMPLE 47

A solution of silver nitrate (0.4 g.) in dimethylformamide (2 ml.) was added to a solution of 2-[2-(2,2,2-trifluoroethyl)guanidino]-4-(4-[3-(2,2,2-trifluoroethyl)thioureido]butyl)thiazole (0.3 g.) in dimethylformamide (4 ml.) and ammonia (s.g. 0.88, 4 ml.). After standing for 0.5 hours at room temperature the solution was treated with excess gaseous hydrogen sulphide. Precipitated silver sulphide was filtered off and the filtrate evaporated to dryness. The residue was treated with water (15 ml.), basified with aqueous sodium hydroxide and extracted with ethyl acetate (2×30 ml.). Evaporation of the dried (magnesium sulphate) organic solution gave a red glass (0.25 g.) which was dissolved in acetone (1 ml.) and the solution treated with an excess of maleic acid in acetone. Addition of a little ether induced crystallisation of 2-[2-(2,2,2-trifluoroethyl)guanidino]-4-(4-[2-(2,2,2-trifluoroethyl)guanidino]butyl)thiazole dihydrogen maleate. The n.m.r. spectrum in $d_6$ dimethylsulphoxide using tetramethylsilane as internal standard ($\delta=0$) included the following resonances ($\delta$):4.05 (4H, multiplet); 6.1 (4H, singlet—maleic acid); 6.36 (1H, singlet).

EXAMPLE 48

To a solution containing 1-methanesulphonyl-3-(2,2,2-trifluoroethyl)thiourea (0.09 g.) and 2-[2-(2,2,2-trifluoroethyl)guanidino]-4-(4-aminobutyl)thiazole (0.13 g.) in dimethylformamide (4 ml.) was added a solution of silver nitrate (0.14 g.) in dimethylformamide (2 ml.). After allowing it to stand at room temperature for 3 hours the reaction mixture was treated with an excess of gaseous hydrogen sulphide and the precipitated silver sulphite filtered off. The residue obtained on evaporation of the filtrate was subjected to preparative thin layer chromatography using chloroform/methanol/ammonia 90:10:0.1 v/v/v for development. Isolation of the appropriate zone of the chromatogram and extraction with hot ethanol/chloroform 50:50 v/v (150 ml.) gave a yellow residue which on crystallisation from methanol afforded 2-[2-(2,2,2-trifluoroethyl)guanidino]-4-[2-(2-methylsulphonyl-3-[2,2,2-trifluoroethyl]-guanidino)ethylthiomethyl]thiazole which contained one mole of methanol of crystallisation. The n.m.r. spectrum in $d_6$ *dimethylsulphoxide containing a little $d_4$* acetic acid and using tetramethylsilane as internal standard ($\delta=0$) included the following resonances ($\delta$):2.8 (3H, singlet); 4.0 (2H, multiplet); 4.1 (2H, multiplet); 6.4 (1H, singlet).

EXAMPLE 49

A solution of 2-[2-(2,2,2-trifluoroethyl)guanidino]-4-(4-aminobutyl)thiazole (0.3 g.) in acetonitrile/pyridine 1:1 v/v (5 ml.) was treated with acetic anhydride (0.1 g.) and the mixture allowed to stand at room temperature for 72 hours. The residue obtained on evaporation of the solvent was subjected to preparative thin layer chromatography using ethyl acetate/methanol/water 6:1:1 v/v/v for development. Isolation of the appropriate region of the chromatogram and extraction with hot ethanol/chloroform 1:1 v/v (200 ml.) gave a residue which on treatment with ether/petroleum ether (b.p. 60°–80°) afforded 2-[2-(2,2,2-trifluoroethyl)guanidino]-4-(4-acetaminobutyl)thiazole. The n.m.r. spectrum in $d_6$ dimethylsulphoxide using tetramethylsilane as internal standard ($\delta=0$) included the following resonances ($\delta$):1.5 (4H, multiplet); 1.84 (3H, singlet); 3.1 (2H, multiplet); 4.1 (2H, multiplet); 6.4 (1H, singlet).

EXAMPLE 50

A mixture of 2-[2-(2,2,2-trifluoroethyl)guanidino]-4-(4-aminobutyl)thiazole (0.4 g.) and ethyl N-cyanoacetimidate (0.14 g.) in ethanol (3 ml.) was allowed to stand at room temperature for 6 hours. The residue obtained on evaporation of the solvent was subjected to preparative thin layer chromatography using ethyl acetate/methanol/water 12:2:1 v/v/v for development. Isolation of the appropriate zone of the chromatogram and extraction with hot ethanol/chloroform 1:1 v/v (200 ml.) gave a glass-like material which was dissolved in acetone (1.5 ml.) and treated with an excess of maleic acid in acetone. The crystalline precipitate was collected and washed with a little acetone and ether to give 2-[2-(2,2,2-trifluoroethyl)guanidino]-4-[4-(3-cyano-2-methylamidino)butyl-thiazole which contained 1.2 moles of maleic acid of crystallisation. The n.m.r. spectrum in $d_6$ dimethylsulphoxide using tetramethylsilane as internal standard ($\delta=0$) included the following resonances ($\delta$):1.6 (4H, multiplet); 2.22 (3H, singlet); 3.2 (2H, multiplet); 4.15 (2H, multiplet); 6.55 (1H, singlet).

EXAMPLE 51

To a solution of 2-[2-(2,2,2-trifluoroethyl)guanidino]-4-(5-aminopentyl)thiazole (0.5 g.) in ethanol (8 ml.) was added dimethyl (methylsulphonylimido)dithiocarbonate (0.35 g.). The mixture was allowed to stand at room temperature for 2 days, evaporated to dryness and the residue purified by preparative thin layer chromatography using methanol/chloroform 1:9 v/v for development. The appropriate band was extracted with ethanol/chloroform 1:1 v/v (200 ml.) and the solution evaporated to dryness. The residue in ethanol (3 ml.) was treated with ethanolic methylamine 33% (w/v, 30 ml.) and the mixture allowed to stand overnight at room temperature. The solution was then evaporated to dryness and the residue in acetone treated with excess maleic acid to give 2-[2-(2,2,2-trifluoroethyl)guanidino]-4-[5-(3-methylsulphonyl-2-methylguanidino)pentyl]-thiazole dihydrogen maleate. The n.m.r. spectrum in $d_6$ dimethylsulphoxide using tetramethylsilane as internal standard ($\delta=0$) included the following reasonances (δ):1.5 (multiplet, 6H); 2.75 (doublet, 3H); 2.85 (singlet, 3H); 3.1 (quartet, 2H); 4.2 (quartet, 2H); 6.7 (singlet, 1H).

The 2-[2-(2,2,2-trifluoroethyl)guanidino]-4-(5-aminopentyl)thiazole used as starting material may be prepared in an analogous manner to that described for 2-[2-(2,2,2-trifluoroethyl)guanidino]-4-(4-aminobutyl)-thiazole in Example 6 but using N-(7-chloro-6-oxoheptyl)phthalimide as starting material in place of N-(6-chloro-5-oxohexyl)phthalimide.

EXAMPLE 52

A mixture of 2-[2-(2,2,2-trifluoroethyl)guanidino]-4-(5-aminopentyl)thiazole (0.6 g.) and 2-nitroamino-6-methyl-4-pyrimidone (0.36 g.) in pyridine (4 ml.) was heated under reflux for 4 hours. After this period the pyridine was removed by evaporation and the residue heated at 160° for 20 minutes. The material was then cooled and purified by thin layer chromatography using ethyl acetate/methanol/water 12:2:1 v/v/v as developing solvent. The appropriate band was extracted with chloroform/ethanol 1:1 v/v (200 ml.) and isolated by evaporation to dryness. The residue in acetone was then treated with excess maleic acid to precipitate 6-methyl-2-(5-[2-(2-[2,2,2-trifluoroethyl]guanidino)thiazol-4-yl]pentylamino)-pyrimid-4-one di(hydrogen maleate). The n.m.r. spectrum in $d_6$ dimethylsulphoxide using tetramethylsilane as internal reference ($\delta=0$) included the following resonances ($\delta$):1.6 (multiplet, 6H); 2.15 (singlet, 3H); 3.3 (multiplet, 2H); 4.2 (quartet 2H); 5.55 (singlet, 1H); 6.7 (singlet, 1H).

EXAMPLE 53

A mixture of 2-[2-(2,2,2-trifluoroethyl)guanidino]-4-(4-aminobutyl)thiazole (0.7 g.) and 2-nitroamino-5-methyl-4(3H)-pyrimidone (0.3 g.) was heated under reflux in pyridine (3 ml.) for 3.5 hours. The mixture was then evaporated to dryness and the residue purified by preparative thin layer chromatography using ethyl acetate/methanol/6:1:1 v/v/v for development. The appropriate band was extracted with chloroform/ethanol 1:1 v/v (200 ml.). Evaporation of the solvent to dryness gave a red gum which was treated in acetone with excess maleic acid to give 5-methyl-2-(4-[(-2-[2,2,2-trifluoroethyl]guanidino)thiazol-4-yl]butylamino)-pyrimid-4-one containing 1.75 equivalents of maleic acid. The n.m.r. of this compound in $d_6$ dimethylsulphoxide using tetramethylsilane as internal standard ($\delta=0$) included the following resonances ($\delta$):1.6 (multiplet, 4H); 1.8 (singlet, 3H); 3.3 (multiplet, 2H); 4.2 (quartet, 2H); 6.6 (singlet, 1H); 7.5 (singlet, 1H).

EXAMPLE 54

To 2-[2-(2,2,2-trifluoroethyl)guanidino]-4-(5-aminopentyl)thiazole (0.4 g.) in methanol (1.5 ml.) was added 1,2-dimethoxycyclobutene-3,4-dione (0.2 g.). After 2.5 hours at room temperature the mixture was evaporated to dryness, and the residue purified by preparative thin layer chromatography using methanol/chloroform 1:9 v/v as developing solvent. The appropriate band was isolated to give 1-[5-(2-[2-(2,2,2-trifluoroethyl)guanidino]thiazol-4-yl)pentylamino]-2-methoxycyclobutene-3,4-dione (0.22 g.) which was dissolved in propargylamine (1 g.) and the mixture allowed to stand at room temperature overnight. The mixture was then evaporated to dryness, and the residue purified by preparative thin layer chromatography using chloroform/methanol/aqueous ammonia 90:10:1 v/v/v as developing solvent. The product from this purification was treated in methanol/acetone with excess maleic acid and the resulting salt precipitated by the addition of diethyl ether to give 1-[5-(2-[2-(2,2,2-trifluoroethyl)guanidino]thiazol-4-yl)pentylamino]-2-propargylaminocyclobutene-3,4-dione hydrogen maleate. The n.m.r. spectrum in $d_6$ dimethylsulphoxide using tetramethylsilane as internal standard ($\delta=0$) included the following resonances ($\delta$):1.5 (multiplet, 6H); 3.3 (singlet, 1H); 3.5 (multiplet, 2H); 4.1 (quartet, 2H); 4.8 (quartet, 2H); 6.6 (singlet, 1H).

EXAMPLE 55

A mixture of 2-[2-(2,2,2-trifluoroethyl)guanidino]-4-(5-aminopentyl)thiazole (0.3 g.) and 1,2-dimethoxycyclobutene-3,4-dione (0.15 g.) in methanol (3 ml.) was allowed to stand at room temperature for 4 hours. Ethanolic methylamine (33% w/v, 20 ml.) was then added and the solution allowed to stand overnight. The mixture was evaporated to dryness and the residue purified by preparative thin layer chromatography using ethyl acetate/methanol/water 6:1:1 v/v/v as developing solvent to give 1-[5-(2-[2-(2,2,2-trifluoroethyl)guanidino]thiazol-4-yl)pentylamino]-2-methylaminocyclobutene-3,4-dione as a colourless gum (0.17 g.). The n.m.r. spectrum of the hydrogen maleate salt in $d_6$ dimethylsulphoxide using tetramethylsilane as internal standard ($\delta=0$) included the following resonances ($\delta$):1.5 (multiplet, 6H); 2.6 (multiplet, 2H); 3.1 (doublet, 3H); 3.5 (multiplet, 2H); 4.1 (multiplet, 2H); 6.55 (singlet, 1H).

EXAMPLE 56

A mixture of 2-[2-(2,2,2-trifluoroethyl)guanidino]-4-(5-aminopentyl)thiazole (1.0 g.) and 1-methylamino-1-methylthio-2-nitroethylene (0.55 g.) in acetonitrile (5 ml.) was heated under reflux for 4 hours. The mixture was then evaporated to dryness and the residue purified by preparative thin layer chromatography using ethyl acetate/methanol/water 6:1:1 v/v/v as developing solvent to give, on extraction of the appropriate band with chloroform/ethanol 1:1 v/v (200 ml.) and evaporation, a colourless glass. This was treated with an excess of maleic acid in acetone and 1-[5-(2-[2-(2,2,2-trifluoroethyl)guanidino]thiazol-4-yl)pentylamino]-1-methylamino-2-nitroethylene was precipitated as a salt containing 1.5 equivalent of maleic acid. The n.m.r. spectrum in $d_6$ dimethylsulphoxide using tetramethylsilane as an internal standard ($\delta=0$) included the following resonances ($\delta$):1.6 (multiplet, 6H); 2.8 (broad doublet, 3H); 3.2 (multiplet, 2H); 4.2 (quartet, 2H); 6.5 (singlet, 1H); 6.6 (singlet, 1H).

EXAMPLE 57

To 2-[2-(2,2,2-trifluoroethyl)guanidino]-4-[5-(3-cyano-2-methylisothioureido)pentyl]thiazole (0.25 g.) in ethanol (1 ml.) was added ethanolic methylamine (33% w/v, 30 ml.). The mixture was allowed to stand overnight at room temperature and then evaporated to dryness to give 2-[2-(2,2,2-trifluoroethyl)guanidino]-4-[5-(3-cyano-2-methylguanidino)pentyl]thiazole. The n.m.r. spectrum in $d_6$ dimethylsulphoxide containing tetramethylsilane as internal standard ($\delta=0$) included the following resonances ($\delta$):1.5 (multiplet, 6H); 2.7 (doublet, 3H); 3.1 (multiplet, 2H); 4.1 (multiplet, 2H); 6.4 (singlet, 1H).

The 2-[2-(2,2,2-trifluoroethyl)guanidino]-4-[5-(3-cyano-2-methylisothioureido)pentyl]thiazole used as starting material may be prepared as follows:

A mixture of 2-[2-(2,2,2-trifluoroethyl)guanidino]-4-(5-aminopentyl)thiazole (1.4 g.) and dimethyl (cyanoimido)dithiocarbonate (0.9 g.) in ethanol (10 ml.) was allowed to stand at room temperature for 6 days. The solvent was then evaporated and the residue purified by column chromatogrpahy on silica gel using methanol/chloroform 1:19 v/v as solvent. The resulting 2-[2-(2,2,2-trifluoroethyl)guanidino]-4-[5-(3-cyano-2-methylisothioureido)pentyl]thiazole was used without further purification.

EXAMPLE 58

A mixture of 2-[2-(2,2,2-trifluoroethyl)guanidino]-4-[5-(3-cyano-2-methylisothioureido)pentyl]thiazole (0.5 g.) and 1,2-diaminoethane (1.5 ml.) in ethanol (1 ml.) was allowed to stand at room temperature overnight. The mixture was then evaporated to dryness and the residue purified by preparative medium pressure liquid chromatography on silica gel using methanol/chloroform 1:4 v/v as solvent to give 2-[2-(2,2,2-trifluoroethyl)guanidino]-4-[5-(3-cyano-2-[2-aminoethyl]-guanidino)pentyl]thiazole as a straw coloured gum. A sample of the salt prepared with maleic acid included the following n.m.r. resonanes when examined in $d_6$ dimethylsulphoxide containing tetramethylsilane as an internal standard ($\delta=0$) ($\delta$):1.5 (multiplet, 6H); 3.0 (multiplet, 4H); 3.3 (multiplet, 2H); 4.1 (multiplet, 2H); 6.5 (singlet, 1H).

EXAMPLE 59

A mixture of 2-[2-(2,2,2-trifluoroethyl)guanidino]-4-(5-aminopentyl)thiazole (0.3 g.) and ethyl N-cyanopropionimidate (0.13 g.) in ethanol (3 ml.) was allowed to stand at room temperature for 6 hours then evaporated to dryness and the residue purified by preparative thin layer chromatography using ethyl acetate/methanol/water 12:2:1 v/v/v as developing solvent. The purified product was treated in acetone with excess maleic acid in acetone to give 2-[2-(2,2,2-trifluoroethyl)guanidino]-4-[5-(3-cyano-2-ethylamidino)pentyl]thiazole containing 1.2 equivalents of maleic acid. The n.m.r. spectrum in $d_6$ dimethylsulphoxide containing tetramethylsilane as an internal standard ($\delta=0$) included the following resonances ($\delta$):1.2 (triplet, 3H); 1.5 (multiplet, 6H); 2.5 (multiplet, 4H); 3.2 (quartet, 2H); 4.2 (quartet, 2H); 6.55 (singlet, 1H).

EXAMPLE 60

A mixture of 2-[2-(2,2,2-trifluoroethyl)guanidino]-4-(4-aminobutyl)thiazole (0.75 g.) and 1,1-di(methylthio)-2-nitroethylene (0.43 g.) was allowed to stand in acetonitrile (12 ml.) at room temperature overnight. The resulting mixture was purified by preparative thin layer chromatography using chloroform/methanol 9:1 v/v as developing solvent. The product was isolated as a minor band and extracted with chloroform/ethanol 1:1 v/v (200 ml.). On evaporation to dryness and treatment with maleic acid in methanol/acetone/ether there was obtained 1,1-di[4-(2-[2-(2,2,2-trifluoroethyl)guanidino]-thiazol-4-yl)butylamino]-2-nitroethylene containing 1.75 equivalents of maleic acid, m.p. 123°–125° (decomp).

EXAMPLE 61

A mixture of 2-[2-(2,2,2-trifluoroethyl)guanidino]-4-(4-aminobutyl)thiazole (0.12 g.) and 2-[2-(2,2,2-trifluoroethyl)guanidino]-4-[4-isothiocyanatobutyl]-thiazole (0.12 g.) in methanol (3 ml.) was allowed to stand at room temperature overnight. The mixture was then evaporated to dryness and purified by preparative thin layer chromatography using methanol/chloroform/ammonia 85:15:1 v/v/v as developing solvent. The appropriate band was extracted with chloroform/ethanol 1:1 v/v (200 ml.) and the resulting solution evaporated to give a brown gum. This was treated in acetone with excess maleic acid to give 1,3-di[4-(2-[2-(2,2,2-trifluoroethyl)guanidino]thiazol-4-yl)butylamino)thiourea containing 2.25 equivalents of maleic acid. The n.m.r. spectrum in $d_6$ dimethylsulphoxide containing tetramethylsilane as internal standard ($\delta=0$) included the following resonances ($\delta$): 1.5 (multiplet, 8H); 3.3 (multiplet, 4H); 4.1 (quartet, 4H); 6.5 (singlet, 2H).

The 2-[2-(2,2,2-trifluoroethyl)guanidino]-4-[4-isothiocyanatobutyl]thiazole used as starting material may be prepared as follows:

A solution of 2-[2-(2,2,2-trifluoroethyl)guanidino]-4-(4-aminobutyl)thiazole (0.75 g.) in tetrahydrofuran (20 ml.) was added dropwise over 15 minutes to a stirred solution of thiocarbonyldiimidazole (0.5 g.) in tetrahydrofuran (20 ml.). The mixture was then stirred at room temperature for 20 minutes and then evaporated to dryness. The residue was partitioned between ethyl acetate (50 ml.) and water. (20 ml.). The organic layer was washed with water (2×20 ml.) and then evaporated to dryness. The residue was purified by preparative thin layer chromatography using methanol/chloroform 1:9 v/v as developing solvent. The purified product was isolated as colourless gum and used without further purification.

EXAMPLE 62

A mixture of 2-(2-guanidino)-4-(4-aminobutyl)-thiazole (0.30 g.) and 2-[2-(2,2,2-trifluoroethyl)-guanidino]-4-(4-isothiocyanatobutyl)thiazole (0.35 g.) in tetrahydrofuran (30 ml.) was allowed to stand at room temperature overnight. The solution was then evaporated to dryness, and the residue purified by preparative thin layer chromatography using methanol/chloroform 15:85 v/v as developing solvent. The appropriate band was extracted with chloroform/ethanol (1:1 v/v, 200 ml.) and this extract was evaporated to give a fawn glass. This was treated in acetone with excess maleic acid to give 1-[4-(2-[2-(2,2,2-trifluoroethyl)guanidino]-thiazol-4-yl)butyl]-3-[4-(2-guanidinothiazol-4-yl)butyl]-thiourea containing 2.25 equivalents of maleic acid. The n.m.r. spectrum in $d_6$ dimethylsulphoxide containing tetramethylsilane as internal standard ($\delta=0$) included the following resonances ($\delta$): 1.5 (multiplet, 8H); 3.35 (multiplet, 4H); 4.1 (quartet, 4H); 6.45 (singlet, 1H); 6.85 (singlet, 1H).

EXAMPLE 63

A mixture of 4-methyl-5-[(2-aminoethyl)thiomethyl]imidazole dihydrochloride (0.5 g.), triethylamine (1 ml.) and 2-[2-(2,2,2-trifluoroethyl)guanidino]-(4-isothiocyanatobutyl)thiazole (0.5 g.) in tetrahydrofuran (15 ml.) was allowed to stand at room temperature overnight. The solution was then filtered, and the filtrate evaporated to dryness. The residue was purified by preparative thin layer chromatography using ethyl acetate/methanol/ammonia 6:1:1 v/v/v as developing solvent. The appropriate band was isolated and further purified by preparative thin layer chromatography using methanol/chloroform/ammonia 15:85:1 v/v/v as developing solvent. The appropriate band after extraction and evaporation yielded a brown gum. This was treated in acetone with excess maleic acid to give 1-[4-(2-[2-(2,2,2-trifluoroethyl)guanidino]thiazol-4-yl)butyl]-3-[2-([4-methylimidazol-5-yl]methylthio)ethyl]thiourea containing 2.25 equivalents of maleic acid. The n.m.r. spectrum in $d_6$ dimethyl sulphoxide containing tetramethylsilane as internal standard ($\delta=0$) included the following resonances ($\delta$): 1.5 (multiplet, 4H); 2.25 (singlet, 3H); 2.5 (multiplet, 4H); 3.3 (multiplet, 4H); 3.8 (singlet, 2H); 4.1 (quartet, 2H); 6.45 (singlet, 1H); 8.8 (singlet, 1H).

EXAMPLE 64

A mixture of 2-[2-(2,2,2-trifluoroethyl)guanidino]-4-(4-aminobutyl)thiazole (0.45 g.) and 2-chloropyrimidine (0.18 g.) was heated under reflux in acetonitrile (5 ml.) for 16 hours. The reaction mixture was then evaporated to dryness and the residue purified by medium pressure liquid chromatography on silica gel using chloroform/methanol/ammonia 1900:100:5 v/v/v as eluant. The appropriate fraction was evaporated to dryness and the residue recrystallised from acetonitrile to give 2-(4-[2-(2-[2,2,2-trifluoroethyl]guanidino)thiazol-4-yl]butylamino)pyrimidine (0.29 g.), m.p. 173°–175°.

EXAMPLE 65

A mixture of 2-[2-(2,2,2-trifluoroethyl)guanidino]-4-[4-(3-[2-aminophenyl]thioureido)butyl]thiazole (0.45 g.), silver nitrate (0.34 g.) and triethylamine (0.28 ml.) in dimethylformamide (3 ml.) was stirred vigorously at ambient temperature overnight. Hydrogen sulphide gas was then bubbled through the reaction mixture until no more solid precipitated. The reaction mixture was filtered through a pad of diatomaceous earth and the filtrate evaporated to dryness in vacuo. The residue was purified by low pressure liquid chromatography using chloroform/methanol/ammonia, 9:1:0.1 v/v/v as eluant to give 2-[4-(2-[2-(2,2,2-trifluoroethyl)guanidino]-thiazol-4-yl)butylamino]benzimidazole which was converted to the hydrogen maleate salt (0.25 g.), m.p. 183°–186°.

The 2-[2-(2,2,2-trifluoroethyl)guanidino]-4-[4-(3-[2-aminophenyl]thioureido)butyl]thiazole used as starting materials may be obtained as follows:

A miture of 2-[2-(2,2,2-trifluoroethyl)guanidino]-4-(4-isothiocyanatobutyl)thiazole (0.33 g.) and o-phenylenediamine in alcohol (5 ml.) was heated under reflux for 2 hours. Evaporation of the reaction mixture to dryness gave 2-[2-(2,2,2-trifluoroethyl)-guanidino]-4-[4-(3-[2-aminophenyl]thioureido)butyl]-thiazole as an oil which was used without further purification.

EXAMPLE 66

1-Methylamino-1-methylthio-2-nitroethylene (0.16 g.) was added to a solution of 2-[2-(2,2,2-trifluoroethyl)-guanidino]-4-[(2-aminoethyl)thiomethyl]thiazole (0.33 g.) in acetonitrile (10 ml.) and the mixture heated under reflux for 30 hours. The mixture was evaporated to dryness and the residual gum was purified by column chromatography on Merck Kieselgel 60 using acetonitrile followed by chloroform/methanol/ammonia 8:2:0.2 v/v/v as eluting solvents. Fractions containing the product were evaporated and the residual gum was further purified by preparative thin layer chromatography using chloroform/methanol/ammonia 8:2:0.2 v/v/v as developing solvent.

The 1-[2-(2-[2-(2,2,2-trifluoroethyl)guanidino]thiazol-4-ylmethylthio)ethylamino]-1-methylamino-2-nitroethylene (0.06 g.) obtained was characterised as the hydrogen maleate, m.p. 144°–147° (decomp.).

EXAMPLE 67

Dimethyl (methylsulphonylimido)dithiocarbonate (0.13 g.) was added to a solution of 2-[2-(2,2,2-trifluoroethyl)guanidino]-4-[(2-aminoethyl)thiomethyl]thiazole (0.2 g.) in ethanol (10 ml.) and stirred at room temperature for 16 hours. The solvent was removed by evaporation and the residual gum was purified by preparative thin layer chromatography using chloroform/methanol/ammonia 8:2:0.2 v/v/v as developing solvent. The appropriate zone of the chromatogram was isolated and extracted with methanol/ammonia 10:1 v/v (50 ml.). The solvent was evaporated and the residue was dissolved in acetonitrile (10 ml.) filtered and evaporated. The residual gum was dissolved in methanol (3 ml.) and treated with a solution of fumaric acid (0.1 g.) in methanol (5 ml.). The solution was evaporated and the residue was triturated with ethyl acetate to give 2-[2-(2,2,2-trifluoroethyl)guanidino]-4-[2-(3-methylsulphonyl-2-methylisothioureido)ethylthiomethyl]thiazole trifumarate, m.p. 148° (decomp.).

EXAMPLE 68

2-[2-(2,2,2-Trifluoroethyl)guanidino]-4-[2-(3-methylsulphonyl-2-methylisothioureido)ethylthiomethyl]-thiazole (0.4 g.) was dissolved in ethanolic methylamine (33% w/v 15 ml.) and allowed to stand at room temperature for 64 hours. The solvent was evaporated and the residual gum was purified by preparative thin layer chromatography using chloroform/methanol/ammonia 8:2:0.2 v/v/v as developing solvent. The appropriate zone of the chromatogram was isolated and extracted with methanol/ammonia 10:1 v/v (50 ml.). The solvent was evaporated and the residual gum was dissolved in acetonitrile, filtered and the filtrate evaporated. The residual gum was dissolved in methanol and treated with a solution of excess fumaric acid in methanol. The solvent was evaporated and the residue triturated with acetonitrile to give 2-[2-(2,2,2-trifluoroethyl)-guanidino]-4-[2-(2-methylsulphonyl-3-methylguanidino)ethylthiomethyl]thiazole as a cream solid (0.29 g.), m.p. 118°–123° (decomp.), containing 1.5 molar equivalents of fumaric acid.

EXAMPLE 69

Dimethyl (methylsulphonylimido)dithiocarbonate (0.2 g.) and 2-[2-(2,2,3,3,3-pentafluoropropyl)-guanidino]-4-[(2-aminoethyl)thiomethyl]thiazole (0.36 g.) were dissolved in ethanol (5 ml.) and allowed to stand at room temperature for 2 hours. The mixture was evaporated to dryness and the residual gum was dissolved in ethanolic methylamine (33% w/v, 3 ml.) and allowed to stand at room temperature for 2 hours. The mixture was evaporated to dryness and the residual gum was purified by preparative thin layer chromatography using ethyl acetate/methanol/ammonia 6:1:1 v/v/v as developing solvent. The appropriate zone of the chromatogram was isolated and extracted with methanol/ammonia 10:1 v/v (50 ml.). The solvent was evaporated and the residue was dissolved in ethyl acetate (10 ml.), filtered and the filtrate was treated with a solution of maleic acid (0.05 g.) in ethyl acetate (10 ml.). The resulting precipitate was filtered to give 2-[2-(2,2,3,3,3-pentafluoropropyl)guanidino]-4-[2-(2-methylsulphonylmethylguanidino)ethylthiomethyl]thiazole as a cream solid (0.06 g.), m.p 149°-151° containing maleic acid (1.25 molar equivalent) and water (1 molar equivalent).

The 2-[2-(2,2,3,3,3-pentafluoropropyl)guanidino]-4-[(2-aminoethyl)thiomethyl]thiazole used as starting material may be prepared as follows:

A mixture of 2,2,3,3,3-pentafluoropropylamine hydrochloride (5.0 g.) and sodium dicyanamide (2.4 g.) in butanol (100 ml.) was heated under reflux for 6 hours. The suspension was cooled, filtered and evaporated to dryness. The residual gum and thioacetamide (2.25 g.) were suspended in water (50 ml.) and cooled to 5°. Concentrated hydrochloric acid (3 ml.) was added dropwise whilst the suspension was stirred and the resulting mixture was heated at 100° for 1 hour. The mixture was filtered and the filtrate basified with saturated aqueous potassium carbonate solution and extracted with ethyl acetate (2×100 ml.). The ethyl acetate layer was dried (sodium sulphate) and evaporated to dryness. A solution of maleic acid (3.1 g.) in acetone (10 ml.) was added to the residual gum and the resulting solid was filtered and added to 1N sodium hydroxide solution. The mixture was extracted with ethyl acetate (100 ml.) which was then dried (sodium sulphate) and evaporated to dryness. The residual gum and 1,3-dichloroacetone (1.5 g.) were dissolved in acetone (50 ml.), treated with concentrated hydrochloric acid (0.1 ml.) and stirred at room temperature for 40 hours. The mixture was evaporated to dryness and the residual gum triturated with ether and the resulting solid (1.6 g.) was filtered. The solid and 2-aminoethanethiol hydrochloride (1 g.) were dissolved in ethanol (30 ml.), mixed with a solution of sodium hydroxide (1 g.) in water (15 ml.) and stirred at room temperature for 16 hours. The mixture was evaporated to dryness and the residual gum was partitioned between ethyl acetate (100 ml.) and water (100 ml.). The ethyl acetate layer was washed with water (50 ml.), dried (magnesium sulphate) and evaporated to dryness to give 2-[2-(2,2,3,3,3-pentafluoropropyl)guanidino]-4-[(2-aminoethyl)thiomethyl]thiazole as a gum (1.5 g.) which was used without further purification.

EXAMPLE 70

Dimethyl (methylsulphonylimido)dithiocarbonate (0.055 g.) and 2-[2-(2,2,2-trichloroethyl)guanidino]-4-[(2-aminoethyl)thiomethyl]thiazole (0.11 g.) were dissolved in ethanol (2 ml.) and allowed to stand at room temperature for 16 hours. The mixture was evaporated to dryness and the residual gum was dissolved in ethanolic methylamine (33% w/v 5 ml.) and allowed to stand at room temperature for 5 hours. The mixture was evaporated to dryness and the residual gum was purified by preparative thin layer chromatography using ethyl acetate/methanol/ammonia 6:1:1 v/v/v as developing solvent. The appropriate zone of the chromatogram was isolated and extracted with methanol/ammonia 10:1 v/v (50 ml.). The solvent was evaporated and the residue was dissolved in ethyl acetate, filtered, and added to a solution of maleic acid (0.05 g.) in ethyl acetate. The resulting solid was filtered to give 2-[2-(2,2,2-trichloroethyl)guanidino]-4-[2-(2-methylsulphonyl-3-methylguanidino)ethylthiomethyl]thiazole as a pale brown solid (0.06 g.), m.p. 126°-130° (decomp.) containing 1.25 molar equivalents of maleic acid.

The 2-[2-(2,2,2-trichloroethyl)guanidino]-4-[(2-aminoethyl)thiomethyl]thiazole used as starting material may be prepared as follows:

A mixture of 2,2,2-trichloroethylamine hydrochloride (4 g.) and sodium dicyanamide (1.95 g.) in butanol (100 ml.) was heated under reflux for 6 hours. The suspension was cooled, filtered and the filtrate evaporated to dryness. The residual gum and thioacetamide (1.8 g.) were mixed with water (100 ml.) and cooled to 5°. Concentrated hydrochloric acid (2.2 ml.) was added dropwise whilst the suspension was stirred and the resulting mixture was then heated at 100° for 1 hour. The solution was filtered and the filtrate was basified with 10N sodium hydroxide solution and extracted with ethyl acetate (2×100 ml.). The organic layer was dried (sodium sulphate) and evaporated. The residual gum was dissolved in acetone (10 ml.) and added to a solution of maleic acid (2.55 g.) in acetone (20 ml.). The precipitated solid was filtered, added to 1N sodium hydroxide solution and the product was extracted with ethyl acetate (100 ml.). The ethyl acetate was dried (magnesium sulphate) and the solvent evaporated.

The residual gum and 1,3-dichloroacetone (1.41 g.) were dissolved in acetone (20 ml.), treated with concentrated hydrochloric acid (0.01 ml.) and stirred at room temperature for 40 hours. The suspension was filtered and the cream solid was dissolved in ethanol (30 ml.). 2-Aminoethanethiol (0.5 g.) was added to the solution and this mixture was added to a solution of sodium hydroxide (0.45 g.) in water (15 ml.) and stirred at room temperature for 16 hours. The solvent was evaporated and the residual gum was partitioned between ethyl acetate (100 ml.) and water (100 ml.). The ethyl acetate layer was washed with water (50 ml.), dried (magnesium sulphate) and evaporated to give 2-[2-(2,2,2-trichloroethyl)guanidino]-4-[(2-aminoethyl)thiomethyl]thiazole as a gum (0.11 g.) which was used without further purification.

EXAMPLE 71

The process described in Example 70 was repeated using 2-[2-(2-chloro-2,2-difluoroethyl)guanidino]-4-[(2-aminoethyl)thiomethyl]thiazole (0.33 g.) in place of 2-[2-(2,2,2-trichloroethyl)guanidino]-4-[(2-aminoethyl)thiomethyl]thiazole and there was thus obtained 2-[2-(2-chloro-2,2-difluoroethyl)guanidino]-4-[2-(2-methylsulphonyl-3-methylguanidino)ethylthiomethyl]thiazole as a cream solid (0.27 g.), m.p. 130°-133° (decomp.), containing 1.2 molar equivalents of maleic acid.

The 2-[2-(2-chloro-2,2-difluoroethyl)guanidino]-4-[(2-aminoethyl)thiomethyl]thiazole used as starting material may be obtained as follows:

Lithium aluminium hydride (4.5 g.) was added to ether (150 ml.) stirred under an atmosphere of argon. The suspension was cooled to 5° and a solution of chlorodifluoroacetamide (13.1 g.) in ether (50 ml.) was added dropwise. The mixture was stirred at room temperature for 2 hours then a saturated aqueous solution of sodium chloride (15 ml.) was added dropwise. The reaction mixture was filtered and the solid residue was washed with ether (2×100 ml.). The ether solutions were combined, dried (magnesium sulphate) and treated with an excess of a saturated solution of hydrogen chloride in ether. The precipitate was filtered to give 2-chloro-2,2-difluoroethylamine hydrochloride (6.0 g.), m.p. 224°-226° (with sublimation).

2-Chloro-2,2-difluoroethylamine hydrochloride (4 g.) and sodium dicyanamide (2.5 g.) were suspended in butanol (20 ml.) and heated under reflux for 6 hours. The suspension was cooled, filtered and evaporated to dryness. The residual gum and thioacetamide (2.5 g.) were suspended in water (30 ml.) and cooled to 5°. Concentrated hydrochloride acid (3 ml.) was added dropwise and the mixture was heated at 100° for 30 minutes. The mixture was cooled and extracted with ethyl acetate (50 ml.). The ethyl acetate layer was extracted with 1N hydrochloric acid and the aqueous extracts were combined, basified with 10N sodium hydroxide solution and extracted with ethyl acetate (100 ml.). The ethyl acetate layer was dried (magnesium sulphate) and to this solution was added a solution of maleic acid (2.5 g.) in ethyl acetate (50 ml.). The resulting precipitate was filtered and added to 1N sodium hydroxide solution. The mixture was extracted with ethyl acetate (100 ml.) which was then dried (magnesium sulphate) and evaporated to dryness. The residual gum and 1,3-dichloroacetone (1.35 g.) were dissolved in acetone (15 ml.) and stirred at room temperature for 40 hours. The mixture was evaporated and triturated with ether to give a crystalline precipitate. The solid was filtered and dissolved in ethanol (50 ml.). 2-Aminoethanethiol (1.7 g.) was added to the solution followed by a solution of sodium hydroxide (1.5 g.) in water (25 ml.) and the mixture was stirred at room temperature for 1 hour. The mixture was evaporated to dryness and the residue partitioned between ethyl acetate (100 ml.) and water (100 ml.). The ethyl acetate layer was dried (magnesium sulphate) and evaporated to dryness to give 2-[2-(2-chloro-2,2-difluoroethyl)guanidino]-4-[(2-aminoethyl)thiomethyl]thiazole as a gum (2.8 g.) which was used without further purification.

EXAMPLE 72

Dimethyl (methylsulphonylimido)dithiocarbonate (0.11 g.) was added to a solution of 2-[2-(2,2,3,3-tetrafluoropropyl)guanidino]-4-[(2-aminoethyl)thiomethyl]thiazole (0.2 g.) in ethanol (3 ml.) and the mixture allowed to stand at room temperature for 64 hours. The solvent was removed by evaporation and the residue was dissolved in ethanolic methylamine (33% w/v, 10 ml.) and allowed to stand at room temperature for 2 hours. After evaporation of solvent the residual gum was purified by column chromatography using chloroform/methanol/ammonia 9:1:0.1 v/v/v as eluting solvent. Fractions containing the product were evaporated and the residue was further purified by preparative thin layer chromatography using ethyl acetate/methanol/ammonia 6:1:1 v/v/v as developing solvent. The appropriate zone of the chromatogram was isolated and extracted with methanol/ammonia 10:1 v/v (50 ml.). The solvent was evaporated and the residual gum was dissolved in ethyl acetate, filtered and the filtrate was treated with a solution of maleic acid (0.05 g.) in ethyl acetate to give 2-[2-(2,2,3,3,-tetrafluoropropyl)-guanidino]-4-[2-(2-methylsulphonyl-3-methylguanidino)ethylthiomethyl]thiazole hydrogen maleate (0.07 g.), m.p. 144°-147° (decomp.).

The 2-[2-(2,2,3,3-tetrafluoropropyl)guanidino]-4-[(2-aminoethyl)thiomethyl]thiazole used as starting material may be prepared as follows:

A mixture of 2,2,3,3-tetrafluoropropylamine hydrochloride (5 g.) and sodium dicyanamide (2.8 g.) in butanol (25 ml.) was heated under reflux for 6 hours. The suspension was cooled, filtered and evaporated to dryness. The residual gum and thioacetamide (2.8 g.) were suspended in water (50 ml.) and cooled to 5°. Concentrated hydrochloric acid (3 ml.) was added dropwise whilst the suspension was stirred and the resulting mixture was heated at 100° for 30 minutes. The mixture was extracted with ethyl acetate (50 ml.) and the organic layer was re-extracted with 1N hydrochloric acid (25 ml.). The aqueous layers were combined, basified with 10N sodium hydroxide solution and the product was extracted with ethyl acetate (100 ml.). The ethyl acetate layer was dried (magnesium sulphate) and mixed with a solution of maleic acid (2.5 g.) in ethyl acetate. The resulting precipitate was filtered and added to 1N sodium hydroxide solution (50 ml.) and extracted with ethyl acetate (50 ml.). The ethyl acetate layer was dried (magnesium sulphate) and evaporated to dryness. The residual gum and 1,3-dichloroacetone (2.2 g.) were dissolved in acetone (50 ml.), treated with concentrated hydrochloric acid (0.1 ml.) and stirred at room temperature for 21 hours. The mixture was evaporated to dryness. The residual gum and 2-aminoethanethiol hydrochloride (3 g.) were dissolved in ethanol (60 ml.) and to this solution was added a solution of sodium hydroxide (3 g.) in water (30 ml.). The mixture was stirred at room temperature for 16 hours and evaporated to dryness. The residual gum was partitioned between ethyl acetate (100 ml.) and water (100 ml.). The ethyl acetate layer was washed with water (50 ml.), dried (magnesium sulphate) and evaporated to dryness. The residual gum was purified by column chromatography using chloroform/methanol/ammonia 9:1:0.1 v/v/v as eluting solvent to give 2-[2-(2,2,3,3-tetrafluoropropyl)guanidino]-4-[(2-aminoethyl)thiomethyl]thiazole as a gum (1.05 g.) which was used without further purification.

EXAMPLE 73

Dimethyl (methylsulphonylimido)dithiocarbonate (0.1 g.) and 2-[2-(2,2-difluoroethyl)guanidino]-4-[(2-aminoethyl)thiomethyl]thiazole (0.15 g.) were dissolved in ethanol (3 ml.) and heated under reflux for 20 minutes. The mixture was evaporated to dryness and the residual gum was dissolved in ethanolic methylamine (33% w/v, 3 ml.) and allowed to stand at room temperature for 16 hours. The mixture was evaporated to dryness and the residual gum was purified by preparative thin layer chromatography using ethyl acetate/methanol/ammonia 6:1:1 v/v/v as developing solvent. The appropriate zone of the chromatogram was isolated and extracted with methanol/ammonia 10:1 v/v (50 ml.). The solvent was evaporated and the residue was dissolved in ethyl acetate, filtered and added to a solution of maleic acid (0.1 g.) in ethyl acetate. The resulting solid was filtered to give 2-[2-(2,2-difluoroethyl)-guanidino]-4-[2-(2-methylsulphonyl-3-methylguanidino)ethylthiomethyl]thiazole as a cream solid (0.07 g.), m.p. 85°-89°, containing 1.4 molar equivalents of maleic acid.

The 2[2-(2,2-difluoroethyl)guanidino]-4-[(2-aminoethyl)thiomethyl]thiazole used as starting material may be prepared as follows:

A mixture of 2,2-difluoroethylamine hydrochloride (5 g.) and sodium dicyanamide (3.8 g.) in butanol (60 ml.) was heated under reflux for 6 hours. The suspension was cooled, filtered and the filtrate evaporated to dryness. The residual gum and thioacetamide (3.8 g.) were mixed with water (50 ml.) and cooled to 5°. Concentrated hydrochloric acid (4 ml.) was added dropwise whilst the suspension was stirred and the mixture was then heated at 100° C. for 30 minutes. The reaction mixture was extracted with ethyl acetate (50 ml.) and the ethyl acetate was re-extracted with 1N hydrochloric acid (50 ml.). The combined aqueous extracts were basified with 10N sodium hydroxide solution and extracted with ethyl acetate (100 ml.). The organic layer was dried (magnesium sulphate) and added to a solution of maleic acid (6 g.) in ethyl acetate (50 ml.). Petroleum ether (b.p. 60°-80°) was added and the salt crystallised. The solid was filtered, added to 1N sodium hydroxide solution and extracted with ethyl acetate (100 ml.). The ethyl acetate layer was dried (magnesium sulphate) and evaporated to dryness. The residual gum and 1,3-dichloroacetone (1.5 g.) were dissolved in acetone (20 ml.) and stirred at room temperature for 21 hours. The solvent was evaporated and the residue triturated with ether and filtered to give a solid (1.6 g.). This solid and 2-aminoethanethiol (1.7 g.) were dissolved in ethanol (25 ml.) and added to a solution of sodium hydroxide (1.6 g.) in water (12 ml.). The mixture was stirred at room temperature for 2 hours and the solvent was removed by evaporation. The residue was partitioned between ethyl acetate (100 ml.) and water (100 ml.) and the ethyl acetate layer was dried (magnesium sulphate) and evaporated to dryness to give 2-[2-(2,2-difluoroethyl)guanidino]-4-[(2-aminoethyl)thiomethyl]thiazole as a gum (1.5 g.) which was used without further purification.

EXAMPLE 74

Dimethyl (methylsulphonylimido)dithiocarbonate (0.24 g.) and 2-[2-(1,1,1-trifluoroisopropyl)guanidino]-4-[(2-aminoethyl)thiomethyl]thiazole (0.4 g.) were dissolved in ethanol (5 ml.) and heated under reflux for 30 minutes. The solvent was evaporated and the residual gum was dissolved in ethanolic methylamine (33% w/v, 3 ml.) and allowed to stand at room temperature for 16 hours. The solvent was evaporated and the residual gum was purified by preparative thin layer chromatography using ethyl acetate as developing solvent. The appropriate zone of the chromatogram was isolated and extracted with methanol/ammonia 10:1 v/v (50 ml.). The solvent was evaporated and the residual gum was again subjected to preparative thin layer chromatography using the conditions described above. The isolated gum was dissolved in ethyl acetate and added to a solution of maleic acid (0.014 g.) in ethyl acetate. The solvent was evaporated to give 2-[2-(1,1,1-trifluoroisopropyl)guanidino]-4-[2-(2-methylsulphonyl-3-methylguanidino)ethylthiomethyl]thiazole hydrogen maleate as a straw-coloured gum. The n.m.r. spectrum in d$_4$ methanol using tetramethylsilane as internal standard (δ=0) included the following resonances (δ): 1.5 (3H, doublet); 2.8 (3H, singlet); 2.9 (3H, singlet); 3.8 (2H, singlet); 4.6 (1H, complex); 7.1 (1H, singlet).

The 2-[2-(1,1,1-trifluoroisopropyl)guanidino]4-[(2-aminoethyl)thiomethyl]thiazole used as starting material may be obtained as follows:

1,1,1-Trifluoroisopropylamine hydrochloride (2 g.) and sodium dicyanamide (1.2 g.) in butanol (20 ml.) were heated under reflux for 6 hours. The suspension was cooled, filtered and the filtrate evaporated to dryness. The residual gum and thioacetamide (1.2 g.) were mixed with water (20 ml.) and cooled to 5°. Concentrated hydrochloric acid (2 ml.) was added dropwise whilst the suspension was stirred and the resulting mixture was heated at 100° for 30 minutes. The reaction mixture was extracted with ethyl acetate (50 ml.) and the organic layer was re-extracted with 1N hydrochloric acid. The aqueous extracts were combined, basified with 10N sodium hydroxide solution and extracted with ethyl acetate (100 ml.). The organic layer was dried (magnesium sulphate) and evaporated to dryness. The residual gum and 1,3-dichloroacetone (0.6 g.) were dissolved in acetone (10 ml.) and allowed to stand at room temperature for 88 hours. The solvent was evaporated to dryness and dissolved in ethanol (20 ml.). 2-Aminoethanethiol (0.6 g.) was added and this mixture was then added to a solution of sodium hydroxide (0.5 g.) in water (10 ml.). After stirring for 2 hours at room temperature, the mixture was evaporated to dryness and the residual gum was partitioned between ethyl acetate (50 ml.) and water (50 ml.). The organic layer was dried (magnesium sulphate) and evaporated to dryness to give 2-[2-(2,2,2-trifluoroethyl)guanidino]-4-[(2-aminoethyl)thiomethyl]thiazole as a gum (0.4 g.) which was used without further purification.

EXAMPLE 75

Dimethyl (cyanoimido)dithiocarbonate (0.05 g.) and 2-[2-(2,2,3,3-tetrafluoropropyl)guanidino]-4-[(2-aminoethyl)thiomethyl]thiazole (0.12 g.) were dissolved in ethanol (2 ml.) and allowed to stand at room temperature for 16 hours. The mixture was evaporated to dryness, dissolved in ethanolic methylamine (33% w/v, 5 ml.) and allowed to stand at room temperature for 16 hours. The mixture was evaporated to dryness and the residue was purified by preparative thin layer chromatography using ethyl acetate/methanol/ammonia 6:1:1 v/v/v as developing solvent. The appropriate zone of the chromatogram was isolated and extracted with methanol/ammonia 50:1 v/v. The solvent was evaporated and the residual gum was dissolved in ethyl acetate, filtered and added to a solution of maleic acid (0.05 g.) in ethyl acetate. The precipitated solid was filtered to give 2-[2-(2,2,3,3-tetrafluoropropyl)guanidino]-4-[2-(2-cyano-3-methylguanidino)ethylthiomethyl]thiazole hydrogen maleate (0.1 g.), m.p. 146°-8° (decomp.).

EXAMPLE 76

The process described in Example 75 was repeated using 2-[2-(2-chloro-2,2-difluoroethyl)guanidino]-4-[(2-aminoethyl)thiomethyl]thiazole 0.33 g. in place of 2-[2-(2,2,3,3-tetrafluoropropyl)guanidino]-4-[(2-aminoethyl)thiomethyl]thiazole and there was thus obtained 2-[2-(2-chloro-2,2-difluoroethyl)guanidino]-4-[2-(2-cyano-3-methylguanidino)ethylthiomethyl]thiazole (0.35 g.), m.p. 118°-122° (decomp.) containing 1.25 molar equivalents of maleic acid.

EXAMPLE 77

Dimethyl (cyanoimido)dithiocarbonate (0.07 g.) and 2-[2-(2,2-difluoroethyl)guanidino]-4-[(2-aminoethyl)thiomethyl]thiazole (0.15 g.) were dissolved in ethanol (3 ml.) and heated under reflux for 20 minutes. The solvent was evaporated and the residual gum was dissolved in ethanolic methylamine (33% w/v, 3 ml.) and allowed to stand at room temperature for 16 hours. The solvent was evaporated and the residual gum purified by preparative thin layer chromatography using ethyl acetate/methanol/ammonia 6:1:1 v/v/v as developing solvent. The appropriate zone of the chromatogram was isolated and extracted with methanol/ammonia 10:1 v/v. The solvent was evaporated and the residue was dissolved in ethyl acetate, filtered and added to a solution of maleic acid (0.1 g.) in ethyl acetate. The precipitate was filtered to give 2-[2-(2,2-difluoroethyl)guanidino]-4-[2-(2-cyano-3-methylguanidino)ethylthiomethyl]thiazole (0.11 g.), m.p. 108°-112° (decomp.) containing 1.25 molar equivalents of maleic acid.

EXAMPLE 78

1-Methylamino-1-methylthio-2-nitroethylene (0.05 g.) and 2-[2-(2,2,3,3-tetrafluoropropyl)guanidino]-4-[(2-aminoethyl)thiomethyl]thiazole (0.12 g.) were dissolved in acetonitrile (5 ml.) and heated under reflux for 16 hours. The solvent was evaporated and the residual gum was partitioned between ethyl acetate (25 ml.) and 1N hydrochloric acid (25 ml.). The aqueous layer was basified with 10N sodium hydroxide solution and extracted with ethyl acetate (50 ml.). The organic layer was dried (magnesium sulphate) and evaporated to dryness. The residual gum was purified by preparative thin layer chromatography using ethyl acetate/methanol/ammonia 6:1:1 v/v/v as developing solvent. The appropriate zone of the chromatogram was isolated and extracted with methanol/ammonia 10:1 v/v. The solvent was evaporated and the residue dissolved in ethyl acetate, filtered and added to a solution of maleic acid (0.05 g.) in ethyl acetate. The precipitate was filtered to give 1-[2-(2-[(2,2,3,3-tetrafluoropropyl)guanidino]-thiazol-4-ylmethylthio)ethylamino]-1-methylamino-2-nitroethylene (0.04 g.), m.p. 115°–118° (decomp.) containing 1.4 molar equivalents of maleic acid.

EXAMPLE 79

The process described in Example 78 was repeated using 2-[2-(2,2,3,3,3-pentafluoropropyl)guanidino]-4-[(2-aminoethyl)thiomethyl]thiazole (0.15 g.) in place of 2-[2-(2,2,3,3-tetrafluoropropyl)guanidino]-4-[(2-aminoethyl)thiomethyl]thiazole and increasing the reaction time from 16 hours to 40 hours to give 1-[2-(2-[(2,2,3,3,3-pentafluoropropyl)guanidino]thiazol-4-ylmethylthio)ethylamino]-1-methylamino-2-nitroethylene (0.04 g.), m.p. 114°–117° (decomp.), containing 1.4 molar equivalents of maleic acid.

EXAMPLE 80

5-Methyl-N-nitroisothiourea (0.12 g.) and 2-[2-(2-chloro-2,2-difluoroethyl)guanidino]-4-[(2-aminoethyl)thiomethyl]thiazole (0.33 g.) were dissolved in ethanol (5 ml.) and allowed to stand at room temperature for 16 hours. The solvent was evaporated and the residual gum was purified by preparative thin layer chromatography using ethyl acetate/methanol/ammonia 6:1:1 v/v/v as developing solvent. The appropriate zone of the chromatogram was isolated and extracted with methanol/ammonia 10:1 v/v. The solvent was evaporated and the residue was dissolved in ethyl acetate, filtered and added to a solution of maleic acid (0.1 g.) in ethyl acetate. The precipitate was filtered to give 2-[2-(2-chloro-2,2-difluoroethyl)guanidino]-4-[2-(2-nitroguanidino)ethylthiomethyl]thiazole (0.28 g.), m.p. 112°–116°, containing 1.4 molar equivalents of maleic acid.

EXAMPLE 81

The process described in Example 80 was repeated using 2-[2-(2,2,3,3,3-pentafluoropropyl)guanidino]-4-[(2-aminoethyl)thiomethyl]thiazole (0.14 g.) in place of 2-[2-(2-chloro-2,2-difluoroethyl)guanidino]-4-[2-(aminoethyl)thiomethyl]thiazole to give 2-[2-(2,2,3,3,3-pentafluoropropyl)guanidino]-4-[2-(2-nitroguanidino)ethylthiomethyl]thiazole hydrogen maleate hemihydrate (0.1 g.), m.p. 140°–143°.

EXAMPLE 82

Dimethyl (propylsulphonylimido)dithiocarbonate (0.09 g.) and 2-[2-(2,2,3,3-tetrafluoropropyl)guanidino]-4-[(2-aminoethyl)thiomethyl]thiazole (0.14 g.) were dissolved in ethanol (2 ml.) and allowed to stand at room temperature for 16 hours. The solvent was evaporated and the residual gum was dissolved in ethanolic methylamine (33% w/v, 5 ml.) and allowed to stand at room temperature for 16 hours. The solvent was evaporated and the residual gum was purified by preparative thin layer chromatography using ethyl acetate/methanol/ammonia 6:1:1 v/v/v as developing solvent. The appropriate zone of the chromatogram was isolated and extracted with methanol/ammonia 10:1 v/v. The solvent was evaporated and the residue was dissolved in ethyl acetate, filtered and added to a solution of maleic acid (0.05 g.) in ethyl acetate. The precipitate was filtered to give 2-[2-(2,2,3,3-tetrafluoropropyl)guanidino]-4-[2-(2-propylsulphonyl-3-methylguanidino)ethylthiomethyl]thiazole hydrogen maleate (0.09 g.), m.p. 116°–118°.

EXAMPLE 83

The process described in Example 82 was repeated using 2-[2-(2-chloro-2,2-difluoroethyl)guanidino]-4-[(2-aminoethyl)thiomethyl]thiazole (0.16 g.) in place of 2-[2-(2,2,3,3-tetrafluoropropyl)guanidino]-4-[(2-aminoethyl)thiomethyl]thiazole and there was thus obtained 2-[2-(2-chloro-2,2-difluoroethyl)guanidino]-4-[2-(2-propylsulphonyl-3-methylguanidino)ethylthiomethyl]thiazole hydrogen maleate (0.12 g.), m.p. 107°–110°.

EXAMPLE 84

The process described in Example 73 was repeated using 4-[2-(2,2,3,3-tetrafluoropropyl)guanidino]-2-[3-aminopropylthio]pyrimidine (0.16 g.) in place of 2-[2-(2,2-difluoroethyl)guanidino]-4-[(2-aminoethyl)thiomethyl]thiazole and there was thus obtained 4-[2-(2,2,3,3-tetrafluoropropyl)guanidino]-2-[3-(2-methylsulphonyl-3-methylguanidino)propylthio]pyrimidine hydrogen maleate (0.09 g.), m.p. 157°–159°.

The 4-[2-(2,2,3,3-tetrafluoropropyl)guanidino]-2-[3-aminopropylthio]pyrimidine used as starting material may be obtained as follows:

Thiophosgene (10 ml.) was dissolved in 1,2-dichlorobenzene (50 ml.) and cooled to 5°. Separate solutions of 2,2,3,3-tetrafluoropropylamine hydrochloride (16.7 g.) in water (50 ml.) and potassium carbonate (69 g.) in water (150 ml.) were added simultaneously and dropwise with ice cooling and vigorous stirring. After the addition the mixture was stirred at room temperature for 2 hours then filtered and the organic layer was separated and dried (magnesium sulphate). The solution was distilled at 200 mm.Hg and the fraction boiling from 25°–110° was collected. This fraction was redistilled at 200 mm.Hg and the fraction boiling point 95°–105° collected to give a colourless oil (12.7 g.) containing 2,2,3,3-tetrafluoropropylisothiocyanate (83% w/w).

2,2,3,3-Tetrafluoropropylisothiocyanate (0.9 g.) and 2-(3-phthalimidopropylthio)-4-aminopyrimidine (0.9 g.) were dissolved in acetonitrile (30 ml.) and heated under reflux for 64 hours. The resulting suspension was cooled, filtered and the collected solid washed with acetonitrile (10 ml.) to give a white solid (0.9 g.). This was dissolved in a mixture of dimethylformamide (10 ml.) and saturated ethanolic ammonia solution (5 ml.) and treated with yellow mercuric oxide (0.8 g.). The mixture was stirred at room temperature for 3 hours. The solvent was evaporated and the black residue was triturated with ethyl acetate and filtered. The solvent was evaporated and the residual gum was dissolved in ethanol (15 ml.) and added to a solution of hydrazine (5 ml.) in ethanol (10 ml.). The mixture was stirred at room temperature for 2 hours then the solvent was evaporated. The residue was triturated with 1N hydrochloric acid, filtered and the filtrate was basified with 10N sodium hydroxide solution. The product was extracted with ethyl acetate, dried (magnesium sulphate) and the solvent was evaporated to give 4-[2-(2,2,3,3-tetrafluoropropyl)guanidino]-2-[3-aminopropylthio]pyrimidine (0.5 g.) which was used without further purification.

EXAMPLE 85

The process described in Example 77 was repeated using 4-[2-(2,2,3,3-tetrafluoropropyl)guanidino]-2-[3-aminopropylthio]pyrimidine (0.12 g.) in place of 2-[2-(2,2-difluoroethyl)guanidino]-4-[(2-aminoethyl)thiomethyl]thiazole and there was thus obtained 4-[2-(2,2,3,3-tetrafluoropropyl)guanidino]-2-[3-(2-cyano-3-methylguanidino)propylthio]pyrimidine hydrogen maleate (0.06 g.), m.p. 164° (decomp.).

EXAMPLE 86

To a solution of 2-[2-(2,2,2-trifluoroethyl)guanidino]-6-(2-aminoethylthio)pyrazine (0.16 g.) in ethanol (1 ml.) was added a solution of methylisothiocyanate (0.45 g.) in ethanol (1 ml.) and the mixture was stirred at room temperature for one hour. The mixture was evaporated, the residue basified with 2N NaOH and extracted with ethyl acetate. The extracts were dried over magnesium sulphate, filtered, and the filtrate concentrated to approximately 10 ml. A solution of maleic acid in ethyl acetate was added in excess, the mixture diluted with ether and allowed to stand. The resulting solid was filtered and recrystallised from ethanol to yield 0.08 g. of 2-[2-(2,2,2-trifluoroethyl)guanidino]-6-[2-(3-methylthioureido)ethylthio]pyrazine maleate, m.p. 182°–183°.

The 2-[2-(2,2,2-trifluoroethyl)guanidino]-2-(2-aminoethylthio)pyrazine used as starting material may be obtained as follows:

A solution of 2-amino-6-chloropyrazine (1 g.) in warm acetonitrile (15 ml.) was cooled to room temperature. Trifluoroethylisothiocyanate (1.6 g.) was added and the mixture stirred overnight. Further trifluoroethylisothiocyanate (1.6 g.) was added, and the mixture warmed gently on a steam bath for 2 hours, then heated under reflux for 2 hours. The mixture was allowed to cool and evaporated to dryness to yield a brown solid. This was washed with water, 2N HCl solution, water again, and sucked dry. Recrystallisation from boiling toluene diluted with petroleum ether (b.p. 60°–80°) yielded colourless needles (0.77 g.) of 2-[3-(2,2,2-trifluoroethyl)thioureido]-6-chloropyrazine m.p. 170°–172°.

To a solution of 2-[3-(2,2,2-trifluoroethyl)thioureido]-6-chloropyrazine (0.7 g.) in alcoholic ammonia (35 ml.) was added red mercuric oxide (0.65 g.) with stirring at room temperature. After stirring overnight, the black mixture was filtered and the black solid washed with alcohol. The resulting yellow filtrate was evaporated to give a yellow solid (0.7 g.). Recrystallisation from hot toluene diluted with petroleum ether (b.p. 60°–80°) yielded colourless needles (0.5 g.) of 2-[2-(2,2,2-trifluoroethyl)guanidino]-6-chloropyrazine m.p. 139°–140°.

Sodium hydride (50% w/w dispersion in oil; 0.114 g.) was added portionwise to ethanol (2 ml.). To the resulting solution was added 2-aminoethanethiol hydrochloride (0.134 g.) and the mixture stirred at room temperature. 2-[2-(2,2,2-Trifluoroethyl)guanidino]-6-chloropyrazine (0.1 g.) was added and the mixture heated under reflux on a steam bath for 22 hours. The mixture was cooled, evaporated, water added and extracted with ethyl acetate. The extracts were dried over magnesium sulphate, filtered and the filtrate evaporated to yield 2-[2-(2,2,2-trifluoroethyl)guanidino]-6-[(2-aminoethyl)thio]pyrazine as a gum (0.16 g.) which was used without further purification.

EXAMPLE 87

A solution of 2-[2-(2,2,2-trifluoroethyl)guanidino]-6-(3-aminopropylthio)pyrazine in warm acetonitrile (15 ml.) was allowed to cool to room temperature. A solution of methylisothiocyanate (0.15 g.) in acetonitrile (1 ml.) was added and the mixture stirred overnight. Evaporation to dryness gave a yellow solid which was recrystallised from a small volume of ethyl acetate to yield 2-[2-(2,2,2-trifluoroethyl)guanidino]-6-[3-(3-methylthioureido)-propylthio]pyrazine (0.32 g.), m.p. 165°–167°.

The 2-[2-(2,2,2-trifluoroethyl)guanidino]-6-(3-aminopropyl)pyrazine used as starting material may be prepared as follows:

Sodium hydride (50% w/w dispersion in oil; 0.57 g.) was added to ethanol (10 ml.) portionwise. To the resulting solution was added 3-aminopropanethiol hydrochloride (0.75 g.) and the mixture stirred at room temperature. 2-[2-(2,2,2-Trifluoroethyl)guanidino-6-chloropyrazine (0.5 g.) was added in one portion and the mixture heated under reflux on the steam bath overnight. The mixture was cooled, evaporated, water (10 ml.) added and the mixture extracted with ethyl acetate. The extracts were dried over magnesium sulphate, filtered and evaporated to yield an oil, which was chromatographed eluting with methanol/methylene chloride/ammonia 10:40:1 v/v/v to yield 2-[2-(2,2,2-trifluoroethyl)guanidino]-6-(3-aminopropylthio)pyrazine as a pale yellow solid (0.39 g.) which was used without further purification.

EXAMPLE 88

A solution of 3-[2-(2,2,2-trifluoroethyl)guanidino]-1-[2-(2-cyano-3-methylisothioureido)ethylthiomethyl]-benzene (0.416 g.) in 33% w/v methylamine in ethanol (4 ml.) was kept at 20° for 72 hours. Volatile material was evaporated in vacuo and the residue was fractionated on a silica column (26 cm. × 1 cm. diameter) eluted with ethyl acetate/ethanol/triethylamine 9:2:1 v/v/v. The product, 3-[2-(2,2,2-trifluoroethyl)guanidino]-1-[2-(2-cyano-3-methylguanidino)ethylthiomethyl]benzene, had n.m.r. spectrum in $d_6$ dimethylsulphoxide and $d_4$ acetic acid using tetramethyl silane as an internal standard ($\delta = 0$) containing the following resonances ($\delta$): 7.1 (4H, multiplet); 4.1 (2H, quartet); 3.7 (2H, singlet); 3.2 (2H, triplet); 2.7 (3H, singlet); 2.5 (2H, triplet).

The 3-[2-(2,2,2-trifluoroethyl)guanidino]-1-[2-(2-cyano-3-methylisothioureido)ethylthiomethyl]-benzene used as starting material may be prepared as follows:

m-Aminobenzyl alcohol (0.123 g.) and 2,2,2-trifluoroethylisothiocyanate (0.141 g.) were heated under reflux in acetone (5 ml.) for 2 hours. Volatile material was evaporated in vacuo and the crude residue was fractionated on a silica gel column (20 cm. × 1 cm. diameter)

eluted with ethyl acetate to give 1-(3-hydroxymethylphenyl)-3-(2,2,2-trifluoroethyl)thiourea. The n.m.r. spectrum in CDCl₃ using tetramethylsilane as internal standard ($\delta=0$) had the following resonances ($\delta$): 7.2 (4H, multiplet); 4.6 (2H, singlet); 4.3 (2H, multiplet).

The above thiourea (1.32 g.) was stirred in 1.6N alcoholic ammonia (50 ml.) with mercuric oxide (3.4 g.) for 17 hours at 20°. The resulting mixture was clarified on the centrifuge and the supernatant was evaporated in vacuo to a syrup which was further dried at 70°/0.1 m.m. to give 1-(3-hydroxymethylphenyl)-3-(2,2,2-trifluoroethyl)guanidine. The n.m.r. spectrum in d₆ dimethylsulphoxide using tetramethyl silane as internal standard ($\delta=0$) had the following resonances ($\delta$): 6.9 (4H, multiplet); 4.4 (2H, singlet); 3.9 (2H, quartet).

The above guanidine (1.121 g.) was dissolved in dry tetrahydrofuran (40 ml.) and thionyl chloride (0.7 ml.) was added. After 45 minutes at 30°–40° volatile material was evaporated in vacuo to give 1-(3-chloromethylphenyl)-3-(2,2,2-trifluoroethyl)guanidine as a syrup.

The above crude guanidine was dissolved in absolute alcohol (6 ml.) and 2-aminoethanethiol hydrochloride (0.51 g.) added. The mixture was stirred and cooled to 0°. 10.8 N-sodium hydroxide (0.9 ml.) was added over two minutes and the mixture was stirred at 0° for 2.75 hours. The resulting mixture was clarified on the centrifuge and the supernatant was evaporated in vacuo to a syrup which was shaken with water (15 ml.) and ethyl acetate (30 ml.). The ethyl acetate layer was separated and extracted with 2N hydrochloric acid (30 ml.) and the acid extract was basified with 2N sodium hydroxide and re-extracted with ethyl acetate (3×10 ml.). The extract was dried (MgSO₄) and evaporated in vacuo to give 1-[3-(2-aminoethyl)thiomethylphenyl]-3-(2,2,2-trifluoroethyl)guanidine as an oil.

The above amine (0.794 g.) was dissolved in alcohol (10 ml.) and dimethyl (cyanoimido)dithiocarbonate (0.379 g.) added. The mixture was kept at 20° while nitrogen was passed through for 20 hours. Volatile material was evaporated in vacuo and the residue was fractionated on a column of silica gel (40 cm.×2.5 cm. diameter) eluted with ethyl acetate/ethanol/triethylamine 9:2:1 v/v/v to give 3-[2-(2,2,2-trifluoroethyl)-guanidino]-1-[2-(2-cyano-3-methylisothioureido)ethylthiomethyl]benzene which was used without further purification. The n.m.r. spectrum in d₆ dimethylsulphoxide and d₄ acetic acid using tetramethylsilane as internal standard ($\delta=0$) had the following resonances ($\delta$): 7.1 (4H, multiplet); 4.0 (2H, quartet); 3.6 (2H, singlet); 3.4 (2H, triplet); 2.5 (2H, triplet); 2.4 (3H, singlet).

EXAMPLE 89

A solution of 5-[2-(2,2,2-trifluoroethyl)-guanidino]-3-[2-(3-cyano-2-methylisothioureido)ethylthiomethyl]-1,2,4-thiadiazole in 33% w/v methylamine in ethanol (4 ml.) was kept at 20° for 18 hours. Volatile material was evaporated in vacuo and the crude material was fractionated on a silica column (26 cm.×1 cm. diameter) eluted with a methanol/ethyl acetate 1:50 v/v to give 5-[2-(2,2,2-trifluoroethyl)guanidino]-3-[2-(2-cyano-3-methylguanidino)-ethylthiomethyl]-1,2,4-thiadiazole.
The n.m.r. spectrum in d₆ dimethylsulphoxide using tetramethyl silane as an internal standard ($\delta=0$) had the following resonances ($\delta$): 4.2 (2H, quartet); 3.8 (2H, singlet); 3.3 (2H, multiplet); 2.7 (2H, triplet).

The 5-[2-(2,2,2-trifluoroethyl)guanidino]-3-[2-(3-cyano-2-methylisothioureido)ethylthiomethyl]-1,2,4-thiadiazole used as starting material may be prepared as follows:

To a suspension of [N-(2,2,2-trifluoroethyl)-amidino]-thiourea maleate (33.2 g.) in ethanol (160 ml.) was added bromine (5.27 ml.) over 10 minutes. The mixture was stirred at 20° for 1 hour and evaporated in vacuo to an oil which crystallised upon trituration with ether. The product, 3-(2,2,2-trifluoroethyl)amino-5-amino-1,2,4-thiadiazole hydrobromide had m.p. 178°–180°. The free base, prepared by treating an aqueous solution of the hydrobromide with sodium bicarbonate, had m.p. 145°–146°.

3-(2,2,2-Trifluoroethyl)amino-5-amino-1,2,4-thiadiazole (2.0 g.) and tetrahydropyranyloxyacetamidine hydrochloride (2.0 g.) was added to a solution of sodium ethoxide prepared from sodium (0.46 g.) and alcohol (50 ml.). The resulting mixture was stirred at 20° for 4 hours then heated under reflux for 60 hours. Volatile material was evaporated in vacuo and the residue was shaken with 2N hydrochloric acid (30 ml.) and ethyl acetate (30 ml.). The aqueous layer was further extracted with ethyl acetate (3×30 ml.) then the pH was adjusted to 10 with 2N sodium hydroxide. The basified mixture was extracted with ethyl acetate (6×30 ml.) and the combined extracts were dried (MgSO₄) and evaporated in vacuo to give the crude product as an oil. It could be purified by fractionation on a silica gel column eluted with ethyl acetate to give 5-[2-(2,2,2-trifluoroethyl)guanidino]-3-hydroxymethyl-1,2,4-thiadiazole, m.p. 123°–125°.

Part of the above crude material (1.28 g.) was dissolved in dry tetrahydrofuran (40 ml.) and redistilled thionyl chloride (0.8 ml.) was added. After 1 hour at 25° volatile material was evaporated to give 5-[2-(2,2,2-trifluoroethyl)guanidino]-3-chloromethyl-1,2,4-thiadiazole. This chloromethyl compound was dissolved in absolute alcohol (5 ml.) and 2-aminoethanethiolhydrochloride (0.57 g.) was added followed by 10.8N sodium hydroxide (1 ml.) with external ice cooling. The mixture was stirred for 3 hours and the volatile material was then evaporated in vacuo. The residue was shaken with 2N hydrochloric acid (10 ml.) and ethyl acetate (10 ml.). The aqueous layer was basified with 2N sodium hydroxide and extracted with ethyl acetate (3×20 ml.). The ethyl acetate extracts were dried (MgSO₄) and evaporated in vacuo to give 5-[2-(2,2,2-trifluoroethyl)-guanidino]-3-[(2-amino)-ethylthiomethyl]-1,2,4-thiadiazole as an oil (0.9 g.)

The above (2-amino)ethylthiomethyl derivative was dissolved in alcohol (10 ml.) and dimethyl (cyanoimido)dithiocarbonate (0.446 g.) was added. The mixture was kept at 20° for 17 hours and then evaporated in vacuo to a syrup which was fractionated on a silica gel column (25 cm.×2.5 cm. diameter) which was eluted by ethyl acetate. The product, 5-[2-(2,2,2-trifluoroethyl)-guanidino]-3-[2-(3-cyano-2-methylisothioureido)ethylthiomethyl]-1,2,4-thiadiazole was used without further purification. The n.m.r. spectrum in d₆ dimethylsulphoxide using tetramethylsilane as an internal standard ($\delta=0$) had the following resonances ($\delta$): 4.1 (2H, quartet); 3.7 (2H, singlet); 3.5 (2H, quartet); 2.7 (2H, triplet); 2.5 (3H, singlet).

EXAMPLE 90

A mixture of 2-[2-(2,2,2-trifluoroethyl)guanidino]-4-[4-(3-cyano-2-methylisothioureido)butyl]thiazole (0.23 g.) and N-methylhydrazine (0.6 g.) in dimethylformamide (15 ml.) was heated at 40°–45° for 40 hours. The solvent was removed and the residue applied to 2 t.l.c. plates which were developed with chloroform/methanol/ammonia 9:1:0.1 v/v/v. The oil obtained was converted to a maleate in acetone to give 3-amino-1-methyl-5-[4-(2-[2-(2,2,2-trifluoroethyl)guanidino]-thiazol-4-yl)butylamino]-1H-1,2,4-triazole dimaleate (56.8 mg.), m.p. 181°–183°.

We claim:

1. A guanidine derivative of the formula:

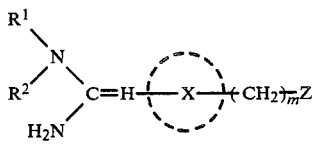

in which

R$^1$ and R$^2$, which may be the same or different, are hydrogen atoms or branched or unbranched alkyl radicals of 1 to 10 carbon atoms, cycloalkyl radicals of 3 to 8 carbon atoms or cycloalkylalkyl radicals in which the alkyl part is of 1 to 6 carbon atoms and the cycloalkyl part is of 3 to 8 carbon atoms, each of the alkyl, cycloalkyl and cycloalkylalkyl radicals being optionally substituted by one or more halogen atoms selected from fluorine, chlorine and bromine atoms, provided that at least one of R$^1$ and R$^2$ is a halogen substituted alkyl, cycloalkyl or cycloalkylalkyl radical and provided that there is no halogen substituent on the carbon atom of the alkyl, cycloalkyl or cycloalkylalkyl radical which is directly attached to the nitrogen atom;

ring X is a pyrimidine, ring which may, where possible, carry a single optional substituent, the optional substituents on ring X being selected from fluorine, chlorine, bromine and iodine atoms and alkyl, alkoxy and alkylthio radicals of 1 to 6 carbon atoms, trifluoromethyl, hydroxy and amino radicals;

Z is a radical of the formula —Y—(CH$_2$)$_n$—NH$_2$, —Q—H or —Cl;

Y is an oxygen or sulphur atom, a direct bond, a methylene, cis or trans vinylene or sulphinyl radical or a radical of the formula NR$^4$ in which R$^4$ is a hydrogen atom or an alkyl radical of 1 to 6 carbon atoms;

m is 0 to 4 and n is 1 to 5, provided that when Y is an oxygen atom, a sulphinyl radical or a radical of the formula NR$^4$, n is 2 to 5; and Q is an oxygen or sulfur atom or a radical of the formula NR$^4$.

2. The guanidine derivative of claim 1, in which R$^1$ and R$^2$ are selected from the group consisting of hydrogen atoms and 2,2,2-trifluoroethyl, 2,2,2-trichloroethyl, 2-chloro-2,2-difluoroethyl, 2,2-dichloro-2-fluoroethyl, 2-bromo-2,2-difluoroethyl, 2,2-dibromo-2-fluoroethyl, 2-fluoroethyl, 2-chloroethyl, 2,2-difluoroethyl, 2,2-dichloroethyl, 2-chloro-2-fluoroethyl, 2-bromo-2-fluoroethyl, 2,2,3,3,3-pentafluoropropyl, 1,1,1,3,3,3-hexafluoroisopropyl, 1,3-dichloro-1,1,3,3-tetrafluoroisopropyl, 1-chloro-1,1,3,3,3-pentafluoroisopropyl, 1,3-difluoroisopropyl, 2,2,3,3,4,4,4-heptafluorobutyl, 2,2,3,3-tetrafluorocyclopropyl, 2-chloro-2,3,3-trifluorocyclopropyl, 2,2-difluorocyclopropyl, 2-chloro-3,3-difluorocyclopropyl, 2,2,3,3,4,4-hexafluorocyclobutyl, 2-chloro-2,3,3,4,4-pentafluorocyclobutyl, (1,2,2,3,3-pentafluorocyclopropyl)methyl, (2-chloro-1,2,3,3-tetrafluorocyclopropyl)methyl, (1,2,2,3,3,4,4-heptafluorocyclobutyl)-methyl, (2-chloro-1,2,3,3,4,4-hexafluorocyclobutyl)methyl, methyl, ethyl, propyl, isopropyl, butyl, cyclopropyl, cyclobutyl, cyclopropylmethyl and cyclopropylbutyl radicals provided that at least one of R$^1$ and R$^2$ is a halogen-substituted radical;

ring X is a pyrimidine, ring each optionally substituted, where possible by a fluorine, chlorine, bromine or iodine atom or by a methyl, methoxy, methylthio, trifluoromethyl, hydroxy or amino radical; and R$^4$ is a hydrogen atom or a methyl radical.

3. The guanidine derivative of claim 1, in which R$^1$ carries at least one fluorine atom on the carbon atom which is one carbon atom removed from the nitrogen atom to which the radical is attached and R$^2$ is a hydrogen atom.

4. The guanidine derivative of claim 1, in which ring X is a pyrimidine ring in which the guanidine radical is substituted at the 4-position and (CH$_2$)$_m$ at the 2-position.

5. The guanidine derivative of claim 1, in which m is 0.

* * * * *